(12) United States Patent
Hammock et al.

(10) Patent No.: US 9,029,401 B2
(45) Date of Patent: May 12, 2015

(54) SORAFENIB DERIVATIVES AS SEH INHIBITORS

(75) Inventors: Bruce D. Hammock, Davis, CA (US);
Sung Hee Hwang, Davis, CA (US);
Aaron T. Wecksler, Davis, CA (US);
Christophe Morisseau, West Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/985,039

(22) PCT Filed: Feb. 14, 2012

(86) PCT No.: PCT/US2012/025074
§ 371 (c)(1),
(2), (4) Date: Nov. 22, 2013

(87) PCT Pub. No.: WO2012/112570
PCT Pub. Date: Aug. 23, 2012

(65) Prior Publication Data
US 2014/0088156 A1      Mar. 27, 2014

Related U.S. Application Data

(60) Provisional application No. 61/442,364, filed on Feb. 14, 2011, provisional application No. 61/593,822, filed on Feb. 1, 2012.

(51) Int. Cl.
| | | |
|---|---|---|
| C07C 275/38 | (2006.01) | |
| C07C 275/26 | (2006.01) | |
| C07C 275/30 | (2006.01) | |
| C07D 213/643 | (2006.01) | |
| C07D 213/79 | (2006.01) | |
| C07D 213/81 | (2006.01) | |
| C07D 401/06 | (2006.01) | |
| C07D 213/64 | (2006.01) | |
| C07C 275/34 | (2006.01) | |

(52) U.S. Cl.
CPC ............ *C07C 275/38* (2013.01); *C07D 213/64* (2013.01); *C07D 213/79* (2013.01); *C07D 213/81* (2013.01); *C07C 275/30* (2013.01); *C07C 275/34* (2013.01); *C07C 275/26* (2013.01); *C07D 213/643* (2013.01); *C07D 401/06* (2013.01); *C07C 2101/14* (2013.01)

(58) Field of Classification Search
None
See application file for complete search history.

(56) References Cited

U.S. PATENT DOCUMENTS

| | | |
|---|---|---|
| 6,503,949 B1 | 1/2003 | Lau et al. |
| 6,875,760 B2 | 4/2005 | Lau et al. |
| 2003/0181442 A1 | 9/2003 | Riedl et al. |
| 2009/0023731 A1* | 1/2009 | Gless et al. ............... 514/235.5 |

OTHER PUBLICATIONS

International Search Report and Written Opinion for PCT/US2012/025074, 11 pages, mailed May 25, 2012.
Hwang, Sung Hee et al.: "*Orally Bioavailable Potent Soluble Epoxide Hydrolase Inhibitors*"; J Med Chem, American Chemical Society, US; Jan. 1, 2007, 50:16; 3825-3840.
Liu, J-Y et al.: "*Sorafenib has soluble epoxide hydrolase inhibitory activity, which contributes to its effect profile in vivo*"; Moleccular Cancer Therapeutics, Am Assoc Cancer Research, Aug. 1, 2009; 8:8, 2193-2203.
Database Accession No. 1222848-63-6: Database Registry May 13, 2010; Chemical Abstracts Service, Columbus, OH.
European Search Report regarding EP 12 74 6691.

* cited by examiner

*Primary Examiner* — Timothy R Rozof
(74) *Attorney, Agent, or Firm* — DLA Piper LLP (US)

(57) ABSTRACT

The present invention provides compounds for the inhibition of soluble epoxide hydrolase and associated disease conditions.

24 Claims, 11 Drawing Sheets

SORAFENIB DERIVATIVES AS SEH INHIBITORS

CROSS-REFERENCE TO RELATED APPLICATIONS

This application is the U.S. National Stage entry under §371 of International Application No. PCT/US2012/025074, filed Feb. 14, 2012, which claims priority to U.S. Provisional Application Nos. 61/442,364, filed Feb. 14, 2011 and 61/593,822, filed Feb. 1, 2012, which are incorporated in their entirety herein.

STATEMENT AS TO RIGHTS TO INVENTIONS MADE UNDER FEDERALLY SPONSORED RESEARCH AND DEVELOPMENT

This invention was made with Government support under Grant No. R37 ES02710, awarded by the National Institute of Environmental Health Sciences, and under Grant NO. P42 ES04699, awarded by the National Institute of Health/National Institute of Environmental Health Sciences Superfund. The Government has certain rights in this invention.

BACKGROUND OF THE INVENTION

Epoxide hydrolases (EHs) catalyze the hydrolysis of aliphatic epoxides or arene oxides to their corresponding diols by the addition of water (see, Oesch, F., et al., *Xenobiotica* 1973, 3, 305-340). Some EHs play an important role in the metabolism of a variety of compounds including hormones, chemotherapeutic drugs, carcinogens, environmental pollutants, mycotoxins, and other harmful foreign compounds.

There are two well-studied EHs, microsomal epoxide hydrolase (mEH, EC 3.3.2.9) and soluble epoxide hydrolase (sEH, EC3.3.2.10). These enzymes are very distantly related, have different subcellular localization, and have different but partially overlapping substrate selectivities. The soluble and microsomal EH forms are known to complement each other in degrading some plant natural products (see, Hammock, B. D., et al., COMPREHENSIVE TOXICOLOGY. Oxford: Pergamon Press 1997, 283-305 and Fretland, A. J., et al., *Chem. Biol. Intereract* 2000, 129, 41-59).

The major role of the sEH is in the metabolism of lipid epoxides including the metabolism of arachidonic acid (see, Zeldin, D. C., et al., *J. Biol. Chem.* 1993, 268, 6402-6407), linoleic acid (see, Moghaddam, M. F., et al., *Nat. Med.* 1997, 3, 562-567), and from other fatty acids some of which are endogenous chemical mediators (see, Carroll, M. A., et al., *Thorax* 2000, 55, S13-16). Epoxides of arachidonic acid (cis-epoxyeicosatrienoic acids or EETs) and other lipid epoxides are known effectors of blood pressure (see, Capdevila, J. H., et al., *J. Lipid. Res.* 2000, 41, 163-181), and modulators of vascular permeability (see, Oltman, C. L., et al., *Circ Res.* 1998, 83, 932-939). The vasodilatory properties of EETs are associated with an increased open-state probability of calcium-activated potassium channels leading to hyperpolarization of the vascular smooth muscle (see Fisslthaler, B., et al., *Nature* 1999, 401, 493-497). Hydrolysis of the EETs by sEH diminishes this activity (see, Capdevila, J. H., et al., *J. Lipid. Res.* 2000, 41, 163-181). Hydrolysis of EETs by sEH also regulates their incorporation into coronary endothelial phospholipids, suggesting a regulation of endothelial function by sEH (see, Weintraub, N. L., et al., *Am. J. Physiol.* 1992, 277, H2098-2108). It has been shown that treatment of spontaneous hypertensive rats (SHRs) with selective sEH inhibitors significantly reduces their blood pressure (see, Yu, Z., et al., *Circ. Res.* 2000 87, 992-998). In addition, it was claimed that male knockout sEH mice have significantly lower blood pressure than wild-type mice (see Sinal, C. J., et al., *J. Biol. Chem.* 2000, 275, 40504-405010), however subsequent studies with back breeding into C57b mice demonstrated that 20-HETE levels increased compensating for the increase in plasma EETs (see, Luria, A. et al., *J. Biol. Chem.* 2007, 282:2891-2898.

The EETs have also demonstrated anti-inflammatory properties in endothelial cells (see, Node, K., et al., *Science* 1999, 285, 1276-1279 and Campbell, W. B. *Trends Pharmacol. Sci.* 2000, 21, 125-127). In contrast, diols derived from epoxylinoleate (leukotoxin) perturb membrane permeability and calcium homeostasis (see, Moghaddam, M. F., et al., *Nat. Med.* 1997, 3, 562-567), which results in inflammation that is modulated by nitric oxide synthase and endothelin-1 (see, Ishizaki, T., et al., *Am. J. Physiol.* 1995, 269, L65-70 and Ishizaki, T., et al., *J. Appl. Physiol.* 1995, 79, 1106-1611). Micromolar concentrations of leukotoxin reported in association with inflammation and hypoxia (see, Dudda, A., et al., *Chem. Phys. Lipids* 1996, 82, 39-51), depress mitochondrial respiration in vitro (see, Sakai, T., et al., *Am. J. Physiol.* 1995, 269, L326-331), and cause mammalian cardiopulmonary toxicity in vivo (see, Ishizaki, T., et al., *Am. J. Physiol.* 1995, 269, L65-70; Fukushima, A., et al., *Cardiovasc. Res.* 1988, 22, 213-218; and Ishizaki, T., et al., *Am. J. Physiol.* 1995, 268, L123-128). Leukotoxin toxicity presents symptoms suggestive of multiple organ failure and acute respiratory distress syndrome (ARDS) (see, Ozawa, T. et al., *Am. Rev. Respir. Dis.* 1988, 137, 535-540). In both cellular and organismal models, leukotoxin-mediated toxicity is dependent upon epoxide hydrolysis (see, Moghaddam, M. F., et al., *Nat. Med.* 1997, 3, 562-567; Morisseau, C., et al., *Proc. Natl. Acad. Sci. USA* 1999, 96, 8849-8854; and Zheng, J., et al., *Am. J. Respir. Cell Mol. Biol.* 2001, 25, 434-438), suggesting roles for sEH in the regulation of inflammation and vascular permeability. The bioactivity of these epoxy-fatty acids suggests that inhibition of vicinal-dihydroxy-lipid biosynthesis may have therapeutic value, making sEH a promising pharmacological target.

1,3-disubstituted ureas, carbamates, and amides have been reported as new potent and stable inhibitors of sEH (See, U.S. Pat. No. 6,150,415). These compounds are competitive tight-binding inhibitors with nanomolar $K_I$ values that interact stoichiometrically with purified human recombinant sEH (see, Morisseau, C., et al., *Proc. Natl. Acad. Sci. USA* 1999, 96, 8849-8854). Based on the X-ray crystal structure, the urea inhibitors were shown to establish strong hydrogen bonds between the urea group of the inhibitor and residues of the sEH active site, mimicking features encountered in the reaction coordinate of epoxide ring opening by this enzyme (see, Argiriadi, M. A., et al., *Proc. Natl. Acad. Sci. USA* 1999, 96, 10637-10642 and Argiriadi, M. A., et al., *J. Biol. Chem.* 2000, 275, 15265-15270). These inhibitors efficiently reduced epoxide hydrolysis in several in vitro and in vivo models (see Yu, Z., et al., *Circ. Res.* 2000, 87, 992-998; Morisseau, C., et al., *Proc. Natl. Acad. Sci. USA* 1999, 96, 8849-8854; and Newman, J. W., et al., *Environ. Health Perspect.* 2001, 109, 61-66). Despite the high activity associated with these inhibitors, there exists a need for compounds possessing similar or increased activities, preferably with improved water solubility and/or pharmacokinetic properties to facilitate formulation and delivery.

The present invention provides such compounds along with methods for their use and compositions that contain them.

BRIEF SUMMARY OF THE INVENTION

In one embodiment, the present invention provides compounds of formula I:

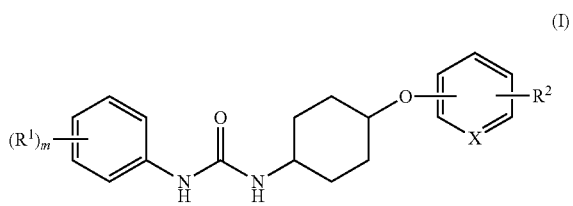

(I)

wherein $R^1$ of formula I is halogen, $C_{1-6}$ haloalkyl or $C_{1-6}$ haloalkoxy; $R^2$ is —CN, $C_{1-6}$ haloalkyl, $C_{1-6}$ haloalkoxy, —C(O)O$R^{2a}$ or —C(O)N$R^{2a}R^{2b}$; $R^{2a}$ and $R^{2b}$ are each independently H, $C_{1-6}$ alkyl or $C_{3-8}$ cycloalkyl, or are taken together to form a 5- or 6-membered heterocycloalkyl ring; X is —CH— or —N—; subscript m is an integer from 1 to 3; such that when X is —CH—, $R^2$ is —C(O)OH, and subscript m is 1, then $R^1$ is halogen or $C_{1-6}$ haloalkyl; and salts or isomers thereof.

In another embodiment, the present invention provides a pharmaceutical composition, including a compound of the present invention and a pharmaceutically acceptable excipient.

In other embodiments, the present invention provides a method for inhibiting a soluble epoxide hydrolase, the method including contacting the soluble epoxide hydrolase with a therapeutically effective amount of a compound of the present invention, thereby inhibiting the soluble epoxide hydrolase.

In some other embodiments, the present invention provides a method for monitoring the activity of a soluble epoxide hydrolase, the method including contacting the soluble epoxide hydrolase with an amount of a compound of the present invention sufficient to produce a detectable change in the fluorescence of the soluble epoxide hydrolase by interacting with one or more tryptophan residues present in the catalytic site of said soluble epoxide hydrolase, thereby monitoring the activity of the soluble epoxide hydrolase.

In another embodiment, the present invention provides a method for inhibiting a kinase, the method including contacting the kinase with a therapeutically effective amount of a compound of the present invention, thereby inhibiting the kinase.

In other embodiments, the present invention provides a method for monitoring the activity of a kinase, the method including contacting the kinase with an amount of a compound of the present invention sufficient to produce detectable changes in adenosine diphosphate (ADP (luminescence spectroscopy), thereby monitoring the activity of the kinase.

In some other embodiments, the present invention provides a method of treating cancer, the method including administering to a subject in need thereof, a therapeutically effective amount of a compound of the present invention, thereby treating cancer.

In some embodiments, the present invention provides a method of treating cancer, the method including contacting cancer cells with a therapeutically effective amount of a compound of the present invention, thereby treating cancer.

Arrows show areas of AIF nuclear accumulation after mitochondrial depolarization. These data suggest a role AIF in the mechanism of cell death by sorafenib and the analogues.

Figure 11:
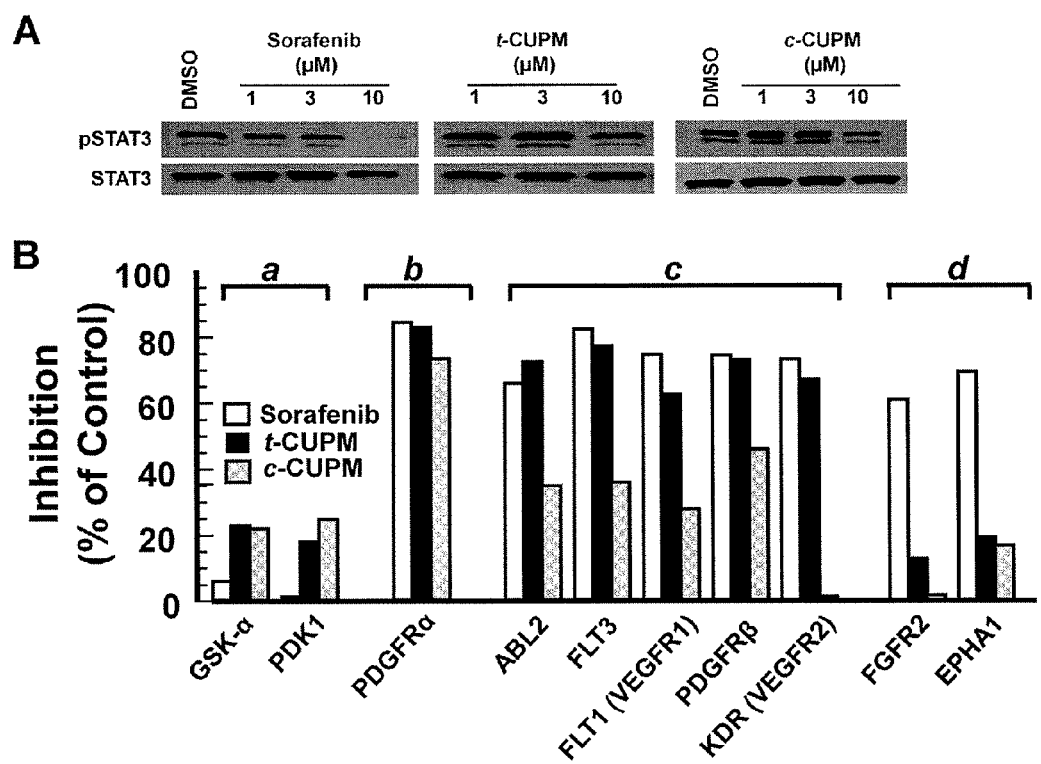

FIG. 11 shows that sorafenib analogues inhibit STAT3 and exhibit distinct selectivity profiles. (A) Western blot detection of phosphorylated STAT3. Cells were exposed to compounds for 24 hours at indicated concentrations. (B) Selectivity screening against 10 recombinant kinases at 10 µM test concentrations. [a] Negative controls for sorafenib activity. [b] Comparable inhibition by all three compounds. [c] Comparable inhibition by sorafenib and t-CUPM only. [d] Inhibition by sorafenib only. These data demonstrate that isomeric conformation dictates selectivity profiles of the sorafenib analogues.

DETAILED DESCRIPTION OF THE INVENTION

I. General

The present invention derives from the discovery that 1,3-disubstituted ureas (or the corresponding amides or carbamates, also referred to as the primary pharmacophore) can be further functionalized to provide more potent sEH inhibitors with kinase inhibitory activity. As described herein, the introduction of a halo-, haloalkyl, or haloalkoxy-phenyl group and a pyridyl or phenyl group linked with a cyclohexyloxy group, or combinations thereof, mimics sorafenib and improves the activity of the sEH inhibitors. The combination of these moieties provides a variety of compounds of increased water solubility.

II. Definitions

"Soluble epoxide hydrolase" ("sEH") is an enzyme which in endothelial, smooth muscle and other cell types converts EETs to the corresponding diol compounds called dihydroxyeicosatrienoic acids ("DHETs"). The cloning and sequence of the murine sEH is set forth in Grant et al., *J. Biol. Chem.* 268(23):17628-17633 (1993). The cloning, sequence, and accession numbers of the human sEH sequence are set forth in Beetham et al., *Arch. Biochem. Biophys.* 305(1):197-201 (1993). The amino acid sequence of human sEH is also set forth as SEQ ID NO:2 of U.S. Pat. No. 5,445,956; the nucleic acid sequence encoding the human sEH is set forth as nucleotides 42-1703 of SEQ ID NO:1 of that patent. The evolution and nomenclature of the gene is discussed in Beetham et al., *DNA Cell Biol.* 14(1):61-71 (1995). Soluble epoxide hydrolase represents a single highly conserved gene product with over 90% homology between rodent and human (Arand et al., *FEBS Lett.,* 338:251-256 (1994)).

As used herein, the terms "treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

The term "modulate" refers to the ability of a compound to increase or decrease the function, or activity, of the associated activity (e.g., soluble epoxide hydrolase). "Modulation", as used herein in its various forms, is meant to include antagonism and partial antagonism of the activity associated with sEH. Inhibitors of sEH are compounds that, e.g., bind to, partially or totally block the enzyme's activity.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In some embodiments, the subject is a human.

As used herein, the term "sEH-mediated disease or condition" and the like refers to a disease or condition characterized by less than or greater than normal, sEH activity. A sEH-mediated disease or condition is one in which modulation of sEH results in some effect on the underlying condition or disease (e.g., a sEH inhibitor or antagonist results in some improvement in patient well-being in at least some patients).

As used herein, the term "kinase-mediated disease or condition" and the like refers to a disease or condition characterized by less than or greater than normal, kinase activity. A kinase-mediated disease or condition is one in which modulation of kinase results in some effect on the underlying condition or disease (e.g., a kinase inhibitor or antagonist results in some improvement in patient well-being in at least some patients).

"Cancer" refers to a class of diseases in which a group of cells display uncontrolled growth, invasion intrudes upon and destroys adjacent tissues, and/or metastasis by spreading to other locations in the body via lymph or blood.

"Parenchyma" refers to the tissue characteristic of an organ, as distinguished from associated connective or supporting tissues.

"Chronic Obstructive Pulmonary Disease" or "COPD" is also sometimes known as "chronic obstructive airway disease", "chronic obstructive lung disease", and "chronic airways disease." COPD is generally defined as a disorder characterized by reduced maximal expiratory flow and slow forced emptying of the lungs. COPD is considered to encompass two related conditions, emphysema and chronic bronchitis. COPD can be diagnosed by the general practitioner using art recognized techniques, such as the patient's forced vital capacity ("FVC"), the maximum volume of air that can be forcibly expelled after a maximal inhalation. In the offices of general practitioners, the FVC is typically approximated by a 6 second maximal exhalation through a spirometer. The definition, diagnosis and treatment of COPD, emphysema, and chronic bronchitis are well known in the art and discussed in detail by, for example, Honig and Ingram, in Harrison's Principles of Internal Medicine, (Fauci et al., Eds.), 14th Ed., 1998, McGraw-Hill, New York, pp. 1451-1460 (hereafter, "Harrison's Principles of Internal Medicine").

"Emphysema" is a disease of the lungs characterized by permanent destructive enlargement of the airspaces distal to the terminal bronchioles without obvious fibrosis.

"Chronic bronchitis" is a disease of the lungs characterized by chronic bronchial secretions which last for most days of a month, for three months a year, for two years.

As the names imply, "obstructive pulmonary disease" and "obstructive lung disease" refer to obstructive diseases, as opposed to restrictive diseases. These diseases particularly include COPD, bronchial asthma and small airway disease.

"Small airway disease." There is a distinct minority of patients whose airflow obstruction is due, solely or predominantly to involvement of the small airways. These are defined as airways less than 2 mm in diameter and correspond to small cartilaginous bronchi, terminal bronchioles and respiratory bronchioles. Small airway disease (SAD) represents luminal obstruction by inflammatory and fibrotic changes that increase airway resistance. The obstruction may be transient or permanent.

The "interstitial lung diseases (ILDs)" are a group of conditions involving the alveolar walls, perialveolar tissues, and contiguous supporting structures. As discussed on the website of the American Lung Association, the tissue between the air sacs of the lung is the interstitium, and this is the tissue affected by fibrosis in the disease. Persons with the disease have difficulty breathing in because of the stiffness of the lung tissue but, in contrast to persons with obstructive lung disease, have no difficulty breathing out. The definition, diagnosis and treatment of interstitial lung diseases are well known in the art and discussed in detail by, for example, Reynolds, H. Y., in Harrison's Principles of Internal Medicine, supra, at pp. 1460-1466. Reynolds notes that, while ILDs have various initiating events, the immunopathological responses of lung tissue are limited and the ILDs therefore have common features.

"Idiopathic pulmonary fibrosis," or "IPF," is considered the prototype ILD. Although it is idiopathic in that the cause is not known.

"Inhibition", "inhibits", "inhibiting" and "inhibitor" refer to a compound that prohibits or a method of prohibiting, a specific action or function.

As used herein, the term "contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

As used herein, the term "alkyl" refers to a saturated hydrocarbon which may be straight-chain such as ethyl, or branched-chain such as isopropyl, t-amyl, or 2,5-dimethylhexyl. This definition applies both when the term is used alone and when it is used as part of a compound term, such as "arylalkyl," "alkylamino" and similar terms. In some embodiments, alkyl groups are those containing 1 to 24 carbon atoms. All numerical ranges in this specification and claims are intended to be inclusive of their upper and lower limits. Additionally, the alkyl and heteroalkyl groups may be attached to other moieties at any position on the alkyl or heteroalkyl group which would otherwise be occupied by a hydrogen atom, for example, 2-pentyl, 2-methylpent-1-yl or 2-propyloxy group. Divalent alkyl groups may be referred to as "alkylene," and divalent heteroalkyl groups may be referred to as "heteroalkylene," such as those groups used as linkers in the present invention. The alkyl, alkylene, and heteroalkylene moieties may also be optionally substituted with halogen atoms, or other groups such as oxo, cyano, nitro, alkyl, alkylamino, carboxyl, hydroxyl, alkoxy, aryloxy, and the like.

As used herein, the term "cycloalkyl" refers to a saturated or partially unsaturated, monocyclic, fused bicyclic or bridged polycyclic ring assembly containing from 3 to 12 ring atoms, or the number of atoms indicated. For example, $C_3$-$C_8$ cycloalkyl includes cyclopropyl, cyclobutyl, cyclopentyl, cyclohexyl, cycloheptyl, and cyclooctyl. Cycloalkyl also includes norbornyl and adamantyl.

As used herein, the term "heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. Some heterocycloalkyl groups have from 3 to 8 ring members and from 1 to 3 heteroatoms such as N, O and S. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

The term "alkenyl" as used herein refers to an alkyl group as described above which contains one or more sites of unsaturation that is a double bond. Similarly, the term "alkynyl" as used herein refers to an alkyl group as described above which contains one or more sites of unsaturation that is a triple bond.

The term "alkoxy" refers to an alkyl radical as described above which also bears an oxygen substituent which is capable of covalent attachment to another hydrocarbon for example, methoxy, ethoxy or t-butoxy group.

The term "aryl" refers to an aromatic carbocyclic substituent which may be a single ring or multiple rings which are fused together, linked covalently or linked to a common group such as an ethylene or methylene moiety. Similarly, aryl groups having a heteroatom (e.g. N, O or S) in place of a carbon atom on the ring are referred to as "heteroaryl". Examples of aryl and heteroaryl groups are, for example, phenyl, naphthyl, biphenyl, diphenylmethyl, thienyl, pyridyl and quinoxalyl. The aryl and heteroaryl moieties may also be optionally substituted with halogen atoms, or other groups such as nitro, alkyl, alkylamino, carboxyl, alkoxy, phenoxy and the like. Additionally, the aryl and heteroaryl groups may be attached to other moieties at any position on the aryl or heteroaryl radical which would otherwise be occupied by a hydrogen atom, for example, 2-pyridyl, 3-pyridyl or 4-pyridyl group. Divalent aryl groups are "arylene", and divalent heteroaryl groups are referred to as "heteroarylene" such as those groups used as linkers in the present invention.

The terms "halo" or "halogen," by themselves or as part of another substituent, mean, unless otherwise stated, a fluorine, chlorine, bromine, or iodine atom. Additionally, terms such as "haloalkyl," and "haloalkoxy" are meant to include monohaloalkyl(oxy) and polyhaloalkyl(oxy). For example, the term "$C_1$-$C_6$ haloalkyl" is mean to include trifluoromethyl, 2,2,2-trifluoroethyl, 4-chlorobutyl, 3-bromopropyl, and the like.

The term "substituted" refers to the replacement of an atom or a group of atoms of a compound with another atom or group of atoms. For example, an atom or a group of atoms may be substituted with one or more of the following substituents or groups: halo, nitro, $C_1$-$C_8$alkyl, $C_1$-$C_8$alkylamino, hydroxy$C_1$-$C_8$alkyl, halo$C_1$-$C_8$alkyl, carboxyl, hydroxyl, $C_1$-$C_8$alkoxy, $C_1$-$C_8$alkoxy$C_1$-$C_8$alkoxy, thio$C_1$-$C_8$alkyl, aryl, aryloxy, $C_3$-$C_8$cycloalkyl, $C_3$-$C_8$cycloalkyl$C_1$-$C_8$alkyl, heteroaryl, aryl$C_1$-$C_8$alkyl, heteroaryl$C_1$-$C_8$alkyl, $C_2$-$C_8$alkenyl containing 1 to 2 double bonds, $C_2$-$C_8$alkynyl containing 1 to 2 triple bonds, $C_4$-$C_8$alk(en)(yn)yl groups, cyano, formyl, $C_1$-$C_8$alkylcarbonyl, arylcarbonyl, heteroarylcarbonyl, $C_1$-$C_8$alkoxycarbonyl, aryloxycarbonyl, aminocarbonyl, $C_1$-$C_8$alkylaminocarbonyl, $C_1$-$C_8$dialkylaminocarbonyl, arylaminocarbonyl, diarylaminocarbonyl, aryl$C_1$-$C_8$alkylaminocarbonyl, halo$C_1$-$C_8$alkoxy, $C_2$-$C_8$alkenyloxy, $C_2$-$C_8$alkynyloxy, aryl$C_1$-$C_8$alkoxy, amino$C_1$-$C_8$alkyl, $C_1$-$C_8$alkylamino$C_1$-$C_8$alkyl, $C_1$-$C_8$dialkylamino$C_1$-$C_8$alkyl, arylamino$C_1$-$C_8$alkyl, amino, $C_1$-$C_8$dialkylamino, arylamino, aryl$C_1$-

$C_8$alkylamino, $C_1$-$C_8$alkylcarbonylamino, arylcarbonylamino, azido, mercapto, $C_1$-$C_8$alkylthio, arylthio, halo$C_1$-$C_8$alkylthio, thiocyano, isothiocyano, $C_1$-$C_8$alkylsulfinyl, $C_1$-$C_8$alkylsulfonyl, arylsulfinyl, arylsulfonyl, aminosulfonyl, $C_1$-$C_8$alkylaminosulfonyl, $C_1$-$C_8$dialkylaminosulfonyl and arylaminosulfonyl. When the term "substituted" appears prior to a list of possible substituted groups, it is intended that the term apply to every member of that group.

The term "unsubstituted" refers to a native compound that lacks replacement of an atom or a group of atoms.

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

As used herein, the term "pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

The term "kinase" refers to an enzyme that transfers phosphate groups from donor molecules like adenosine triphosphate (ATP), to substrates. Kinases are also known as a phosphotransferase. Many kinases are known, including protein kinases, receptor kinases and proto oncogene kinases such as Raf-1, encoded by the RAF1 gene, and b-Raf, encoded by the BRAF gene.

III. Compounds

The compounds of the present invention are sorafenib derivatives having the formula:

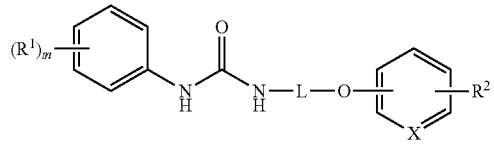

wherein $R^1$ of formula I is halogen, $C_{1-6}$ haloalkyl or $C_{1-6}$ haloalkoxy; L is $C_{3-8}$ cycloalkyl; $R^2$ is —CN, $C_{1-6}$ haloalkyl, $C_{1-6}$ haloalkoxy, —C(O)OR$^{2a}$ or —C(O)NR$^{2a}$R$^{2b}$; R$^{2a}$ and $R^{2b}$ are each independently H, $C_{1-6}$ alkyl or $C_{3-8}$ cycloalkyl, or are taken together to form a 5- or 6-membered heterocycloalkyl ring; X is —CH— or —N—; subscript m is an integer from 1 to 3; and salts or isomers thereof. In some embodiments, the compounds are those where when X is —CH—, L is cyclohexyl, $R^2$ is —C(O)OH, and subscript m is 1, then $R^1$ is halogen or $C_{1-6}$ haloalkyl.

In some embodiments, the present invention provides compounds of formula I:

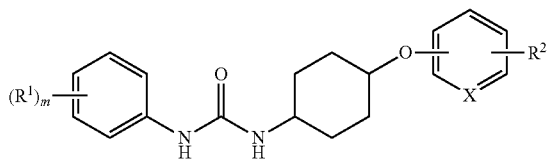

(I)

wherein $R^1$ of formula I is halogen, $C_{1-6}$ haloalkyl or $C_{1-6}$ haloalkoxy; $R^2$ is —CN, $C_{1-6}$ haloalkyl, $C_{1-6}$ haloalkoxy, —C(O)OR$^{2a}$ or —C(O)NR$^{2a}$R$^{2b}$; R$^{2a}$ and $R^{2b}$ are each independently H, $C_{1-6}$ alkyl or $C_{3-8}$ cycloalkyl, or are taken together to form a 5- or 6-membered heterocycloalkyl ring; X is —CH— or —N—; subscript m is an integer from 1 to 3; and salts or isomers thereof. In some embodiments, the compounds of formula I are those where $R^1$ is halogen, $C_{1-6}$ haloalkyl or $C_{1-6}$ haloalkoxy; $R^2$ is —CN, $C_{1-6}$ haloalkyl, $C_{1-6}$ haloalkoxy, —C(O)OR$^{2a}$ or —C(O)NR$^{2a}$R$^{2b}$; $R^{2a}$ and $R^{2b}$ are each independently H, $C_{1-6}$ alkyl or $C_{3-8}$ cycloalkyl, or are taken together to form a 5- or 6-membered heterocycloalkyl ring; X is —CH— or —N—; subscript m is an integer from 1 to 3; such that when X is —CH—, $R^2$ is —C(O)OH, and subscript m is 1, then $R^1$ is halogen or $C_{1-6}$ haloalkyl; and salts or isomers thereof.

In other embodiments, the compounds of formula I wherein $R^1$ is halogen, $C_{1-6}$ haloalkyl or $C_{1-6}$ haloalkoxy; $R^2$ is $C_{1-6}$haloalkyl, $C_{1-6}$ haloalkoxy, —C(O)OR$^{2a}$ or —C(O)NR$^{2a}$R$^{2b}$; R$^{2a}$ and $R^{2b}$ are each independently H, $C_{1-6}$ alkyl or $C_{3-8}$ cycloalkyl; X is —CH— or —N—; subscript m is an integer from 1 to 3; such that when X is —CH—, $R^2$ is —C(O)OH, and subscript m is 1, then $R^1$ is halogen or $C_{1-6}$ haloalkyl; and salts and isomers thereof.

In other embodiments, X is —CH—. In some other embodiments, X is —N—. In still other embodiments, $R^2$ is —C(O)OR$^{2a}$ or —C(O)NR$^{2a}$R$^{2b}$.

In another embodiment, the compound has the formula:

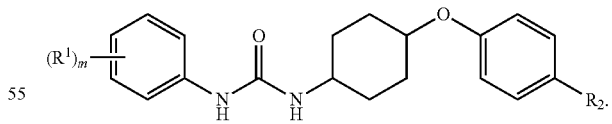

In other embodiments, the compound has the formula:

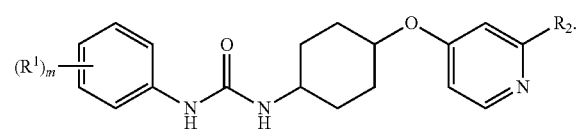

In other embodiments, the compound has the formula:
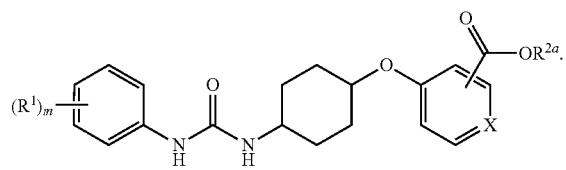
In other embodiments, the compound has the formula:
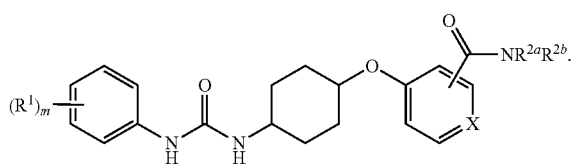
In other embodiments, the compound has the formula:
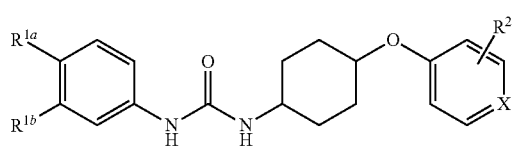
wherein $R^{1a}$ and $R^{1b}$ are each independently halogen or $C_{1-6}$ haloalkyl. In other embodiments, the compound has the formula:
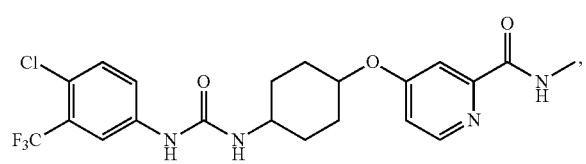
In other embodiments, the compound is:
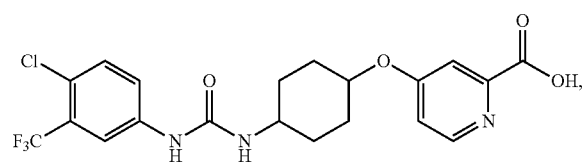
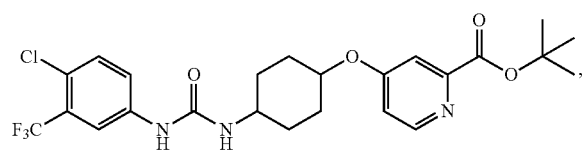
-continued
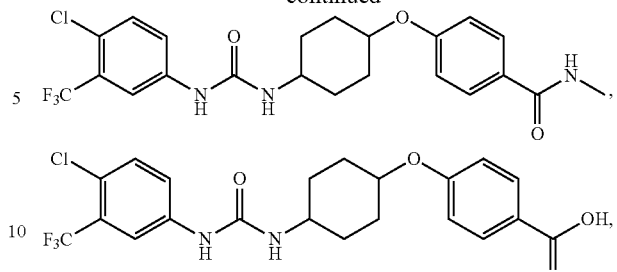
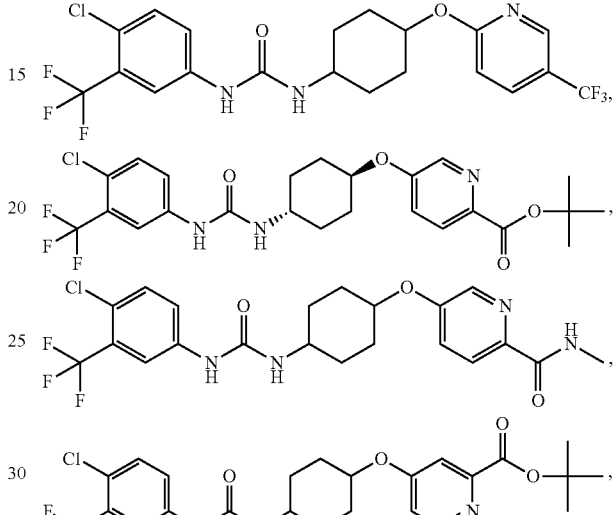
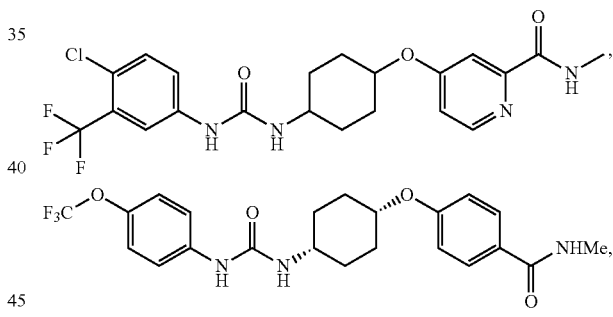
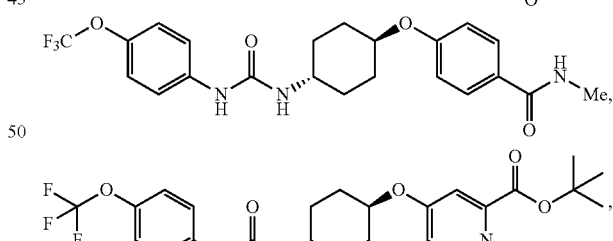
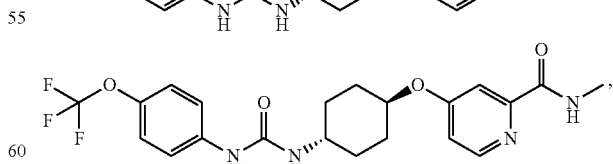
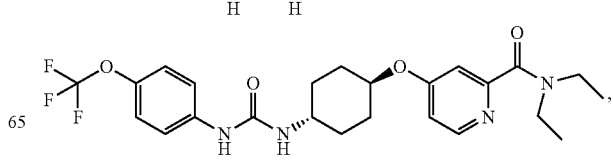

-continued

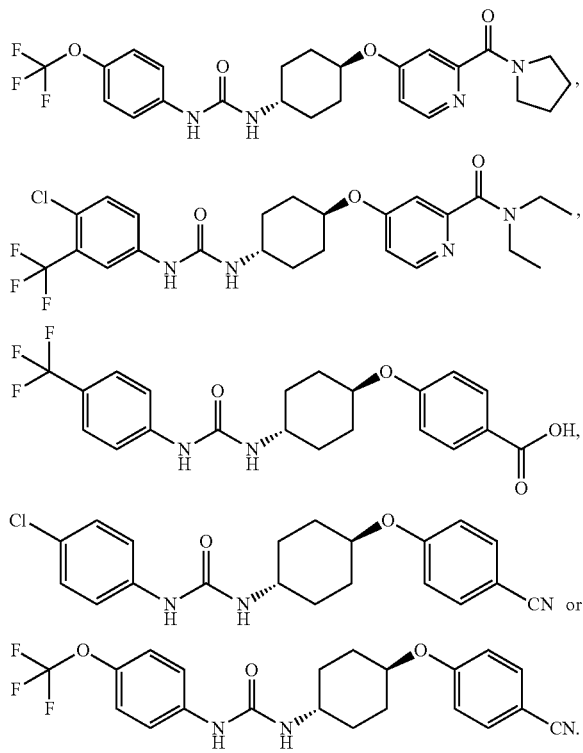

In other embodiments, the compound is:

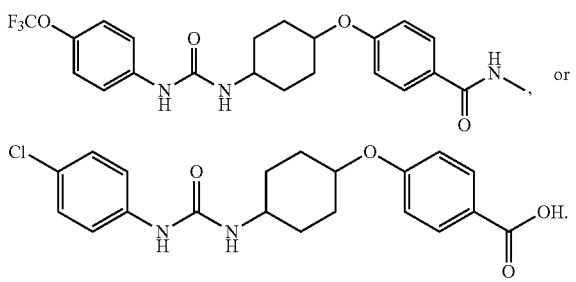

In other embodiments, the compound is:

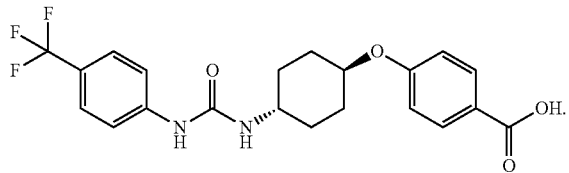 [SMILES: O=C(Nc1ccc(C(F)(F)F)cc1)N[C@H]1CC[C@H](Oc2ccc(C(=O)O)cc2)CC1]

In other embodiments, the compound can be:

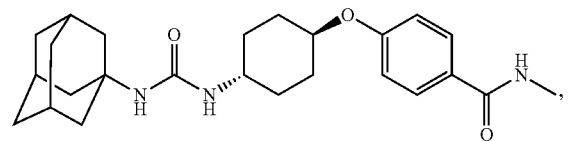

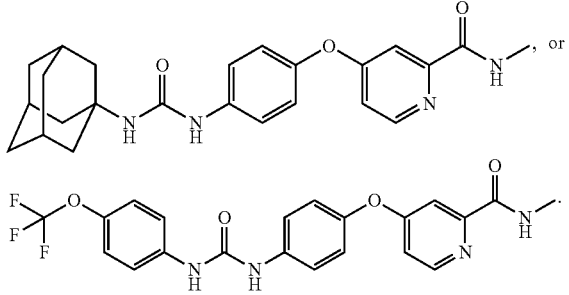

Certain compounds of the present invention possess asymmetric carbon atoms (optical centers) or double bonds; the racemates, diastereomers, geometric isomers and individual isomers are all intended to be encompassed within the scope of the present invention.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Figure 1:
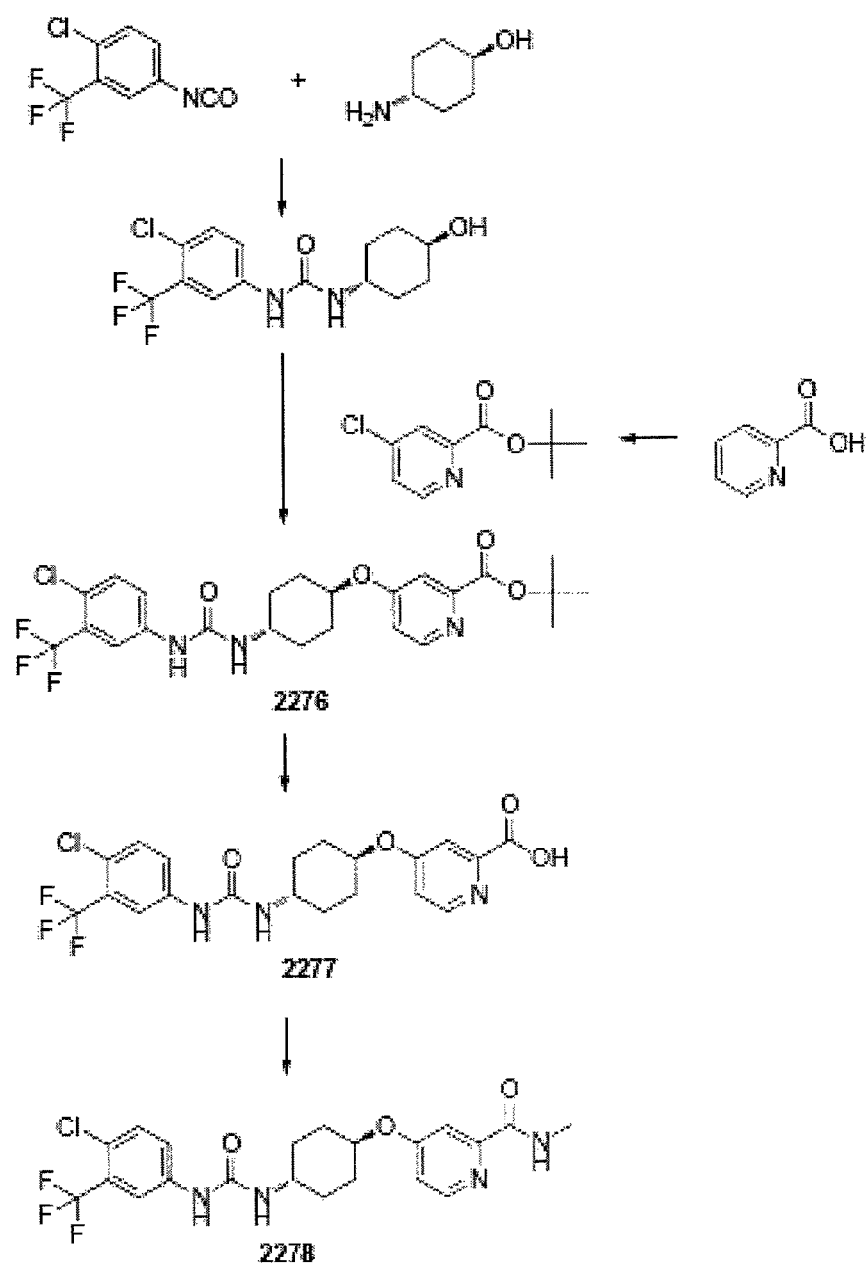
FIG. 1 shows a scheme for the preparation of the compounds of the present invention.
Figure 2:
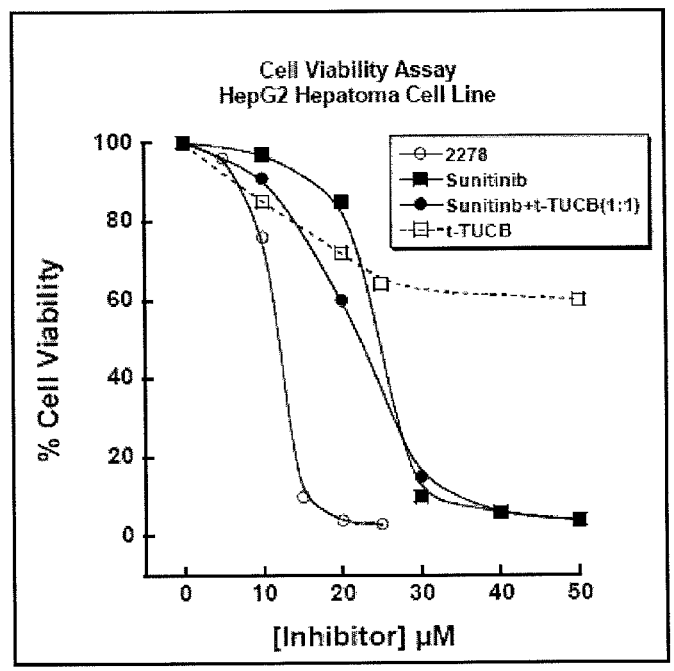
FIG. 2 shows dose dependence of a sEH inhibitor (t-TUCB), a MAPK inhibitor (sunitinib) and a combination inhibitor (2278) on Hep G2 cell viability. The sEH inhibitor t-TUCB has a limited effect on the cancer cells. However, when administered in combination with to sunitinib, a MAPK inhibitor, it potentiates this latter compound's ability to kill cancer cells. Compound 2278, which inhibits both sEH and MAPK (see Table 1) is more efficient than sunitinib in combination or not, with t-TUCB, in killing the cancer cells.
Figure 3:
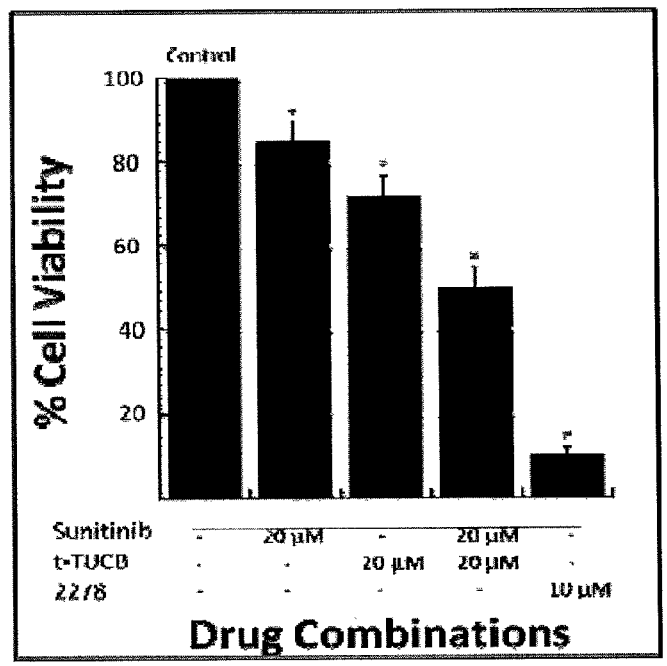
FIG. 3 shows a comparison of the effect of various sEH and MAPK inhibitors on Hep G2 cell viability. Even at a concentration 2-fold smaller, compound 2278 which inhibits both sEH and MAPK (see Table 1) is more efficient than sunitinib in combination or not, with t-TUCB, in killing the cancer cells.

The compounds of the present invention can be prepared by a variety of methods known to one of skill in the art, such as described in FIG. 1, or in Richard C. Larock, *Comprehensive Organic Transformations* 1989, VCH Publishers, Inc.

IV. Pharmaceutical Compositions

In another embodiment, the present invention provides a pharmaceutical composition, including a compound of the present invention and a pharmaceutically acceptable excipient.

The compounds of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. The compounds of the present invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable carrier or excipient and either a compound of the present invention, or a pharmaceutically acceptable salt of a compound of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound.

The compositions typically include a conventional pharmaceutical carrier or excipient and may additionally include other medicinal agents, carriers, adjuvants, diluents, tissue permeation enhancers, solubilizers, and the like. Preferably, the composition will contain about 0.01% to about 90%, preferably about 0.1% to about 75%, more preferably about 0.1% to 50%, still more preferably about 0.1% to 10% by weight of a ligand of the present invention or a combination thereof, with the remainder consisting of suitable pharmaceutical carrier and/or excipients. Appropriate excipients can be tailored to the particular composition and route of administration by methods well known in the art, e.g., REMINGTON'S PHARMACEUTICAL SCIENCES, supra.

Suitable solid excipients include, but are not limited to, magnesium carbonate; magnesium stearate; calcium phosphate; calcium silicate; talc; pectin; dextran, dextrin, and cyclodextrin inclusion complexes; a low melting wax; cocoa butter; carbohydrates; sugars including, but not limited to, lactose, dextrose, sucrose, mannitol, or sorbitol; starches including, but not limited to, starch from corn, wheat, rice, potato, or other plants; cellulose such as methyl cellulose, hydroxypropylmethyl-cellulose, or sodium carboxymethyl-cellulose; and gums including arabic, tragacanth, and acacia; as well as proteins including, but not limited to, gelatin, collagen; microcrystalline cellulose, water, saline, syrup, ethylcellulose, and polyacrylic acids such as Carbopols, e.g., Carbopol 941, Carbopol 980, Carbopol 981, etc.; lubricating agents; mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents; biodegradable polymer beads. If desired, disintegrating or solubilizing agents may be added, such as the cross-linked polyvinyl pyrrolidone, agar, alginic acid, alginates, or a salt thereof, such as sodium alginate.

A pharmaceutically acceptable carrier may include physiologically acceptable compounds that act, for example, to stabilize the compounds of the present invention or modulate their absorption, or other excipients as desired. Physiologically acceptable compounds include, for example, carbohydrates, such as glucose, sucrose or dextrans, antioxidants, such as ascorbic acid or glutathione, chelating agents, low molecular weight proteins or other stabilizers or excipients.

One skilled in the art would know that the choice of a pharmaceutically acceptable carrier, including a physiologically acceptable compound, depends, for example, on the route of administration of the compounds of the present invention and on the particular physio-chemical characteristics of the compounds of the present invention.

Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, maltose, sucrose or dextrins, chelating agents such as EDTA, glutathione and other stabilizers and excipients. Neutral buffered saline or saline mixed with nonspecific serum albumin are exemplary appropriate diluents.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a compound of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

V. Administration

Administration of the compounds of the present invention with a suitable pharmaceutical excipient as necessary can be carried out via any of the accepted modes of administration. Thus, administration can be, for example, intravenous, topical, subcutaneous, transcutaneous, transdermal, intramuscular, oral, intra-joint, parenteral, intra-arteriole, intradermal, intraventricular, intracranial, intraperitoneal, intralesional, intranasal, rectal, vaginal, or by inhalation. Administration may also be directly to the bone surface and/or into tissues surrounding the bone.

The compositions containing a compound or a combination of compounds of the present invention may be administered repeatedly, e.g., at least 2, 3, 4, 5, 6, 7, 8, or more times, or the composition may be administered by continuous infusion. Suitable sites of administration include, but are not limited to, skin, bronchial, gastrointestinal, anal, vaginal, eye, and ear. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, gels, aerosols, or the like, preferably in unit dosage forms suitable for simple administration of precise dosages.

The pharmaceutical preparations are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

The pharmaceutical preparation is preferably in unit dosage form. The term "unit dosage form" refers to physically discrete units suitable as unitary dosages for human subjects and other mammals (e.g., dogs), each unit containing a predetermined quantity of active material calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of a compound or a combination of compounds. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the invention in a sustained release formulation.

Methods for preparing such dosage forms are known to those skilled in the art (see, for example, REMINGTON'S PHARMACEUTICAL SCIENCES, 18TH ED., Mack Publishing Co., Easton, Pa. (1990)). The composition to be administered contains a quantity of the compound or combination of compounds in a pharmaceutically effective amount for relief of a condition being treated (e.g. osteoporosis) when administered in accordance with the teachings of this invention. In addition, pharmaceutically acceptable salts of the compounds of the present invention (e.g., acid addition salts) may be prepared and included in the compositions using standard procedures known to those skilled in the art of synthetic organic chemistry and described, e.g., by J. March, Advanced Organic Chemistry: Reactions, Mechanisms and Structure, $4^{th}$ Ed. (New York: Wiley-Interscience, 1992).

For oral administration, the compositions can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the pharmaceutical compositions take the form of a pill, tablet, or capsule, and thus, the composition can contain, along with the compounds or combination of compounds, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. The compounds can also be formulated into a suppository disposed, for example, in a polyethylene glycol (PEG) carrier.

Liquid compositions can be prepared by dissolving or dispersing a compound or a combination of compounds and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. The compounds of the present invention can also be formulated into a retention enema.

For topical administration, the compositions of the present invention can be in the form of emulsions, lotions, gels, creams, jellies, solutions, suspensions, ointments, and transdermal patches. For delivery by inhalation, the composition can be delivered as a dry powder or in liquid form via a nebulizer. For parenteral administration, the compositions can be in the form of sterile injectable solutions and sterile packaged powders. Preferably, injectable solutions are formulated at a pH of about 4.5 to about 7.5.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

Generally, administered dosages will be effective to deliver picomolar to micromolar concentrations of the compound to the appropriate site or sites. However, one of ordinary skill in the art understands that the dose administered will vary depending on a number of factors, including, but not limited to, the particular compound or set of compounds to be administered, the mode of administration, the type of application (e.g., imaging, therapeutic), the age of the patient, and the physical condition of the patient. Preferably, the smallest dose and concentration required to produce the desired result should be used. Dosage should be appropriately adjusted for children, the elderly, debilitated patients, and patients with cardiac and/or liver disease. Further guidance can be obtained from studies known in the art using experimental animal models for evaluating dosage. However, the increased cell binding affinity and specificity associated with the compounds of the present invention permits a wider margin of safety for dosage concentrations and for repeated dosing.

The pharmaceutical compositions of the present invention can be prepared for administration by a variety of different routes. In general, the type of carrier is selected based on the mode of administration. Pharmaceutical compositions can be formulated for any appropriate manner of administration, including, for example, topical, oral, nasal, intrathecal, rectal, vaginal, sublingual or parenteral administration, including subcutaneous, intravenous, intramuscular, intrastemal, intracavemous, intrameatal, or intraurethral injection or infusion. A pharmaceutical composition (e.g., for oral administration or delivery by injection) can be in the form of a liquid (e.g., an elixir, syrup, solution, emulsion or suspension). A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The formulations of the invention are also suitable for administration in all body spaces/cavities, including but not limited to pleura, peritoneum, cranium, mediastinum, pericardium, bursae or bursal, epidural, intrathecal, intraocular, intra-articular, intra-discal, intra-medullary, perispinal, etc.

Some slow release embodiments include polymeric substances that are biodegradable and/or dissolve slowly. Such polymeric substances include polyvinylpyrrolidone, low- and medium-molecular-weight hydroxypropyl cellulose and hydroxypropyl methylcellulose, cross-linked sodium carboxymethylcellulose, carboxymethyl starch, potassium methacrylatedivinylbenzene copolymer, polyvinyl alcohols, starches, starch derivatives, microcrystalline cellulose, ethylcellulose, methylcellulose, and cellulose derivatives, β-cyclodextrin, poly(methyl vinyl ethers/maleic anhydride), glucans, scierozlucans, mannans, xanthans, alzinic acid and derivatives thereof, dextrin derivatives, glyceryl monostearate, semisynthetic glycerides, glyceryl palmitostearate, glyceryl behenate, polyvinylpyrrolidone, gelatine, agnesium stearate, stearic acid, sodium stearate, talc, sodium benzoate, boric acid, and colloidal silica.

Slow release agents of the invention may also include adjuvants such as starch, pregelled starch, calcium phosphate mannitol, lactose, saccharose, glucose, sorbitol, microcrystalline cellulose, gelatin, polyvinylpyrrolidone, methylcellulose, starch solution, ethylcellulose, arabic gum, tragacanth gum, magnesium stearate, stearic acid, colloidal silica, glyceryl monostearate, hydrogenated castor oil, waxes, and mono-, bi-, and trisubstituted glycerides. Slow release agents may also be prepared as generally described in WO94/06416.

In practicing the methods of the present invention, the pharmaceutical compositions can be used alone, or in combination with other therapeutic or diagnostic agents. The additional drugs used in the combination protocols of the present invention can be administered separately or one or more of the drugs used in the combination protocols can be administered together, such as in an admixture. Where one or more drugs are administered separately, the timing and schedule of administration of each drug can vary. The other therapeutic or diagnostic agents can be administered at the same time as the compounds of the present invention, separately or at different times.

VI. Methods

In some embodiments, the present invention provides a method for inhibiting a soluble epoxide hydrolase, the method including contacting the soluble epoxide hydrolase with a therapeutically effective amount of a compound of the present invention, thereby inhibiting the soluble epoxide hydrolase. In other embodiments, the compound further inhibits a kinase. In some other embodiments, the kinase can be Raf-1 or b-Raf.

In other embodiments, the present invention provides a method for monitoring the activity of a soluble epoxide hydrolase, the method including contacting the soluble epoxide hydrolase with an amount of a compound of the present invention sufficient to produce a detectable change in the fluorescence of the soluble epoxide hydrolase by interacting with one or more tryptophan residues present in the catalytic site of said soluble epoxide hydrolase, thereby monitoring the activity of the soluble epoxide hydrolase.

In another embodiment, the present invention provides a method for inhibiting a kinase, such as Raf-1 kinase, the method including contacting the kinase with a therapeutically effective amount of a compound of the present invention, thereby inhibiting the kinase. In some other embodiments, the kinase can be Raf-1 or b-Raf.

In some other embodiments, the present invention provides a method for monitoring the activity of a kinase, the method including contacting the kinase with an amount of a compound of the present invention sufficient to produce detectable changes in adenosine diphosphate (ADP) (luminescence spectroscopy) by the kinase thereby monitoring the activity of the kinase.

In another embodiment, the present invention provides a method for the simultaneous inhibition of both soluble epoxide hydrolase and a kinase by means of a single compound or by way of combining two or more compounds which inhibit both soluble epoxide hydrolase and a kinase for the treatment of human diseases, such as cancer.

In some embodiments, the present invention provides a method of treating cancer, the method including administering to a subject in need thereof, a therapeutically effective amount of a compound of the present invention, thereby treating cancer.

In some embodiments, the present invention provides a method of treating cancer, the method including contacting cancer cells with a therapeutically effective amount of a compound of the present invention, thereby treating cancer. The contacting can be in vivo or in vitro. In some embodiments, the contacting is performed in vitro.

A. Methods of Treating Diseases Modulated by Soluble Epoxide Hydrolases:

In another aspect, the present invention provides methods of treating diseases, especially those modulated by soluble epoxide hydrolase (sEH). The methods generally involve administering to a subject in need of such treatment an effective amount of a compound of the present invention. The dose, frequency and timing of such administering will depend in large part on the selected therapeutic agent, the nature of the condition being treated, the condition of the subject including age, weight and presence of other conditions or disorders, the formulation being administered and the discretion of the attending physician. Preferably, the compositions and compounds of the invention and the pharmaceutically acceptable salts thereof are administered via oral, parenteral, subcutaneous, intramuscular, intravenous or topical routes. Generally, the compounds are administered in dosages ranging from about 2 mg up to about 2,000 mg per day, although variations will necessarily occur depending, as noted above, on the disease target, the patient, and the route of administration. Dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day. The dosage employed for the topical administration will, of course, depend on the size of the area being treated.

It has previously been shown that inhibitors of soluble epoxide hydrolase ("sEH") can reduce hypertension. See, e.g., U.S. Pat. No. 6,351,506. Such inhibitors can be useful in controlling the blood pressure of persons with undesirably high blood pressure, including those who suffer from diabetes.

In some embodiments, compounds of the present invention are administered to a subject in need of treatment for cancer, hypertension, specifically renal, hepatic, or pulmonary hypertension; inflammation, specifically renal inflammation, vascular inflammation, and lung inflammation; adult respiratory distress syndrome; diabetic complications; end stage renal disease; Raynaud syndrome and arthritis.

B. Methods for Inhibiting Progression of Kidney Deterioration (Nephropathy) and Reducing Blood Pressure:

In another aspect of the invention, the compounds of the invention can reduce damage to the kidney, and especially damage to kidneys from diabetes, as measured by albuminuria. The compounds of the invention can reduce kidney deterioration (nephropathy) from diabetes even in individuals who do not have high blood pressure. The conditions of therapeutic administration are as described above.

cis-Epoxyeicosantrienoic acids ("EETs") can be used in conjunction with the compounds of the invention to further reduce kidney damage. EETs, which are epoxides of arachidonic acid, are known to be effectors of blood pressure, regulators of inflammation, and modulators of vascular permeability. Hydrolysis of the EETs by sEH diminishes this activity. Inhibition of sEH raises the level of EETs since the rate at which the EETs are hydrolyzed into DHETs is reduced. Without wishing to be bound by theory, it is believed that raising the level of EETs interferes with damage to kidney cells by the microvasculature changes and other pathologic effects of diabetic hyperglycemia. Therefore, raising the EET level in the kidney is believed to protect the kidney from progression from microalbuminuria to end stage renal disease.

EETs are well known in the art. EETs useful in the methods of the present invention include 14,15-EET, 8,9-EET and 11,12-EET, and 5,6-EETs, in that order of preference. Preferably, the EETs are administered as the methyl ester, which is more stable. Persons of skill will recognize that the EETs are regioisomers, such as 8S,9R- and 14R,15S-EET. 8,9-EET, 11,12-EET, and 14R,15S-EET, are commercially available from, for example, Sigma-Aldrich (catalog nos. E5516, E5641, and E5766, respectively, Sigma-Aldrich Corp., St. Louis, Mo.).

EETs produced by the endothelium have anti-hypertensive properties and the EETs 11,12-EET and 14,15-EET may be endothelium-derived hyperpolarizing factors (EDHFs). Additionally, EETs such as 11,12-EET have profibrinolytic effects, anti-inflammatory actions and inhibit smooth muscle cell proliferation and migration. In the context of the present invention, these favorable properties are believed to protect the vasculature and organs during renal and cardiovascular disease states.

It is now believed that sEH activity can be inhibited sufficiently to increase the levels of EETs and thus augment the effects of administering sEH inhibitors by themselves. This permits EETs to be used in conjunction with one or more sEH inhibitors to reduce nephropathy in the methods of the invention. It further permits EETs to be used in conjunction with one or more sEH inhibitors to reduce hypertension, or inflammation, or both. Thus, medicaments of EETs can be made which can be administered in conjunction with one or more sEH inhibitors, or a medicament containing one or more sEH inhibitors can optionally contain one or more EETs.

The EETs can be administered concurrently with the sEH inhibitor, or following administration of the sEH inhibitor. It is understood that, like all drugs, inhibitors have half lives defined by the rate at which they are metabolized by or excreted from the body, and that the inhibitor will have a period following administration during which it will be present in amounts sufficient to be effective. If EETs are administered after the inhibitor is administered, therefore, it is desirable that the EETs be administered during the period during which the inhibitor will be present in amounts to be effective to delay hydrolysis of the EETs. Typically, the EET or EETs will be administered within 48 hours of administering an sEH inhibitor. Preferably, the EET or EETs are administered within 24 hours of the inhibitor, and even more preferably within 12 hours. In increasing order of desirability, the EET or EETs are administered within 10, 8, 6, 4, 2, hours, 1 hour, or one half hour after administration of the inhibitor. Most preferably, the EET or EETs are administered concurrently with the inhibitor.

In some embodiments, the EETs, the compound of the invention, or both, are provided in a material that permits them to be released over time to provide a longer duration of action. Slow release coatings are well known in the pharmaceutical art; the choice of the particular slow release coating is not critical to the practice of the present invention.

EETs are subject to degradation under acidic conditions. Thus, if the EETs are to be administered orally, it is desirable that they are protected from degradation in the stomach. Conveniently, EETs for oral administration may be coated to permit them to passage the acidic environment of the stomach into the basic environment of the intestines. Such coatings are well known in the art. For example, aspirin coated with so-called "enteric coatings" is widely available commercially. Such enteric coatings may be used to protect EETs during passage through the stomach. An exemplary coating is set forth in the Examples.

While the anti-hypertensive effects of EETs have been recognized, EETs have not been administered to treat hypertension because it was thought endogenous sEH would hydrolyze the EETs too quickly for them to have any useful effect. Surprisingly, it was found during the course of the studies underlying the present invention that exogenously administered inhibitors of sEH succeeded in inhibiting sEH sufficiently that levels of EETs could be further raised by the administration of exogenous EETs. These findings underlie the co-administration of sEH inhibitors and of EETs described above with respect to inhibiting the development and progression of nephropathy. This is an important improvement in augmenting treatment. While levels of endogenous EETs are expected to rise with the inhibition of sEH activity caused by the action of the sEH inhibitor, and therefore to result in at least some improvement in symptoms or pathology, it may not be sufficient in all cases to inhibit progression of kidney damage fully or to the extent intended. This is particularly true where the diseases or other factors have reduced the endogenous concentrations of EETs below those normally present in healthy individuals. Administration of exogenous EETs in conjunction with a sEH inhibitor is therefore expected to be beneficial and to augment the effects of the sEH inhibitor in reducing the progression of diabetic nephropathy.

The present invention can be used with regard to any and all forms of diabetes to the extent that they are associated with progressive damage to the kidney or kidney function. The chronic hyperglycemia of diabetes is associated with long-term damage, dysfunction, and failure of various organs, especially the eyes, kidneys, nerves, heart, and blood vessels. The long-term complications of diabetes include retinopathy with potential loss of vision; nephropathy leading to renal failure; peripheral neuropathy with risk of foot ulcers, amputation, and Charcot joints.

In addition, persons with metabolic syndrome are at high risk of progression to type 2 diabetes, and therefore at higher risk than average for diabetic nephropathy. It is therefore desirable to monitor such individuals for microalbuminuria, and to administer a sEH inhibitor and, optionally, one or more EETs, as an intervention to reduce the development of nephropathy. The practitioner may wait until microalbuminuria is seen before beginning the intervention. As noted above, a person can be diagnosed with metabolic syndrome without having a blood pressure of 130/85 or higher. Both persons with blood pressure of 130/85 or higher and persons with blood pressure below 130/85 can benefit from the administration of sEH inhibitors and, optionally, of one or more EETs, to slow the progression of damage to their kidneys. In some embodiments, the person has metabolic syndrome and blood pressure below 130/85.

Dyslipidemia or disorders of lipid metabolism is another risk factor for heart disease. Such disorders include an increased level of LDL cholesterol, a reduced level of HDL cholesterol, and an increased level of triglycerides. An increased level of serum cholesterol, and especially of LDL cholesterol, is associated with an increased risk of heart disease. The kidneys are also damaged by such high levels. It is believed that high levels of triglycerides are associated with kidney damage. In particular, levels of cholesterol over 200 mg/dL, and especially levels over 225 mg/dL, would suggest that sEH inhibitors and, optionally, EETs, should be administered. Similarly, triglyceride levels of more than 215 mg/dL, and especially of 250 mg/dL or higher, would indicate that administration of sEH inhibitors and, optionally, of EETs, would be desirable. The administration of compounds of the present invention with or without the EETs, can reduce the need to administer statin drugs (HMG-CoA reductase inhibitors) to the patients, or reduce the amount of the statins needed. In some embodiments, candidates for the methods, uses and compositions of the invention have triglyceride levels over 215 mg/dL and blood pressure below 130/85. In some embodiments, the candidates have triglyceride levels over 250 mg/dL and blood pressure below 130/85. In some embodiments, candidates for the methods, uses and compositions of the invention have cholesterol levels over 200 mg/dL and blood pressure below 130/85. In some embodiments, the candidates have cholesterol levels over 225 mg/dL and blood pressure below 130/85.

C. Methods of Inhibiting the Proliferation of Vascular Smooth Muscle Cells:

In other embodiments, compounds of the present invention inhibit proliferation of vascular smooth muscle (VSM) cells without significant cell toxicity, (e.g., specific to VSM cells). Because VSM cell proliferation is an integral process in the pathophysiology of atherosclerosis, these compounds are suitable for slowing or inhibiting atherosclerosis. These compounds are useful to subjects at risk for atherosclerosis, such as individuals who have had a heart attack or a test result showing decreased blood circulation to the heart. The conditions of therapeutic administration are as described above.

The methods of the invention are particularly useful for patients who have had percutaneous intervention, such as angioplasty to reopen a narrowed artery, to reduce or to slow the narrowing of the reopened passage by restenosis. In some embodiments, the artery is a coronary artery. The compounds of the invention can be placed on stents in polymeric coatings to provide a controlled localized release to reduce restenosis. Polymer compositions for implantable medical devices, such as stents, and methods for embedding agents in the polymer for controlled release, are known in the art and taught, for example, in U.S. Pat. Nos. 6,335,029; 6,322,847; 6,299,604; 6,290,722; 6,287,285; and 5,637,113. In some embodiments, the coating releases the inhibitor over a period of time, preferably over a period of days, weeks, or months. The particular polymer or other coating chosen is not a critical part of the present invention.

The methods of the invention are useful for slowing or inhibiting the stenosis or restenosis of natural and synthetic vascular grafts. As noted above in connection with stents, desirably, the synthetic vascular graft comprises a material which releases a compound of the invention over time to slow or inhibit VSM proliferation and the consequent stenosis of the graft. Hemodialysis grafts are a particular embodiment.

In addition to these uses, the methods of the invention can be used to slow or to inhibit stenosis or restenosis of blood vessels of persons who have had a heart attack, or whose test results indicate that they are at risk of a heart attack.

In one group of embodiments, compounds of the invention are administered to reduce proliferation of VSM cells in persons who do not have hypertension. In another group of embodiments, compounds of the invention are used to reduce proliferation of VSM cells in persons who are being treated for hypertension, but with an agent that is not an sEH inhibitor.

The compounds of the invention can be used to interfere with the proliferation of cells which exhibit inappropriate cell cycle regulation. In one important set of embodiments, the cells are cells of a cancer. The proliferation of such cells can be slowed or inhibited by contacting the cells with a compound of the invention. The determination of whether a particular compound of the invention can slow or inhibit the proliferation of cells of any particular type of cancer can be determined using assays routine in the art.

In addition to the use of the compounds of the invention, the levels of EETs can be raised by adding EETs. VSM cells contacted with both an EET and a compound of the invention exhibited slower proliferation than cells exposed to either the EET alone or to the a compound of the invention alone. Accordingly, if desired, the slowing or inhibition of VSM cells of a compound of the invention can be enhanced by adding an EET along with a compound of the invention. In the case of stents or vascular grafts, for example, this can conveniently be accomplished by embedding the EET in a coating along with a compound of the invention so that both are released once the stent or graft is in position.

D. Methods of Inhibiting the Progression of Obstructive Pulmonary Disease, Interstitial Lung Disease, or Asthma:

Chronic obstructive pulmonary disease, or COPD, encompasses two conditions, emphysema and chronic bronchitis, which relate to damage caused to the lung by air pollution, chronic exposure to chemicals, and tobacco smoke. Emphysema as a disease relates to damage to the alveoli of the lung, which results in loss of the separation between alveoli and a consequent reduction in the overall surface area available for gas exchange. Chronic bronchitis relates to irritation of the bronchioles, resulting in excess production of mucin, and the consequent blocking by mucin of the airways leading to the alveoli. While persons with emphysema do not necessarily have chronic bronchitis or vice versa, it is common for persons with one of the conditions to also have the other, as well as other lung disorders.

Some of the damage to the lungs due to COPD, emphysema, chronic bronchitis, and other obstructive lung disorders can be inhibited or reversed by administering inhibitors of the enzyme known as soluble epoxide hydrolase, or "sEH". The effects of sEH inhibitors can be increased by also administering EETs. The effect is at least additive over administering the two agents separately, and may indeed be synergistic.

The studies reported herein show that EETs can be used in conjunction with sEH inhibitors to reduce damage to the lungs by tobacco smoke or, by extension, by occupational or environmental irritants. These findings indicate that the co-administration of sEH inhibitors and of EETs can be used to inhibit or slow the development or progression of COPD, emphysema, chronic bronchitis, or other chronic obstructive lung diseases which cause irritation to the lungs.

Animal models of COPD and humans with COPD have elevated levels of immunomodulatory lymphocytes and neutrophils. Neutrophils release agents that cause tissue damage and, if not regulated, will over time have a destructive effect. Without wishing to be bound by theory, it is believed that reducing levels of neutrophils reduces tissue damage contributing to obstructive lung diseases such as COPD, emphysema, and chronic bronchitis. Administration of sEH inhibitors to rats in an animal model of COPD resulted in a reduction in the number of neutrophils found in the lungs. Administration of EETs in addition to the sEH inhibitors also reduced neutrophil levels. The reduction in neutrophil levels in the presence of sEH inhibitor and EETs was greater than in the presence of the sEH inhibitor alone.

While levels of endogenous EETs are expected to rise with the inhibition of sEH activity caused by the action of the sEH inhibitor, and therefore to result in at least some improvement in symptoms or pathology, it may not be sufficient in all cases to inhibit progression of COPD or other pulmonary diseases. This is particularly true where the diseases or other factors have reduced the endogenous concentrations of EETs below those normally present in healthy individuals. Administration of exogenous EETs in conjunction with an sEH inhibitor is therefore expected to augment the effects of the sEH inhibitor in inhibiting or reducing the progression of COPD or other pulmonary diseases.

In addition to inhibiting or reducing the progression of chronic obstructive airway conditions, the invention also provides new ways of reducing the severity or progression of chronic restrictive airway diseases. While obstructive airway diseases tend to result from the destruction of the lung parenchyma, and especially of the alveoli, restrictive diseases tend to arise from the deposition of excess collagen in the parenchyma. These restrictive diseases are commonly referred to as "interstitial lung diseases", or "ILDs", and include conditions such as idiopathic pulmonary fibrosis. The methods, compositions and uses of the invention are useful for reducing the severity or progression of ILDs, such as idiopathic pulmonary fibrosis. Macrophages play a significant role in stimulating interstitial cells, particularly fibroblasts, to lay down collagen. Without wishing to be bound by theory, it is believed that neutrophils are involved in activating macrophages, and that the reduction of neutrophil levels found in the studies reported herein demonstrates that the methods and uses of the invention will also be applicable to reducing the severity and progression of ILDs.

In some embodiments, the ILD is idiopathic pulmonary fibrosis. In other embodiments, the ILD is one associated with an occupational or environmental exposure. Exemplars of such ILDs, are asbestosis, silicosis, coal worker's pneumoconiosis, and berylliosis. Further, occupational exposure to any of a number of inorganic dusts and organic dusts is believed to be associated with mucus hypersecretion and respiratory disease, including cement dust, coke oven emissions, mica, rock dusts, cotton dust, and grain dust (for a more complete list of occupational dusts associated with these conditions, see Table 254-1 of Speizer, "Environmental Lung Diseases," Harrison's Principles of Internal Medicine, infra, at pp. 1429-1436). In other embodiments, the ILD is sarcoidosis of the lungs. ILDs can also result from radiation in medical treatment, particularly for breast cancer, and from connective tissue or collagen diseases such as rheumatoid arthritis and systemic sclerosis. It is believed that the methods, uses and compositions of the invention can be useful in each of these interstitial lung diseases.

In another set of embodiments, the invention is used to reduce the severity or progression of asthma. Asthma typically results in mucin hypersecretion, resulting in partial airway obstruction. Additionally, irritation of the airway results in the release of mediators which result in airway obstruction. While the lymphocytes and other immunomodulatory cells recruited to the lungs in asthma may differ from those recruited as a result of COPD or an ILD, it is expected that the invention will reduce the influx of immunomodulatory cells, such as neutrophils and eosinophils, and ameliorate the extent of obstruction. Thus, it is expected that the administration of sEH inhibitors, and the administration of sEH inhibitors in combination with EETs, will be useful in reducing airway obstruction due to asthma.

In each of these diseases and conditions, it is believed that at least some of the damage to the lungs is due to agents released by neutrophils which infiltrate into the lungs. The presence of neutrophils in the airways is thus indicative of continuing damage from the disease or condition, while a reduction in the number of neutrophils is indicative of reduced damage or disease progression. Thus, a reduction in the number of neutrophils in the airways in the presence of an agent is a marker that the agent is reducing damage due to the disease or condition, and is slowing the further development of the disease or condition. The number of neutrophils present in the lungs can be determined by, for example, bronchoalveolar lavage.

E. Prophylatic and Therapeutic Methods to Reduce Stroke Damage

Inhibitors of soluble epoxide hydrolase ("sEH") and EETs administered in conjunction with inhibitors of sEH have been shown to reduce brain damage from strokes. Based on these results, we expect that inhibitors of sEH taken prior to an ischemic stroke will reduce the area of brain damage and will likely reduce the consequent degree of impairment. The reduced area of damage should also be associated with a faster recovery from the effects of the stroke.

While the pathophysiologies of different subtypes of stroke differ, they all cause brain damage. Hemorrhagic stroke differs from ischemic stroke in that the damage is largely due to compression of tissue as blood builds up in the confined space within the skull after a blood vessel ruptures, whereas in ischemic stroke, the damage is largely due to loss of oxygen supply to tissues downstream of the blockage of a blood vessel by a clot. Ischemic strokes are divided into thrombotic strokes, in which a clot blocks a blood vessel in the brain, and embolic strokes, in which a clot formed elsewhere in the body is carried through the blood stream and blocks a vessel there. But, in both hemorrhagic stroke and ischemic stroke, the damage is due to the death of brain cells. Based on the results observed in our studies, however, we would expect at least some reduction in brain damage in all types of stroke and in all subtypes.

A number of factors are associated with an increased risk of stroke. Given the results of the studies underlying the present invention, sEH inhibitors administered to persons with any one or more of the following conditions or risk factors: high blood pressure, tobacco use, diabetes, carotid artery disease, peripheral artery disease, atrial fibrillation, transient ischemic attacks (TIAs), blood disorders such as high red blood cell counts and sickle cell disease, high blood cholesterol, obesity, alcohol use of more than one drink a day for women or two drinks a day for men, use of cocaine, a family history of stroke, a previous stroke or heart attack, or being elderly, will reduce the area of brain damaged of a stroke. With respect to being elderly, the risk of stroke increases for every 10 years. Thus, as an individual reaches 60, 70, or 80, administration of sEH inhibitors has an increasingly larger potential benefit. As noted in the next section, the administration of EETs in combination with one or more sEH inhibitors can be beneficial in further reducing the brain damage. One can expect beneficial effects from sEHI with or without EETs in a variety of diseases which lead to ischemia reperfusion injury such as heart attacks.

In some uses and methods, the sEH inhibitors and, optionally, EETs, are administered to persons who use tobacco, have carotid artery disease, have peripheral artery disease, have atrial fibrillation, have had one or more transient ischemic attacks (TIAs), have a blood disorder such as a high red blood cell count or sickle cell disease, have high blood cholesterol, are obese, use alcohol in excess of one drink a day if a woman or two drinks a day if a man, use cocaine, have a family history of stroke, have had a previous stroke or heart attack and do not have high blood pressure or diabetes, or are 60, 70, or 80 years of age or more and do not have hypertension or diabetes.

Clot dissolving agents, such as tissue plasminogen activator (TPA), have been shown to reduce the extent of damage from ischemic strokes if administered in the hours shortly after a stroke. TPA, for example, is approved by the FDA for use in the first three hours after a stroke. Thus, at least some of the brain damage from a stroke is not instantaneous, but occurs over a period of time or after a period of time has elapsed after the stroke. It is therefore believed that administration of sEH inhibitors, optionally with EETs, can also reduce brain damage if administered within 6 hours after a stroke has occurred, more preferably within 5, 4, 3, or 2 hours after a stroke has occurred, with each successive shorter interval being more preferable. Even more preferably, the inhibitor or inhibitors are administered 2 hours or less or even 1 hour or less after the stroke, to maximize the reduction in brain damage. Persons of skill are well aware of how to make a diagnosis of whether or not a patient has had a stroke. Such determinations are typically made in hospital emergency rooms, following standard differential diagnosis protocols and imaging procedures.

In some uses and methods, the sEH inhibitors and, optionally, EETs, are administered to persons who have had a stroke within the last 6 hours who: use tobacco, have carotid artery disease, have peripheral artery disease, have atrial fibrillation, have had one or more transient ischemic attacks (TIAs), have a blood disorder such as a high red blood cell count or sickle cell disease, have high blood cholesterol, are obese, use alcohol in excess of one drink a day if a woman or two drinks a day if a man, use cocaine, have a family history of stroke, have had a previous stroke or heart attack and do not have high blood pressure or diabetes, or are 60, 70, or 80 years of age or more and do not have hypertension or diabetes.

The conditions of therapeutic administration for all of these indications are as described above.

F. Methods of Treating Cancer

The compounds and compositions of the present invention are also useful in the treatment of cancer. The compounds of formula I can possess anti-proliferative activity and are therefore useful in the treatment of proliferative disorders such as cancers, leukaemias and other disorders associated with uncontrolled cellular proliferation such as psoriasis and restenosis. As defined herein, an anti-proliferative effect within the scope of the present invention may be demonstrated by the ability to inhibit cell proliferation in an in vitro whole cell assay, for example using any of the cell lines A549, HT29, Saos-2, HeLa or MCF-7, or by showing inhibition of a CDK enzyme (such as CDK2 or CDK4) in an appropriate assay. Using such cell line and enzymes assays it may be determined whether a compound is anti-proliferative in the context of the present invention.

As used herein, the term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia. One of skill in the art will appreciate that other cancers and proliferative disorders can be treated by the compounds and compositions of the present invention.

In some embodiments, the cancer is bone cancer, colon cancer, multiple myeloma, gastric cancer, colorectal cancer, prostate cancer, cervical cancer, lung cancer, pancreatic cancer, medulloblastoma, kidney cancer, liver cancer, parathyroid cancer, endometrial cancer, or breast cancer.

G. Kinase Inhibition

The methods of the present invention also include inhibition of a kinase. Any kinase can be inhibited using the compounds of the present invention. For example, the kinases Raf-1 and b-Raf, among others, can be inhibited by the compounds of the present invention.

In another aspect of the invention, the compounds of the invention can reduce the onset of cancer (carcinogenesis), primary tumor growth (cancer proliferation), and/or tumor progression (metastasis). With the advent of more complete knowledge of the molecular biology of cancer, new therapies have recently been designed which target mechanisms by which the disease escapes standard therapy. For example, the multi-kinase and VEGF-receptor inhibitors, such as sorafenib and sunitinib, interrupt the pathway by which angiogenesis becomes established and promulgated resulting in inadequate nourishment of metastatic disease thereby leading to a higher degree of treatment success. In certain malignancies, such as kidney cancer whose mechanism of oncogenesis generally involves disrupted hypoxia pathways and thus is highly angiogenic, these agents have had the effect of revolutionizing treatment. The recently described X ray-crystal structure of B-Raf complexed with sorafenib, a structural similarity between this drug and the class of urea-based compounds that inhibit the soluble epoxide hydrolase (sEH) was noted. The sEH converts epoxyeicosatrienoic acids (EETs) to the less active dihydroxyeicosatrienoic acids (DHETs). EETs are potently anti-inflammatory through mediating the nuclear factor kappa B (NF-κB) and IκB kinase system. The sEH inhibitors have been shown to stabilize the EET levels and thus have beneficial effects on hypertension, nociception, atherosclerosis, and inflammation through increasing endogenous levels of EETs and other lipid epoxides. Herein, this invention proposes that the simultaneous inhibition of sEH with kinases will therefore be an effective treatment for cancer.

In some embodiments, the present invention provides a method of treating cancer, the method including administering to a subject in need thereof, a therapeutically effective amount of a compound of the present invention, thereby treating cancer.

In other embodiments, the present invention provides a method of treating cancer, the method including contacting cancer cells with a therapeutically effective amount of a compound of the present invention, thereby treating cancer. The contacting step can be performed either in vitro or in vivo. In some embodiments, the contacting is performed in vitro.

VII. Assays

Additionally, the present invention provides a variety of assays and associated methods for monitoring soluble epoxide hydrolase activity and a kinase, particularly the activity that has been modulated by the administration of one or more of the compounds provided above.

In one group of embodiments, the invention provides methods for reducing the formation of a biologically active diol produced by the action of a soluble epoxide hydrolase, the method comprising contacting the soluble epoxide hydrolase with an amount of a compound of the present invention, sufficient to inhibit the activity of the soluble epoxide hydrolase and reduce the formation of the biologically active diol.

In another group of embodiments, the invention provides methods for stabilizing biologically active epoxides in the presence of a soluble epoxide hydrolase, the method comprising contacting the soluble epoxide hydrolase with an amount of a compound of the present invention, sufficient to inhibit the activity of the soluble epoxide hydrolase and stabilize the biologically active epoxide.

In another group of embodiments, the invention provides methods for inhibiting the phosphorylation activity of kinases, the method comprising contacting the kinase with an amount of a compound of the present invention, sufficient to inhibit the activity of the kinase and the corresponding biological events.

In each of these groups of embodiments, the methods can be carried out as part of an in vitro assay or the methods can be carried out in vivo by monitoring blood titers of the respective biologically active epoxide or diol.

Epoxides and diols of some fatty acids are biologically important chemical mediators and are involved in several biological processes. The strongest biological data support the action of oxylipins as chemical mediators between the vascular endothelium and vascular smooth muscle. Epoxy lipids are anti-inflammatory and anti-hypertensive. Additionally, the lipids are thought to be metabolized by beta-oxidation, as well as by epoxide hydration. The soluble epoxide hydrolase is considered to be the major enzyme involved in the hydrolytic metabolism of these oxylipins. The compounds of the present invention can inhibit the epoxide hydrolase and stabilize the epoxy lipids both in vitro and in vivo. This activity results in a reduction of hypertension in four separate rodent models. Moreover, the inhibitors show a reduction in renal inflammation associated with and independent of the hypertensive models.

The compounds of the present invention can be screened using a variety of assays, such as a kinase assay, a cell-based assay or a sEH assay (Jones, P. D.; Wolf, N. M.; Morisseau, C.; Whetstone, P.; Hock, B.; Hammock, B. D. Anal. Biochem. 343:66-75; 2005).

The kinase-based assay can be performed using any kinase known, such as Raf-1 or b-Raf, among others. Any suitable substrate can also be used, such as MEK1. The assay can be performed using luminescence as the detection method.

The cell-based assay can be performed using any suitable cell line, such as HepG2 hepatoma cell line. The cells are placed in suitable a medium, such as fetal bovine serum, with an optional antibiotic such as penicillin-streptomycin. The cells are plated, and the inhibitors added at specific concentrations. Cell viability can be determined at any time after contact with the inhibitors, such as 72 hours. Cellular proliferation can be determined using any method known in the art, including colorimetric methods.

Further analysis of kinase inhibition can be performed by immunoprecipitation or immunobloting using an appropriate phospho-antibody which recognizes the target kinase.

The following examples are provided to illustrate the invention and are not intended to limit any aspect of the invention as set forth above or in the claims below.

VIII. Examples

All reagents and solvents were obtained from commercial suppliers and were used without further purification. All reactions, unless otherwise described, were performed under an inert atmosphere of dry nitrogen. Melting points were determined on an OptiMelt melting point apparatus and are uncorrected. $^1$H NMR and $^{13}$C NMR spectra were recorded at 300 and 75 MHz, respectively. Elemental analyses were determined at Midwest Microlab, Indianapolis, Ind. Microwave reactions were performed in an ETHOS SEL labstation (Milestone Inc., Shelton, Conn.). Mass spectra were measured by LC-MS equipped with a Waters 2790 and a Waters PDA 996 using electrospray (+) ionization. Flash chromatography was performed on silica gel.

Example 1

Preparation of cis-4-{4-[3-(4-Trifluoromethoxy-phenyl)-ureido]-cyclohexyloxy}-benzoic acid (1686)

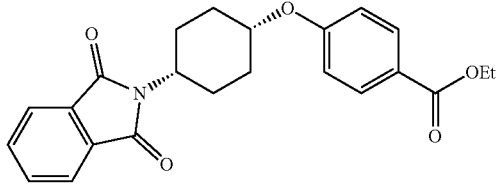 [SMILES: CCOC(=O)c1ccc(O[C@H]2CC[C@@H](N3C(=O)c4ccccc4C3=O)CC2)cc1]

cis-4-[4-(1,3-Dioxo-1,3-dihydro-isoindol-2-yl)-cyclohexyloxy]-benzoic acid ethyl ester (14f)

Compound 14f was prepared in 78% yield from trans-2-(4-hydroxy-cyclohexyl)-isoindole-1,3-dione using the procedure detailed for compound 5 in Example 13. $^1$H NMR (CDCl$_3$): δ 8.00 (d, J=9 Hz, 2H), 7.86-7.65 (m, 4H), 7.01 (d, J=9 Hz, 2H), 4.73-4.65 (m, 1H), 4.34 (q, J=7 Hz, 2H), 4.28-4.15 (m, 1H), 2.80-2.62 (m, 2H), 2.28-2.17 (m, 2H), 1.75-1.52 (m, 2H), 1.38 (t, J=7 Hz, 3H).

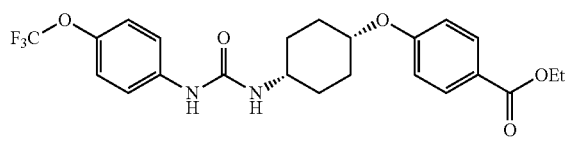 [SMILES: CCOC(=O)c1ccc(O[C@H]2CC[C@@H](NC(=O)Nc3ccc(OC(F)(F)F)cc3)CC2)cc1]

cis-4-{4-[3-(4-Trifluoromethoxy-phenyl)-ureido]-cyclohexyloxy}-benzoic acid ethyl ester (19b)

Anhydrous hydrazine (0.17 mL, 5.3 mmol) was added to a solution of compound 14f (1 g, 2.6 mmol) in 20 mL of CH$_2$Cl$_2$ followed by MeOH (20 mL) at room temperature. The reaction mixture was allowed to stir for 1 d. The resulting white precipitates were filtered off and the solvent was removed in vacuo. The resulting white solids were dissolved in aqueous 1N HCl solution and washed with CH$_2$Cl$_2$. The aqueous layer was basified with excess 1N NaOH solution and then extracted with CH$_2$Cl$_2$. After drying with MgSO$_4$, the solvent was evaporated affording crude amine, which was used in the next step without further purification. To a solution of crude amine in DMF (50 mL) was added 4-(trifluoromethoxy)phenyl isocyanate (1.1 g, 4.3 mmol) followed by triethylamine (0.74 mL, 5.3 mmol) at 0° C. The reaction mixture was stirred overnight. The reaction mixture was poured into water, and the resulting precipitates were collected and washed with water. The crude product was purified by column chromatography to give the titled compound (1.7 g, 85%) as a white solid. $^1$H NMR (CDCl$_3$): δ 7.98 (d, J=9 Hz, 2H), 7.35 (d, J=9 Hz, 2H), 7.13 (d, J=9 Hz, 2H), 6.87 (d, J=9 Hz, 2H), 6.85 (s, 1H), 5.01 (d, J=8 Hz, 1H), 4.57-4.51 (m, 1H), 4.36 (q, J=7 Hz, 2H), 3.89-3.72 (m, 1H), 2.07-1.52 (m, 8H), 1.39 (t, J=7 Hz, 3H). MS (ESI) m/z: 467.2 (M+H$^+$).

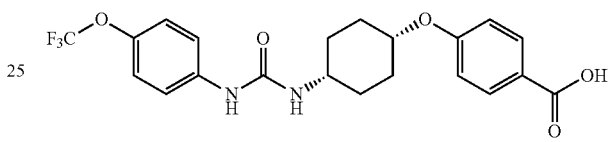

cis-4-{4-[3-(4-Trifluoromethoxy-phenyl)-ureido]-cyclohexyloxy}-benzoic acid (1686)

To a solution of 19b (0.1 g, 0.21 mmol) in 5 mL of CH$_3$CN was added lithium hydroxide (15.4 mg, 0.64 mmol) followed by 2 mL of water at room temperature. The reaction mixture was stirred overnight. The solvent was evaporated in vacuo and washed with EtOAc. The aqueous layer was acidified with 1N HCl to give white precipitates. The resulting white solids were collected by suction filtration and washed with water. The crude product was recrystallized from MeOH to give the titled compound (0.84 g, 90%) as a white solid. mp 210-212° C. $^1$H NMR (DMSO-d$_6$): δ 12.60 (s, 1H), 8.48 (s, 1H), 7.87 (d, J=8 Hz, 1H), 7.47 (d, J=9 Hz, 1H), 7.21 (d, J=9 Hz, 1H), 7.03 (d, J=8 Hz, 1H), 6.35 (d, J=8 Hz, 1H), 4.66-4.57 (m, 1H), 3.73-3.60 (m, 1H), 1.87-1.50 (m, 1H). $^{13}$C NMR (DMSO-d$_6$): □ 167.04, 160.90, 154.36, 141.99, 139.84, 131.48, 122.77, 121.67, 118.57, 115.28, 71.95, 45.66, 27.71, 27.36. MS (ESI) m/z: 439.1 (M+H$^+$). Anal. Calcd for C$_{21}$H$_{21}$F$_3$N$_2$O$_5$: C, 57.53; H, 4.83; N, 6.39. Found: C, 57.33; H, 4.81; N, 6.29.

Example 2

Preparation of trans-4-{4-[3-(4-Trifluoromethoxy-phenyl)-ureido]-cyclohexyloxy}-benzoic acid (1728)

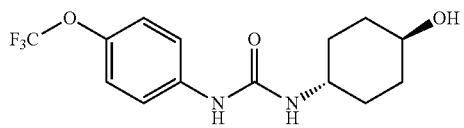 [SMILES: O=C(Nc1ccc(OC(F)(F)F)cc1)N[C@H]1CC[C@H](O)CC1]

trans-1-(4-Hydroxy-cyclohexyl)-3-(4-trifluoromethoxy-phenyl)-urea

To a solution of 4-(trifluoromethoxy)phenyl isocyanate (2 g, 9.8 mmol) in DMF (100 mL) were added trans-4-aminocyclohexanol hydrochloride (1.6 g, 10.8 mmol) and Et$_3$N (1.5 mL, 10.8 mmol) at 0° C. The reaction mixture was warmed up to room temperature and stirred overnight. After adding aq 1N HCl (20 mL) and water (100 mL), the resulting white precipitates were collected by suction filtration. The collected solid was thoroughly washed with water. Recrystallization from acetone at −78° C. afforded 2.4 g (70%) of the title compound as a white solid. mp 224.1-225.3° C. $^1$H NMR (300 MHz, DMSO-d$_6$; δ 8.50 (s, 1H), 7.45 (d, J=9 Hz, 2H), 7.21 (d, J=9 Hz, 2H), 6.06 (d, J=8 Hz, 1H), 4.55 (d, J=4 Hz, 1H), 3.44-3.33 (m, 2H), 1.91-1.68 (m, 4H), 1.31-1.07 (m, 4H).

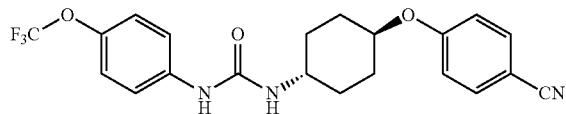 [SMILES: N#Cc1ccc(O[C@H]2CC[C@H](NC(=O)Nc3ccc(OC(F)(F)F)cc3)CC2)cc1]

trans-1-[4-(4-Cyano-phenoxy)-cyclohexyl]-3-(4-trifluoromethoxy-phenyl)-urea (2581)

To a solution of the above compound (2.5 g, 7.9 mol) in DMF (70 mL) was added 60% sodium hydride in oil (0.25 g, 10.2 mol) portionwise at 0° C. After 10 min, 4-fluorobenzonitrile (1.1 g, 8.6 mol) was added. The reaction mixture was allowed to slowly warm to room temperature overnight. The reaction was quenched by adding water and the resulting white precipitates were collected and washed with water and hexanes. The resulting solid was purified by recrystallization with MeOH/water to give 3.1 g (94%) as a white solid. mp: 186.5-189.2° C. $^1$H NMR (DMSO-d$_6$): δ 8.51 (s, 1H), 7.75 (d, J=9 Hz, 2H), 7.47 (d, J=9 Hz, 2H), 7.22 (d, J=9 Hz, 2H), 7.13 (d, J=9 Hz, 2H), 6.21 (d, J=8 Hz, 1H), 4.58-4.42 (m, 1H), 3.61-3.45 (m, 1H), 2.13-1.87 (m, 4H), 1.58-1.28 (m, 4H).

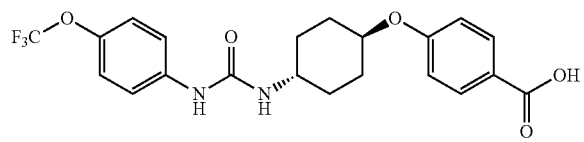 [SMILES: O=C(Nc1ccc(OC(F)(F)F)cc1)N[C@H]1CC[C@H](Oc2ccc(C(=O)O)cc2)CC1]

trans-4-{4-[3-(4-Trifluoromethoxy-phenyl)-ureido]-cyclohexyloxy}-benzoic acid (1728)

To a solution of the above compound (2.3 g, 5.5 mol) in EtOH (50 mL) was added 6N NaOH solution (32 mL) at room temperature. The reaction mixture was gently heated up to 90° C. and stirred for 18 h. The reaction mixture was acidified with conc HCl at 0° C. After evaporating ethanol, the resulting precipitates were filtered and washed with water. The crude solid was decolorized with activated charcoal in hot MeOH. The resulting crude solid was recrystallized with MeOH/water to give the titled compound (2.1 g, 86% yield).

mp 244-273° C. $^1$H NMR (300 MHz, DMSO-d6): δ 12.59 (s, 1H), 8.51 (s, 1H), 7.86 (d, J=9 Hz, 1H), 7.47 (d, J=9 Hz, 1H), 7.22 (d, J=9 Hz, 1H), 7.03 (d, J=9 Hz, 1H), 6.19 (d, J=9 Hz, 1H), 4.52-4.38 (m, 1H), 3.61-3.45 (m, 1H), 2.12-1.87 (m, 1H), 1.58-1.28 (m, 1H). $^{13}$C NMR (DMSO-d6): δ 167.07, 161.10, 154.47, 141.98, 139.87, 131.43, 122.74, 121.69, 118.55, 115.10, 74.31, 47.17, 30.01, 29.66. Anal. Calcd for C$_{21}$H$_{21}$F$_3$N$_2$O$_5$: C, 57.53; H, 4.83; N, 6.39. Found: C, 57.41; H, 4.81; N, 6.39.

Example 3

Preparation of trans-4-{4-[3-(4-Chloro-phenyl)-ureido]-cyclohexyloxy}-benzoic acid (2084)

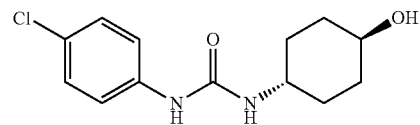 [SMILES: O=C(Nc1ccc(Cl)cc1)N[C@H]1CC[C@H](O)CC1]

trans-1-(4-Chloro-phenyl)-3-(4-hydroxy-cyclohexyl)-urea was prepared in 78% yield from 4-chlorophenyl isocyanates using the procedure detailed for compound 07086 in Example 4. $^1$H NMR (300 MHz, DMSO-d$_6$): δ 8.43 (s, 1H), 7.38 (d, J=9 Hz, 2H), 7.24 (d, J=9 Hz, 2H), 6.04 (d, J=8 Hz, 1H), 4.54 (d, J=4 Hz, 1H), 3.46-3.28 (m, 2H), 1.92-1.70 (m, 4H), 1.30-1.07 (m, 4H).

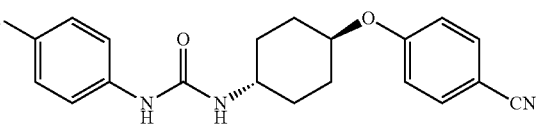

trans-1-(4-Chloro-phenyl)-3-[4-(4-cyano-phenoxy)-cyclohexyl]-urea (2580) was prepared in 90% yield from trans-1-(4-chloro-phenyl)-3-(4-hydroxy-cyclohexyl)-urea using the procedure detailed for compound 2182 in Example 4. $^1$H NMR (300 MHz, DMSO-d$_6$): δ 8.44 (s, 1H), 7.74 (d, J=8 Hz, 2H), 7.39 (d, J=9 Hz, 2H), 7.25 (d, J=9 Hz, 2H), 7.12 (d, J=8 Hz, 2H), 6.19 (d, J=8 Hz, 1H), 4.59-4.42 (m, 1H), 3.61-3.44 (m, 1H), 2.13-1.86 (m, 4H), 1.58-1.27 (m, 4H).

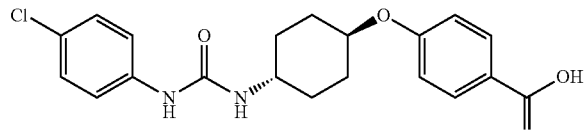

trans-4-{4-[3-(4-Chloro-phenyl)-ureido]-cyclohexyloxy}-benzoic acid (2084)

Compound 2084 was prepared in 82% yield from trans-1-(4-chloro-phenyl)-3-[4-(4-cyano-phenoxy)-cyclohexyl]-urea using the procedure using compound 2182 detailed in Example 4. $^1$H NMR (300 MHz, DMSO-d$_6$) δ 8.68 (s, 1H), 7.86 (d, J=8 Hz, 1H), 7.42 (d, J=8 Hz, 1H), 7.25 (d, J=8 Hz, 1H), 7.00 (d, J=8 Hz, 1H), 6.38 (d, J=7 Hz, 1H), 4.54-4.35 (m, 1H), 3.62-3.41 (m, 1H), 2.15-1.80 (m, 1H), 1.59-1.27 (m, 1H).

Example 4

Preparation of trans-4-{4-[3-(4-Chloro-3-trifluoromethyl-phenyl)-ureido]-cyclohexyloxy}-benzoic acid (2221)

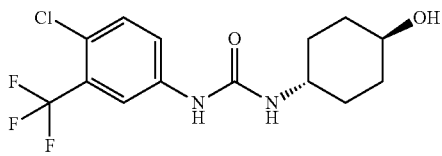 [SMILES: O=C(Nc1ccc(Cl)c(C(F)(F)F)c1)N[C@H]1CC[C@H](O)CC1]

trans-1-(4-Chloro-3-trifluoromethyl-phenyl)-3-(4-hydroxy-cyclohexyl)-urea (07086)

To a solution of 4-chloro-3-(trifluoromethyl)phenyl isocyanate (5 g, 22.6 mmol) in DMF (35 mL) were added trans-4-aminocyclohexanol hydrochloride (3.8 g, 24.8 mmol) and Et₃N (3.5 mL, 24.8 mmol) at 0° C. The reaction mixture was warmed up to room temperature and stirred overnight. After adding 1N HCl (40 mL) and water, the resulting white precipitates were collected by suction filtration. The collected solid was thoroughly washed with water. White powers collected were dissolved in EtOH (200 mL) then aqueous 30% NaOH (25 mL) was added. The reaction mixture was refluxed overnight. EtOH was removed in vacuo. The precipitates were filtered and washed with water. Recrystallization from methanol afforded 9.5 g (42%) of the title compound as a white solid. Mp: 239.5-241.1° C. NMR (DMSO-d₆): δ 8.79 (s, 1H), 8.06 (d, J=2 Hz, 1H), 7.55-7.47 (m, 2H), 6.20 (d, J 8 Hz, 1H), 4.54 (d, J=4 Hz, 1H), 3.45-3.34 (m, 2H), 1.86-1.75 (m, 4H), 1.28-1.11 (m, 4H).

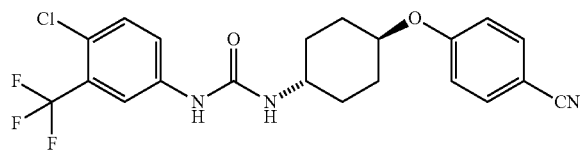

trans-1-(4-Chloro-3-trifluoromethyl-phenyl)-3-[4-(4-cyano-phenoxy)-cyclohexyl]-urea (2182)

To a solution of 07086 (1.35 g, 4 mmol) in DMF (40 mL) was added 60% sodium hydride in oil (0.24 g, 6 mmol) portionwise at 0° C. After 10 min, 4-fluorobenzonitrile (0.73 g, 6 mmol) was added. The reaction mixture was allowed to slowly warm to room temperature overnight. The reaction was quenched by adding water and the resulting white precipitates were collected and washed with water. The collected solid was recrystallized from methanol to give the title compound, 1.5 g (86%) as a white solid. ¹H NMR (300 MHz, DMSO-d₆): δ 8.83-8.78 (s, 1H), 8.08 (d, J=2 Hz, 1H), 7.75 (d, J=9 Hz, 2H), 7.57-7.47 (m, 2H), 7.13 (d, J=9 Hz, 2H), 6.37 (d, J=7 Hz, 1H), 4.55-4.41 (m, 1H), 3.62-3.43 (m, 1H), 2.15-1.83 (m, 4H), 1.60-1.30 (m, 4H).

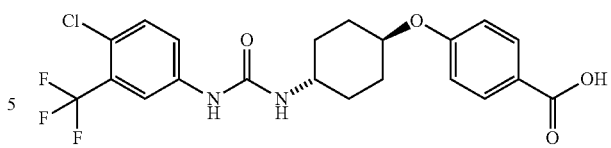

To a solution of 2182 (0.27 g, 0.62 mmol) in EtOH (10 mL) was added 6N NaOH solution (3.6 mL) at room temperature. The reaction mixture was gently heated up to 80° C. and stirred for 18 h. The reaction mixture was acidified with conc. HCl at 0° C. After evaporating ethanol, the resulting precipitates were filtered and washed with water. The crude solid was recrystallized from EtOH to give the title compound (0.23 g, 82% yield) as a white solid. ¹H NMR (300 MHz, DMSO-d₆): δ 12.60 (s, 1H), 8.80 (s, 1H), 8.09-8.06 (m, 1H), 7.86 (d, J=9 Hz, 2H), 7.55-7.51 (m, 2H), 7.03 (d, J=9 Hz, 2H), 6.35 (d, J=8 Hz, 1H), 4.52-4.38 (m, 1H), 3.62-3.45 (m, 1H), 2.14-1.85 (m, 4H), 1.58-1.30 (m, 4H).

Example 5

Preparation of trans-N-Methyl-4-{4-[3-(4-trifluoromethoxy-phenyl)-ureido]-cyclohexyloxy}-benzamide (2227)

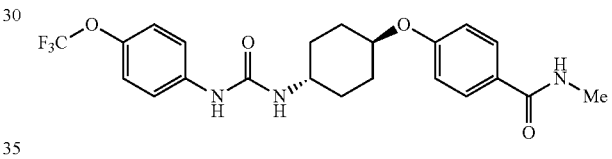

To a solution of 1728 (0.22 g, 0.5 mmol), EDC HCl (0.12 g, 0.63 mmol), HOBT (0.09 g, 0.63 mmol), TEA (0.17 mL, 0.63 mmol) in THF (10 mL) was added 2M MeNH₂ in THF (1.25 mL, 2.5 mmol) at 0° C. The reaction mixture was allowed to slowly warm to room temperature overnight. The solvent was removed in vacuo and then purified by recrystallization with EtOAc/Hexanes gave the title compound, 0.16 g (71%) as a white solid. 1H NMR (300 MHz, DMSO-d₆): δ 8.53 (s, 1H), 8.28 (q, J=4 Hz, 1H), 7.77 (d, J=9 Hz, 2H), 7.47 (d, J=9 Hz, 2H), 7.22 (d, J=9 Hz, 2H), 6.99 (d, J=9 Hz, 2H), 6.21 (d, J=8 Hz, 1H), 4.49-4.36 (m, 1H), 3.62-3.45 (m, 1H), 2.75 (d, J=4 Hz, 3H), 2.11-1.87 (m, 4H), 1.57-1.25 (m, 4H).

Example 6

Preparation of cis-N-Methyl-4-{4-[3-(4-trifluoromethoxy-phenyl)-ureido]-cyclohexyloxy}-benzamide (2228)

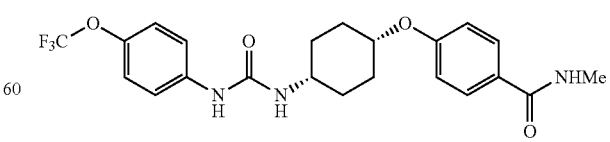

To a solution of 1686 (0.22 g, 0.5 mmol), EDC HCl (0.12 g, 0.63 mmol), HOBT (0.09 g, 0.63 mmol), TEA (0.17 mL, 0.63 mmol) in THF (10 mL) was added 2M MeNH₂ in THF (1.25 mL, 2.5 mmol) at 0° C. The reaction mixture was allowed to slowly warm to room temperature overnight. The solvent was removed in vacuo and then purified by recrystallization with EtOAc/Hexanes gave the title compound, 0.2 g (89%) as a white solid. mp 207.3-208.4° C. $^1$H NMR (300 MHz, DMSO-$d_6$): δ 8.55 (s, 1H), 8.26 (q, J=4 Hz, 1H), 7.78 (d, J=9 Hz, 2H), 7.47 (d, J=9 Hz, 2H), 7.21 (d, J=9 Hz, 2H), 7.00 (d, J=9 Hz, 2H), 6.40 (d, J=8 Hz, 1H), 4.62-4.53 (m, 1H), 3.73-3.60 (m, 1H), 2.75 (d, J=4 Hz, 3H), 1.89-1.50 (m, 8H).

Example 7

Preparation of trans-4-{4-[3-(4-Chloro-3-trifluoromethyl-phenyl)-ureido]-cyclohexyloxy}-N-methyl-benzamide (2253)

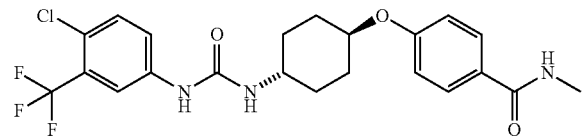

To a solution of 2221 from Example 4 (0.15 g, 0.33 mmol), EDC (0.093 g, 0.49 mmol), TEA (0.069 mL, 0.49 mmol) in THF (5 mL) was added 2M MeNH$_2$ in THF (1.6 mL, 3.2 mmol) at 0° C. The reaction mixture was allowed to slowly warm to room temperature overnight. The solvent was removed in vacuo and then purified by column chromatography (1:1 Hexanes-EtOAc) gave the title compound, 0.13 g (82%) as a white solid. $^1$H NMR (300 MHz, DMSO-$d_6$) δ 8.81 (s, 1H), 8.26 (q, J=4 Hz, 1H), 8.08 (d, J=2 Hz, 1H), 7.77 (d, J=9 Hz, 2H), 7.55-7.50 (m, 2H), 6.99 (d, J=9 Hz, 2H), 6.44-6.27 (m, 1H), 4.50-4.35 (m, 1H), 3.61-3.46 (m, 1H), 2.75 (d, J=4 Hz, 3H), 2.12-1.85 (m, 4H), 1.57-1.30 (m, 4H).

Example 8

Preparation of trans-4-{4-[3-(4-chloro-3-trifluoromethyl-phenyl)-ureido]-cyclohexyloxy}-pyridine-2-carboxylic acid methylamide (t-CUPM)(2278)

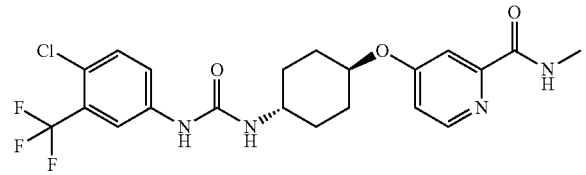 [SMILES: CNC(=O)c1cc(O[C@H]2CC[C@H](NC(=O)Nc3ccc(Cl)c(C(F)(F)F)c3)CC2)ccn1]

Compound 2280 (2.67 g, 5.2 mmol) was dissolved in 30% TFA in DCM (40 mL) at room temperature. The reaction mixture was stirred for 6 h and concentrated in vacuo. After adding Et$_2$O (60 mL), the resulting solid was filtered and washed with Et$_2$O to give the corresponding acid (2.56 g) in 86% yield as the TF salt. To the TF salt of the carboxylic acid (0.15 g, 0.26 mmol), EDC (0.10 g, 0.53 mmol), TEA (0.19 mL, 1.1 mmol) in THF (10 mL) was added 2M MeNH$_2$ in THF (1.3 mL, 2.6 mmol) at 0° C. After 6 h, same amount of methylamine was added at room temperature. The reaction mixture was allowed to slowly warm to room temperature overnight. The solvent was removed in vacuo and then purified by column chromatography (1:1 Hexanes-EtOAc) gave the title compound, 0.1 g (81%) as a white solid. $^1$H NMR (300 MHz, DMSO-$d_6$): δ 8.83 (s, 1H), 8.73 (q, J=5 Hz, 1H), 8.40 (d, J=6 Hz, 1H), 8.08 (d, J=1.81 Hz, 1H), 7.55-7.52 (m, 2H), 7.51 (d, J=3 Hz, 1H), 7.15 (dd, J=6 and 3 Hz, 1H), 6.36 (d, J=8 Hz, 1H), 4.66-4.54 (m, 1H), 3.62-3.48 (m, 1H), 2.80 (d, J=5 Hz, 3H), 2.12-1.87 (m, 4H), 1.60-1.34 (m, 4H). MS (ESI) m/z: 471.5 (M+H$^+$).

Example 9

Preparation of trans-4-{4-[3-(4-Chloro-3-trifluoromethyl-phenyl)-ureido]-cyclohexyloxy}-pyridine-2-carboxylic acid tert-butyl ester (2280)

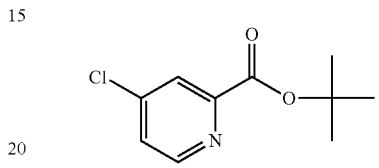

tert-Butyl 4-chloropicolinate

To thionyl chloride (40 mL) was added picolinic acid (10.5 g, 85.4 mmol) followed by sodium bromide (0.93 mg, 9.2 mmol) at room temperature. The reaction mixture was refluxed for 24 h. the reaction mixture was then cooled to room temperature and thionyl chloride was removed in vacuo. The residue was diluted with THF (50 mL) and concentrated to dryness. The compound was used for further reaction without purification. To a solution of t-butanol (19.6 mL), pyridine (20.7 mL) and 1,2-dichloroethane (80 mL) at 0° C., was added a solution of 4-chloropicolinyl chloride above in 1,2-dichloroethane (60 mL). The reaction mixture was heated at 50° C. for 24 h. The reaction mixture was diluted with DCM and then washed with 5% citric acid several times. The organic layer was dried over MgSO4 and concentrated. The residue was purified by column chromatography (30% EtOAc in hexanes) to give a colorless oil (6.6 g, 60.4%). $^1$H NMR (DMSO-$d_6$): δ 8.68 (d, J=5 Hz, 1H), 8.01 (d, J=2 Hz, 1H), 7.79 (dd, J=5 and 2 Hz, 1H), 1.56 (s, 9H).

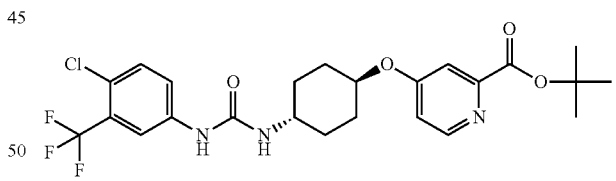

trans-4-{4-[3-(4-Chloro-3-trifluoromethyl-phenyl)-ureido]-cyclohexyloxy}-pyridine-2-carboxylic acid tert-butyl ester (2280)

To a solution of 07086 from Example 4 (0.38 g, 1.13 mmol) and tert-butyl 4-chloropicolinate (0.24 g, 1.13 mmol) in THF (12 mL) was added 1.0 M potassium tert-butoxide solution in THF (3.4 mL, 3.4 mmol) at 0° C. The reaction mixture was allowed to slowly warm to room temperature and then stirred overnight. The reaction was quenched by adding water and the resulting white precipitates were collected and washed with water. Purification by column chromatography (6:4 Hexanes-EtOAc) gave the title compound, 1.18 g (88%) as a yellowish powder. Mp: 100.7-116.6° C. $^1$H NMR (300 MHz, DMSO-d$_6$): δ 8.81 (s, 1H), 8.47 (d, J=6 Hz, 1H), 8.08 (d, J=2 Hz, 1H), 7.55-7.51 (m, 2H), 7.45 (d, J=3 Hz, 1H), 7.23 (dd, J=6 and 3 Hz, 1H), 6.37 (d, J=8 Hz, 1H), 4.66-4.50 (m, 1H), 3.63-3.48 (m, 1H), 2.13-1.87 (m, 4H), 1.53-1.35 (m, 4H), 1.54 (s, 9H). MS (ESI) m/z: 514.2 (M+H$^+$).

Example 10

Preparation of trans-1-(4-Chloro-3-trifluoromethyl-phenyl)-3-[4-(5-trifluoromethyl-pyridin-2-yloxy)-cyclohexyl]-urea (2288)

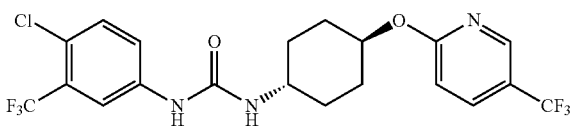 [SMILES: O=C(Nc1ccc(Cl)c(C(F)(F)F)c1)N[C@H]1CC[C@H](Oc2ccc(C(F)(F)F)cn2)CC1]

To a solution of 07086 from Example 4 (0.17 g, 0.5 mmol) in DMF (5 mL) was added 60% sodium hydride in oil (0.03 g, 0.75 mmol) portionwise at 0° C. After 10 min, 2-chloro-5-(trifluoromethyl)pyridine (0.14 g, 0.75 mmol) was added. The reaction mixture was allowed to slowly warm to room temperature overnight. The reaction was quenched by adding water and the resulting white precipitates were collected and washed with water. The collected solid was recrystallized from methanol to give the title compound, 0.2 g (83%) as a white solid. mp 176.5-177.9° C. $^1$H NMR (300 MHz, DMSO-d$_6$): δ 8.82 (s, 1H), 8.58-8.54 (m, 1H), 8.08-8.06 (m, 1H), 8.04 (dd, J=9 and 3 Hz, 1H), 7.54-7.52 (m, 2H), 6.96 (d, J=9 Hz, 1H), 6.30 (d, J=8 Hz, 1H), 5.13-4.99 (m, 1H), 3.64-3.48 (m, 1H), 2.15-1.89 (m, 4H), 1.63-1.30 (m, 4H).

Example 11

Preparation of trans-5-{4-[3-(4-Chloro-3-trifluoromethyl-phenyl)-ureido]-cyclohexyloxy}-pyridine-2-carboxylic acid tert-butyl ester (2315)

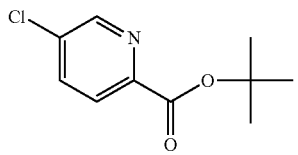

5-Chloro-pyridine-2-carboxylic acid tert-butyl ester

To a solution of 5-chloropyridine-2-carboxylic acid (4 g, 25.4 mmol) in acetonitrile (250 mL) were added DMAP (0.3 g, 2.54 mmol) and TEA (5.3 mL, 38.1 mmol) at 0° C. followed by a solution of Boc$_2$O (8.3 g, 38.1 mmol) in acetonitrile (50 mL). The resulting light brown solution was warmed up to room temperature and stirred overnight. The solvent was removed in vacuo to afford a white solid which was purified by column chromatography (4:1 Hexanes: EtOAc) to give a white solid (4.5 g, 83% yield). mp 86.3-88.3° C. $^1$H NMR (300 MHz, DMSO-d$_6$: δ 8.75 (dd, J=2 and 1 Hz, 1H), 8.11 (dd, J=8 and 2 Hz, 1H), 8.00 (dd, J=8 Hz, 1H), 1.55 (s, 9H).

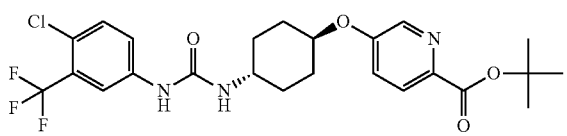 [SMILES: CC(C)(C)OC(=O)c1ccc(O[C@H]2CC[C@H](NC(=O)Nc3ccc(Cl)c(C(F)(F)F)c3)CC2)cn1]

trans-5-{4-[3-(4-Chloro-3-trifluoromethyl-phenyl)-ureido]-cyclohexyloxy}-pyridine-2-carboxylic acid tert-butyl ester (2315)

To a solution of 07086 from Example 4 (0.38 g, 1.13 mmol) and 5-chloro-pyridine-2-carboxylic acid tert-butyl ester (0.32 g, 1.5 mmol) in THF (12 mL) was added 1.0 M potassium tert-butoxide solution in THF (3 mL, 3 mmol) at 0° C. The reaction mixture was allowed to slowly warm to room temperature and then stirred overnight. The reaction was quenched by adding water and the resulting white precipitates were collected and washed with water. Purification by column chromatography (6:4 Hexanes-EtOAc) gave the title compound, 0.34 g (66%) as a yellowish powder. 1H NMR (300 MHz, DMSO-d$_6$) δ 8.79 (s, 1H), 8.35 (d, J=3 Hz, 1H), 8.10-8.06 (m, 1H), 7.94 (d, J=9 Hz, 1H), 7.58-7.50 (m, 3H), 6.37 (d, J=7 Hz, 1H), 4.61-4.47 (m, 1H), 3.63-3.46 (m, 1H), 2.15-1.87 (m, 4H), 1.53-1.31 (m, 4H), 1.54 (s, 9H).

Example 12

Preparation of trans-5-{4-[3-(4-Chloro-3-trifluoromethyl-phenyl)-ureido]-cyclohexyloxy}-pyridine-2-carboxylic acid methylamide (2316)

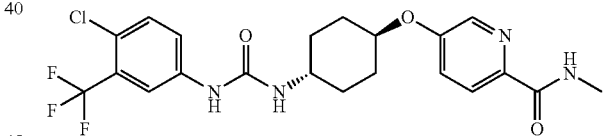

Compound 2315 from Example 11 (0.27 g, 0.53 mmol) was dissolved in 30% TFA in DCM (10 mL) at room temperature. The reaction mixture was stirred for 6 h and concentrated in vacuo. After adding Et2O (20 mL), the resulting solid was filtered and washed with Et$_2$O to give the TFA salt (0.24 g, 80%) as a white solid. To the TFA salt of the carboxylic acid (0.1 g, 0.18 mmol), EDC (0.1 g, 0.53 mmol), DIPEA (0.18 mL, 1.05 mmol) in THF (5 mL) was added methylamine hydrochloride (35 mg, 0.53 mmol) at room temperature. After 3 h, 2M MeNH$_2$ in THF (0.87 mL) was added at room temperature. The reaction mixture was stirred overnight. The solvent was removed in vacuo and then purified by column chromatography (1:1 Hexanes-EtOAc) gave the title compound, 50 mg (61%) as a white solid. $^1$H NMR (300 MHz, DMSO-d$_6$) δ 8.88-8.79 (m, 1H), 8.74 (q, J=5 Hz, 1H), 8.41 (d, J=6 Hz, 1H), 8.08 (d, J=2 Hz, 1H), 7.58-7.48 (m, 3H), 7.15 (dd, J=6 and 3 Hz, 1H), 6.36 (d, J=8 Hz, 1H), 4.68-4.52 (m, 1H), 3.65-3.46 (m, 1H), 2.80 (d, J=5 Hz, 3H), 2.13-1.87 (m, 4H), 1.62-1.33 (m, 4H).

Example 13

Preparation of cis-4-{4-[3-(4-Chloro-3-trifluoromethyl-phenyl)-ureido]-cyclohexyloxy}-pyridine-2-carboxylic acid tert-butyl ester (2318)

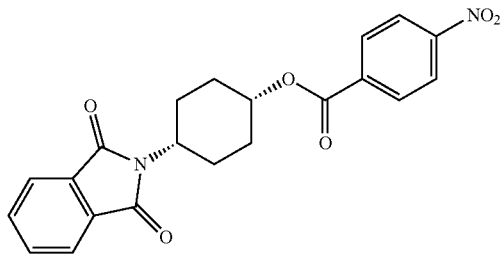 [SMILES: O=C(O[C@H]1CC[C@@H](N2C(=O)c3ccccc3C2=O)CC1)c1ccc([N+](=O)[O-])cc1]

cis-4-Nitro-benzoic acid 4-(1,3-dioxo-1,3-dihydro-isoindol-2-yl)-cyclohexyl ester (5). To a solution of trans-2-(4-hydroxy-cyclohexyl)-isoindole-1,3-dione (38 g, 155 mmol), triphenylphosphine (65 g, 248 mmol), and 4-nitrobenzoic acid (41 g, 248 mmol) in 1500 mL of THF was added dropwise diisopropyl azodicarboxylate (50 g, 248 mmol) at room temperature. The reaction mixture was stirred overnight. The solvent was evaporated, and the resulting solid was recrystallized from methanol to afford 53 g (87%) of the title compound as a white solid. $^1$H NMR (CDCl$_3$): δ 8.40-8.36 (m, 4H), 7.79 (ddd, J=0.12, 0.02, and 0.02 Hz, 4H), 5.39 (s, 1H), 4.37-4.22 (m, 1H), 2.82-2.65 (m, 2H), 2.27-2.16 (m, 2H), 1.84-1.65 (m, 4H).

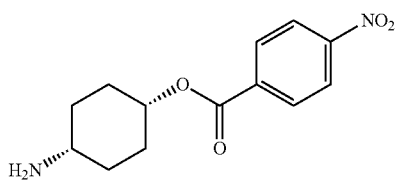 [SMILES: N[C@H]1CC[C@@H](OC(=O)c2ccc([N+](=O)[O-])cc2)CC1]

cis-4-Nitro-benzoic acid 4-amino-cyclohexyl ester (1075)

35 wt % Hydrazine hydrate (0.93 g, 10.1 mmol) was added to a solution of compound 5 (2.0 g, 5.1 mmol) in CH$_2$Cl$_2$ (50 mL) followed by MeOH (50 mL) at room temperature. The reaction mixture was allowed to stir overnight. The resulting white precipitates were filtered off and the solvent was removed in vacuo. The resulting white solids were dissolved in aqueous 1N HCl solution and washed with CH$_2$Cl$_2$. Aqueous layer was basified with excess 1N NaOH solution and then extracted with CH$_2$Cl$_2$. After drying with MgSO$_4$, the solvent was evaporated affording crude trans-4-nitro-benzoic acid 4-amino-cyclohexyl ester 6 as a white solid (1.1 g, 89% yield), which was used in the next step without further purification. $^1$H NMR (DMSO-d$_6$): δ 8.26 (dd, J=44 and 9 Hz, 4H), 6.72 (d, J=7 Hz, 2H), 5.08 (s, 1H), 2.00-1.36 (m, 9H).

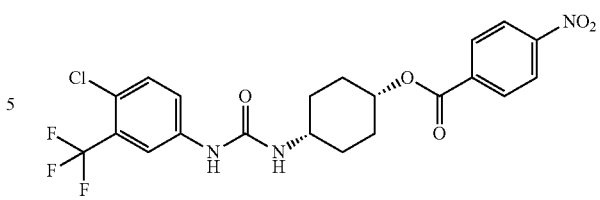

cis-4-Nitro-benzoic acid 4-[3-(4-chloro-3-trifluoromethyl-phenyl)-ureido]-cyclohexa-2,3-dienyl ester To a solution compound 1075 (1.2 g, 4.5 mmol) in DMF (45 mL) was added 4-chloro-3-(trifluoromethyl)phenyl isocyanate (1 g, 4.5 mmol) followed by triethylamine (0.63 mL, 4.5 mmol) at 0° C. The reaction mixture was stirred overnight. The reaction mixture was poured into water, and the resulting precipitates were collected and washed with water. The crude product was recrystallized from CH$_2$Cl$_2$/hexanes to afford 1.5 g (68%) of the title compound as a white solid. $^1$H NMR (300 MHz, DMSO-d$_6$) δ 8.82 (s, 1H), 8.37 (d, J=9 Hz, 1H), 8.22 (d, J=9 Hz, 1H), 8.09 (s, 1H), 7.58-7.49 (m, 1H), 6.49 (d, J=8 Hz, 1H), 5.18-5.04 (m, 1H), 3.74-3.58 (m, 1H), 2.07-1.50 (m, 1H).

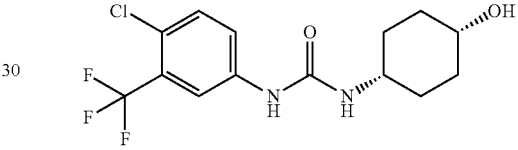

cis-1-(4-Chloro-3-trifluoromethyl-phenyl)-3-(4-hydroxy-cyclohexyl)-urea

To a solution of cis-4-nitro-benzoic acid 4-[3-(4-chloro-3-trifluoromethyl-phenyl)-ureido]-cyclohexa-2,3-dienyl ester (0.8 g, 1.6 mmol) in THF (15 mL) was added 1N NaOH solution (3.3 mL) at room temperature. The reaction mixture was stirred overnight, at which time the reaction was quenched by addition of 1N HCl solution (6 mL). The resulting white precipitate was collected by filtration and recrystallized from methanol/water to afford 0.5 g (90% yield) of the title compound as a white solid. mp 203.4-207.1° C. $^1$H NMR (DMSO-d$_6$): δ 1H NMR (300 MHz, DMSO-d6) δ 8.76 (s, 1H), 8.07-8.04 (m, 1H), 7.55-7.46 (m, 2H), 6.32 (d, J=8 Hz, 1H), 4.46-4.42 (m, 1H), 3.67-3.50 (m, 2H), 2.53-2.46 (m, 8H).

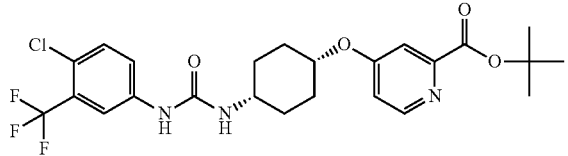

cis-4-{4-[3-(4-Chloro-3-trifluoromethyl-phenyl)-ureido]-cyclohexyloxy}-pyridine-2-carboxylic acid tert-butyl ester (2318)

To a solution of cis-1-(4-chloro-3-trifluoromethyl-phenyl)-3-(4-hydroxy-cyclohexyl)-urea (0.38 g, 1.13 mmol) and tert-butyl 4-chloropicolinate (0.24 g, 1.13 mmol) in THF (12 mL) was added 1.0 M potassium tert-butoxide solution in THF (3.4 mL, 3.4 mmol) at 0° C. The reaction mixture was allowed to slowly warm to room temperature and then stirred overnight. The reaction was quenched by adding water and the resulting white precipitates were collected and washed with water. Purification by column chromatography (6:4 Hexanes-EtOAc) gave the title compound, 0.32 g (55%) as a yellowish powder. $^1$H NMR (300 MHz, DMSO-d$_6$  δ 8.78 (s, 1H), 8.48 (d, J=6 Hz, 1H), 8.09-8.06 (m, 1H), 7.55-7.50 (m, 2H), 7.46 (d, J=2 Hz, 1H), 7.21 (dd, J=6 and 2 Hz, 1H), 6.48 (d, J=8 Hz, 1H), 4.82-4.67 (m, 1H), 3.75-3.59 (m, 1H), 1.91-1.47 (m, 17H).

Example 14

Preparation of cis-4-{4-[3-(4-chloro-3-trifluoromethyl-phenyl)-ureido]-cyclohexyloxy}-pyridine-2-carboxylic acid methylamide (c-CUPM) (2319)

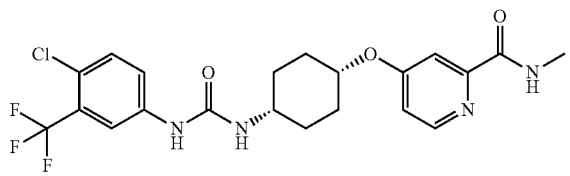 [SMILES: CNC(=O)c1cc(O[C@H]2CC[C@@H](NC(=O)Nc3ccc(Cl)c(C(F)(F)F)c3)CC2)ccn1]

Compound 2318 (0.27 g, 0.53 mmol) was dissolved in 30% TFA in DCM (10 mL) at room temperature. The reaction mixture was stirred for 6 h and concentrated in vacuo. After adding Et$_2$O (20 mL), the resulting solid was filtered and washed with Et$_2$O to give the corresponding acid (0.23 g) in 77% yield as the TFA salt. To the TFA salt of the carboxylic acid (0.05 g, 0.09 mmol), EDC (0.05 g, 0.26 mmol), DIPEA (0.09 mL, 0.07 mmol) in THF (2 mL) was added methylamine hydrochloride (0.02 g, 0.26 mmol) at room temperature. After 3 h, 2M MeNH$_2$ in THF (0.44 mL) was added at room temperature. The reaction mixture was stirred overnight. The solvent was removed in vacuo and then purified by column chromatography (1:1 Hexanes-EtOAc) gave the title compound, 25 mg (61%) as a white solid. $^1$H NMR (300 MHz, DMSO-d$_6$ ) δ 8.82-8.75 (m, 1H), 8.74 (dd, J=9.54, 4.58 Hz, 1H), 8.42 (d, J=5.66 Hz, 1H), 8.09-8.06 (m, 1H), 7.58-7.47 (m, 3H), 7.16 (dd, J=5.66, 2.59 Hz, 1H), 6.49 (d, J=7.57 Hz, 1H), 4.82-4.68 (m, 1H), 3.74-3.58 (m, 1H), 2.79 (d, J=4.81 Hz, 3H), 1.90-1.43 (m, 8H).

Example 15

Preparation of trans-4-{4-[3-(4-Trifluoromethoxy-phenyl)-ureido]-cyclohexyloxy}-pyridine-2-carboxylic acid tert-butyl ester (07046)

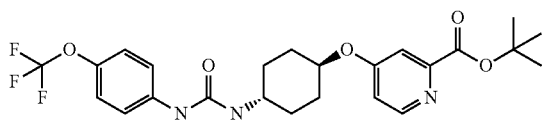

Compound 07046 was prepared in 87% yield from 1728 using the procedure detailed for compound 2280 in Example 9. $^1$H NMR (400 MHz, DMSO-d$_6$): δ 8.52 (s, 1H), 8.46 (dd, J=6 and 2 Hz, 1H), 7.50-7.43 (m, 3H), 7.23-7.18 (m, 3H), 6.21 (d, J=7.39 Hz, 1H), 4.63-4.53 (m, 1H), 3.60-3.49 (m, 1H), 2.09-1.89 (m, 4H), 1.58-1.32 (m, 4H), 1.54 (s, 9H).

Example 16

Preparation of trans-4-{4-[3-(4-Trifluoromethoxy-phenyl)-ureido]-cyclohexyloxy}-pyridine-2-carboxylic acid methylamide (2575)

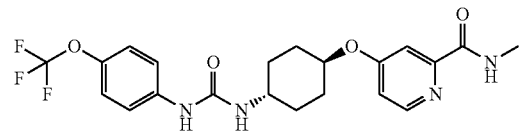 [SMILES: CNC(=O)c1cc(O[C@H]2CC[C@H](NC(=O)Nc3ccc(OC(F)(F)F)cc3)CC2)ccn1]

Compound 2575 was prepared in 80% yield from 07046 using the procedure detailed for compound 2278 in Example 8. $^1$H NMR (400 MHz, DMSO-d$_6$): δ 8.73 (q, J=5 Hz, 1H), 8.54 (s, 1H), 8.40 (d, J=6 Hz, 1H), 7.51 (d, J=3 Hz, 1H), 7.47 (d, J=9 Hz, 2H), 7.22 (d, J=9 Hz, 2H), 7.15 (dd, J=6 and 3 Hz, 1H), 6.21 (d, J=8 Hz, 1H), 4.65-4.55 (m, 1H), 3.60-3.48 (m, 1H), 2.80 (d, J=5 Hz, 3H), 2.10-2.01 (m, 2H), 1.98-1.90 (m, 2H), 1.59-1.34 (m, 4H).

Example 17

Preparation of trans-4-{4-[3-(4-Trifluoromethoxy-phenyl)-ureido]-cyclohexyloxy}-pyridine-2-carboxylic acid diethylamide (2577)

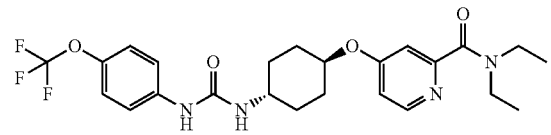 [SMILES: CCN(CC)C(=O)c1cc(O[C@H]2CC[C@H](NC(=O)Nc3ccc(OC(F)(F)F)cc3)CC2)ccn1]

Compound 2577 was prepared in 80% yield from 07046 and diethylamine using the procedure detailed for compound 2278 in Example 8. $^1$H NMR (400 MHz, DMSO-d$_6$): δ 8.52 (s, 1H), 8.33 (d, J=6 Hz, 1H), 7.47 (d, J=9 Hz, 2H), 7.22 (d, J=9 Hz, 2H), 7.06 (d, J=3 Hz, 1H), 7.01 (dd, J=6 and 3 Hz, 1H), 6.20 (d, J=8 Hz, 1H), 4.61-4.53 (m, 1H), 3.58-3.47 (m, 1H), 3.42 (q, J=7 Hz, 2H), 3.21 (q, J=7 Hz, 2H), 2.09-2.00 (m, 2H), 1.97-1.88 (m, 2H), 1.58-1.32 (m, 4H), 1.14 (t, J=7 Hz, 3H), 1.06 (t, J=7 Hz, 3H).

Example 18

Preparation of trans-1-{4-[2-(Pyrrolidine-1-carbonyl)-pyridin-4-yloxy]-cyclohexyl}-3-(4-trifluoromethoxy-phenyl)-urea (2578)

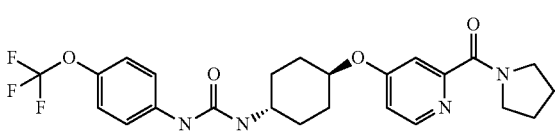

Compound 2578 was prepared in 80% yield from 07046 and pyrrolidine using the procedure detailed for compound 2278 in Example 8. $^1$H NMR (400 MHz, DMSO-$d_6$): δ 8.52 (s, 1H), 8.36 (d, J=6 Hz, 1H), 7.47 (d, J=9 Hz, 2H), 7.24-7.20 (m, 3H), 7.05 (dd, J=6 and 3 Hz, 1H), 6.21 (d, J=8 Hz, 1H), 4.61-4.52 (m, 1H), 3.59-3.44 (m, 5H), 2.09-2.00 (m, 2H), 1.97-1.88 (m, 2H), 1.87-1.78 (m, 4H), 1.58-1.31 (m, 4H).

Example 19

Preparation of trans-4-{4-[3-(4-Chloro-3-trifluoromethyl-phenyl)-ureido]-cyclohexyloxy}-pyridine-2-carboxylic acid diethylamide (2574)

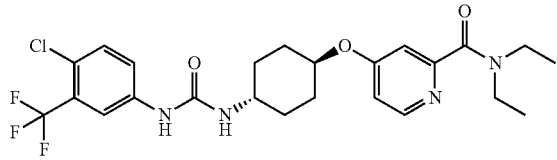 [SMILES: CCN(CC)C(=O)c1cc(O[C@H]2CC[C@H](NC(=O)Nc3ccc(Cl)c(C(F)(F)F)c3)CC2)ccn1]

Compound 2574 was prepared in 82% yield from 2280 using the procedure using compound 2278 detailed in Example 8. $^1$H NMR (400 MHz, DMSO-$d_6$): δ 8.81 (s, 1H), 8.33 (d, J=6 Hz, 1H), 8.08 (d, J=2.12 Hz, 1H), 7.56-7.50 (m, 2H), 7.06 (d, J=3 Hz, 1H), 7.01 (dd, J=6 and 3 Hz, 1H), 6.35 (d, J=7.55 Hz, 1H), 4.62-4.51 (m, 1H), 3.59-3.48 (m, 1H), 3.42 (q, J=7.05, 7.05, 6.99 Hz, 2H), 3.21 (q, J=7.02, 7.01, 7.01 Hz, 2H), 2.10-2.01 (m, 2H), 1.96-1.88 (m, 2H), 1.58-1.34 (m, 4H), 1.14 (t, J=7.07, 7.07 Hz, 3H), 1.06 (t, J=7.02, 7.02 Hz, 3H)

Example 20

Preparation of trans-4-[4-(3-adamantan-1-yl-ureido]-cyclohexyloxy)-N-methyl-benzamide (2225)

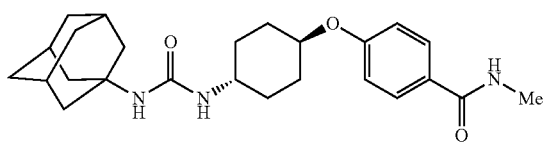 [SMILES: CNC(=O)c1ccc(O[C@H]2CC[C@H](NC(=O)NC34CC5CC(CC(C5)C3)C4)CC2)cc1]

To a solution of 1471 (0.21 g, 0.5 mmol), EDC HCl (0.12 g, 0.63 mmol), HOBT (0.09 g, 0.63 mmol), TEA (0.17 mL, 0.63 mmol) in THF (10 mL) was added 2M MeNH2 in THF (1.25 mL, 2.5 mmol) at 0° C. The reaction mixture was allowed to slowly warm to room temperature overnight. The solvent was removed in vacuo and then purified by recrystallization with EtOAc/Hexanes gave the title compound, 0.18 g (85%) as a white solid. $^1$H NMR (300 MHz, DMSO-$d_6$): δ 8.25 (q, J=5 Hz, 1H), 7.76 (d, J=9 Hz, 2H), 6.97 (d, J=9 Hz, 2H), 5.61 (d, J=8 Hz, 1H), 5.40 (s, 1H), 4.46-4.31 (m, 1H), 3.43-3.28 (m, 1H), 2.75 (d, J=5 Hz, 3H), 2.07-1.93 (m, 5H), 1.90-1.77 (m, 8H), 1.67-1.53 (m, 6H), 1.50-1.33 (m, 2H), 1.29-1.13 (m, 2H).

Example 21

Preparation of 4-[4-(3-adamantan-1-yl-ureido)-phenoxy]-pyridine-2-carboxylic acid methylamide (2287)

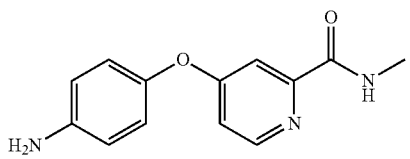 [SMILES: CNC(=O)c1cc(Oc2ccc(N)cc2)ccn1]

4-(4-Amino-phenoxy)-pyridine-2-carboxylic acid methylamide

To a solution of 4-aminophenol (1 g, 9.2 mmol) in DMF (20 mL) was added 1M potassium tert-butoxide in THF (9.7 mL, 9.7 mmol) at room temperature. After 2 h, (4-chloro(2-pyridyl))-N-methylcarboxamide (1.6 g, 9.2 mmol) and potassium carbonate (0.64 g, 4.6 mmol) were added and then the reaction mixture was heated to 80° C. for 6 h. After cooling, the reaction mixture was extracted with ethyl acetate (50 mL). The organic layer was washed with brine (20 mL), dried over magnesium sulfate. The solvent was removed in vacuo. The residue was purified by column chromatography to afford 4-(4-amino-phenoxy)-pyridine-2-carboxylic acid methylamide (2.2 g, 80%) as a light-brown solid. $^1$H NMR (400 MHz, DMSO-$d_6$): δ 8.94 (s, 1H), 8.89 (s, 1H), 8.78 (q, J=5 Hz, 1H), 8.50 (d, J=6 Hz, 1H), 7.61-7.54 (m, 4H), 7.38 (d, J=3 Hz, 1H), 7.29 (d, J=9 Hz, 2H), 7.19-7.12 (m, 3H), 2.78 (d, J=5 Hz, 3H).

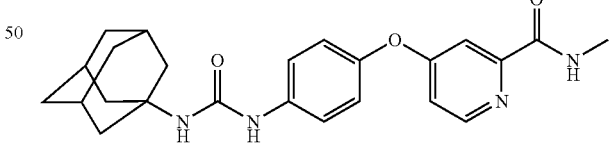

4-[4-(3-Adamantan-1-yl-ureido)-phenoxy]-pyridine-2-carboxylic acid methylamide (2287)

Compound 2287 was prepared in 60% yield from adamantyl isocyanate and 4-(4-amino-phenoxy)-pyridine-2-carboxylic acid methylamide using the procedure detailed for compound 2221 in Example 4. $^1$H NMR (300 MHz, DMSO-$d_6$) δ 8.73 (q, J=5 Hz, 1H), 8.48 (d, J=6 Hz, 1H), 8.39 (s, 1H), 7.49-7.42 (m, 2H), 7.36 (d, J=2 Hz, 1H), 7.13-7.03 (m, 3H), 5.89 (s, 1H), 2.78 (d, J=5 Hz, 3H), 2.09-2.01 (m, 3H), 1.98-1.92 (m, 6H), 1.68-1.60 (m, 6I).

Example 22

Preparation of N-methyl-3-{4-[3-(4-trifluoromethoxy-phenyl)-ureido]-phenoxy}-benzamide (2576)

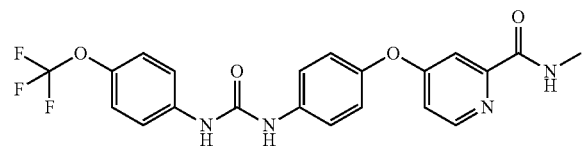 [SMILES: CNC(=O)c1cc(Oc2ccc(NC(=O)Nc3ccc(OC(F)(F)F)cc3)cc2)ccn1]

Compound 2576 was prepared in 70% yield from 4-(trifluoromethoxy)phenyl isocyanate using the procedure detailed for compound 2221 in Example 4. $^1$H NMR (300 MHz, DMSO-d$_6$): δ 8.75 (q, J=5 Hz, 1H), 8.45 (d, J=6 Hz, 1H), 7.33 (d, J=3 Hz, 1H), 7.07 (dd, J=6 and 3 Hz, 1H), 6.86 (d, J=9 Hz, 2H), 6.64 (d, J=9 Hz, 2H), 5.19 (br s, 2H), 2.77 (d, J=5 Hz, 3H).

Example 23

Preparation of trans-4-{4-[3-(4-Trifluoromethyl-phenyl)-ureido]-cyclohexyloxy}-benzoic acid (2372)

Method A

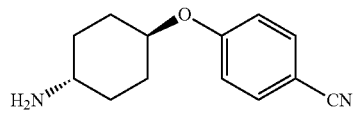 [SMILES: N#Cc1ccc(O[C@H]2CC[C@H](N)CC2)cc1]

trans-4-(4-Amino-cyclohexyloxy)-benzonitrile

To a solution of trans-4-aminocyclohexanol (3 g, 26 mmol) in DMF (130 mL) at 0° C. was added 60% sodium hydride in oil. The reaction mixture was stirred at 0° C. for 1 h and then 4-fluorobenzonitrile (3.9 g, 32.6 mmol) was added. It was heated to 60° C. for 2 h and stirred for 12 h at room temperature. The reaction mixture was diluted with EtOAc and washed with water and brine. The organic layer was dried, filtered, and concentrated under reduced pressure to provide the titled compound (2.5 g, 44% yield). $^1$H NMR (300 MHz, DMSO-d$_6$): δ7.72 (d, J=9 Hz, 2H), 7.09 (d, J=9 Hz, 2H), 4.48-4.34 (m, 1H), 2.68-2.55 (m, 1H), 2.07-1.94 (m, 2H), 1.85-1.71 (m, 2H), 1.46-1.11 (m, 4H).

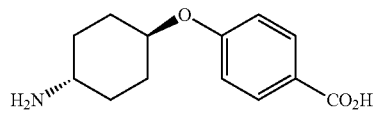

trans-4-(4-Amino-cyclohexyloxy)-benzoic acid

To a solution of trans-4-(4-amino-cyclohexyloxy)-benzonitrile (2.5 g, 11.6 mmol) in EtOH (100 mL) was added 6N NaOH solution (29 mL) at room temperature. The reaction mixture was gently heated up to 80° C. and stirred for 18 h. After evaporating ethanol, the reaction mixture was acidified with conc. HCl at 0° C. and then basified with saturated NaHCO$_3$ until pH~7-8. The resulting precipitates were filtered and washed with water to give the title compound (2.7 g, 82% yield) as a white solid. $^1$H NMR (300 MHz, DMSO-d$_6$): δ 8.04 (d, J=9 Hz, 2H), 6.97 (d, J=9 Hz, 2H), 6.82 (br s, 3H), 4.50-4.33 (m, 1H), 3.55-3.39 (m, 1H), 2.42-2.16 (m, 2H), 1.81-1.57 (m, 2H).

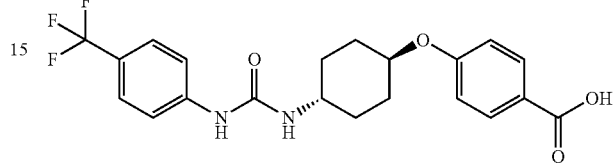

trans-4-{4-[3-(4-Trifluoromethyl-phenyl)-ureido]-cyclohexyloxy}-benzoic acid (2372)

Compound 2372 was prepared in 70% yield from 4-(trifluoromethyl)phenyl isocyanate and trans-4-(4-amino-cyclohexyloxy)-benzoic acid using the procedure detailed for compound 2221 in Example 4. $^1$H NMR (400 MHz, DMSO-d$_6$): δ 12.62 (s, 1H), 9.00 (s, 1H), 7.86 (d, J=9 Hz, 2H), 7.60-7.53 (m, 4H), 7.02 (d, J=9 Hz, 2H), 6.52 (d, J=8 Hz, 1H), 4.50-4.40 (m, 1H), 3.60-3.48 (m, 1H), 2.11-2.01 (m, 2H), 1.98-1.89 (m, 2H), 1.56-1.32 (m, 4H).

Method B

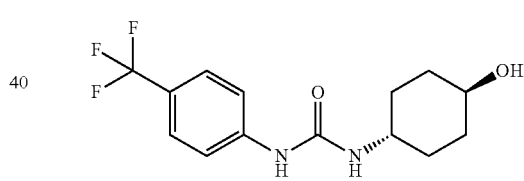

trans-1-(4-Hydroxy-cyclohexyl)-3-(4-trifluoromethyl-phenyl)-urea (08070)

Compound 2579 was prepared in 83% yield from 4-trifluoromethylphenyl isocyanate using the procedure detailed for compound 07086 in Example 4. $^1$H NMR (400 MHz, DMSO-d$_6$): δ 8.72 (s, 1H), 7.62-7.50 (m, 4H), 6.16 (d, J=7 Hz, 1H), 4.55-4.52 (m, 1H), 3.46-3.35 (m, 2H), 1.87-1.76 (m, 4H), 1.31-1.11 (m, 4H).

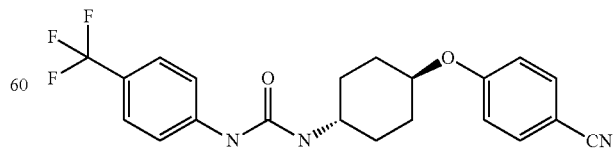

trans-1-[4-(4-Cyano-phenoxy)-cyclohexyl]-3-(4-trifluoromethyl-phenyl)-urea (2579). Compound 2579 was prepared in 90% yield from 08070 using the procedure detailed for compound 2182 in Example 4. ¹H NMR (400 MHz, DMSO-d₆): δ 8.73 (s, 1H), 7.74 (d, J=9 Hz, 2H), 7.60-7.53 (m, 4H), 7.13 (d, J=9 Hz, 2H), 6.32 (d, J=8 Hz, 1H), 4.56-4.43 (m, 1H), 3.62-3.47 (m, 1H), 2.14-1.86 (m, 4H), 1.58-1.31 (m, 4H).

Example 24

In Vitro Kinase Inhibition Assay

Inhibitor Concentration at 50% enzyme inhibition ($IC_{50}$) values were calculated by quantifying the end-point ADP production from each kinase reaction using the ADP-Glo™ Kinase Assay (Promega, Madison, Wis.) as described by the manufacturer. Reactions were performed in Tris buffer (50 mM pH 7.5, RT) containing 20 mM $MgCl_2$ and 0.1% Bovine Serum Albumin. Each assay was performed in 60 μL of the solution in 10×75 mm borosilicate glass test tubes and allowed to continuously shake during the duration of the assay. The total ADP generated was quantified by transferring 25 μL (2×) of each assay to a 96-well luminescence assay plate, followed by the addition of 25 μL of ADP-Glo™ Reagent (45 min incubation) to remove any remaining ATP. For luminescence readings, 50 μL of Kinase Detection Reagent™ (45 min incubation) was added to convert the ADP generated from the kinase reaction to ATP, and luminescent intensity was measured using a luciferase/luciferin reaction, as indicated by the manufacturer. All measurements included background and control (vehicle only) luminescence readings.

The kinases Raf-1 and b-Raf (V600E), and their corresponding substrate, MEK1, and Full length recombinant CRAF kinase and its respective substrate, recombinant MEK1, were purchased from US Biological (Swampscott, Mass.). All assays were performed under identical conditions for the Raf isozymes: 10 nM Enzyme, 1 μM MEK1, 10 μM ATP, at 22° C. for 2 hours. Initial time-based measurements were performed to ensure a linear turnover throughout the duration of the assay (data not shown). Inhibitors were dissolved in DMSO and diluted to appropriate initial concentrations so that the addition of 1 μL yielded the desired final concentration. $IC_{50}$ values were obtained by determining the change in the ADP production (luminescence signal) at various inhibitor concentrations as compared to the control assay. Individual data sets were performed in duplicate and each $IC_{50}$ was determined by the average and standard deviation of three separate experiments. The data was fit to saturation curve using KaleidaGraph (Synergy Software) and the inhibition at 50% activity was determined ($IC_{50}$).

TABLE 1

Inhibitory activities against human sEH and Raf kinases[a]

| Compound | Structure | Human sEH (nM) | Raf-1 (nM) | b-Raf (V600E) (nM) |
|---|---|---|---|---|
| Sorafenib | 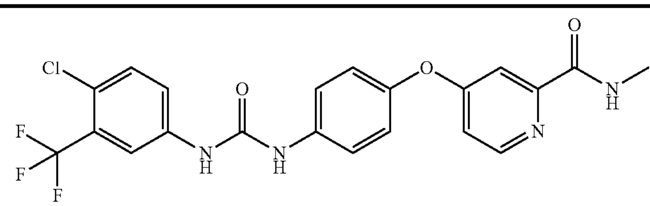 | 12 ± 2 | 45 ± 7.0 | 12.7 ± 1.5 |
| Sunitinib | 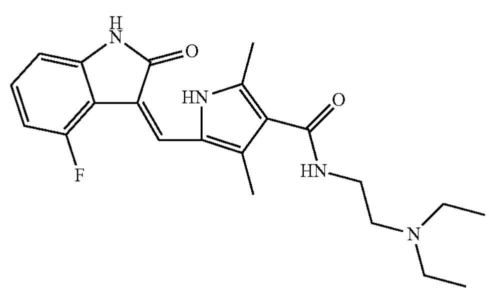 [SMILES: CCN(CC)CCNC(=O)c1c(C)[nH]c(/C=C2\C(=O)Nc3cccc(F)c32)c1C] | >10000 | >10000 | ND |
| 1471 (t-AUCB) | 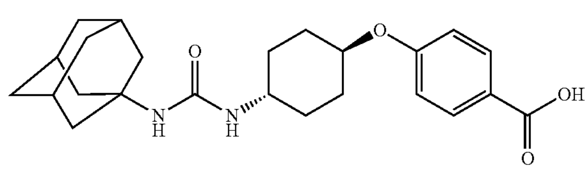 [SMILES: O=C(NC12CC3CC(CC(C3)C1)C2)N[C@H]1CC[C@H](Oc2ccc(C(=O)O)cc2)CC1] | 1.5 | ND | ND |
| 1612 | 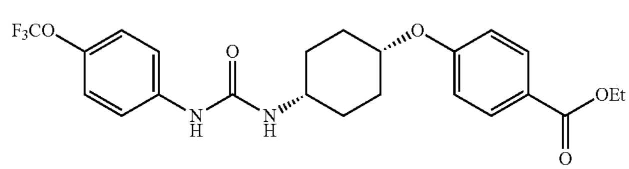 [SMILES: CCOC(=O)c1ccc(O[C@H]2CC[C@@H](NC(=O)Nc3ccc(OC(F)(F)F)cc3)CC2)cc1] | 3.4 | ND | ND |

TABLE 1-continued

Inhibitory activities against human sEH and Raf kinases[a]

| Compound | Structure | % Inhibition (IC$_{50}$) | | |
|---|---|---|---|---|
| | | Human sEH (nM) | Raf-1 (nM) | b-Raf (V600E) (nM) |
| 1686 | F$_3$CO-phenyl-NH-C(O)-NH-cyclohexyl-O-phenyl-COOH | 0.6 | ND | ND |
| 1728 (t-TUCB) | F$_3$CO-phenyl-NH-C(O)-NH-cyclohexyl-O-phenyl-COOH | 0.9 ± 0.1 | >10000 | ND |
| 2084 | Cl-phenyl-NH-C(O)-NH-cyclohexyl-O-phenyl-COOH | 5.5 | >10000 | ND |
| 2182 | Cl,CF$_3$-phenyl-NH-C(O)-NH-cyclohexyl-O-phenyl-CN | 14.6 | ND | ND |
| 2221 | Cl,CF$_3$-phenyl-NH-C(O)-NH-cyclohexyl-O-phenyl-COOH | 0.5 | 4300 ± 400 | >10000 |
| 2225 | adamantyl-NH-C(O)-NH-cyclohexyl-O-phenyl-C(O)NHMe | 0.5 | >10000 | ND |
| 2227 | F$_3$CO-phenyl-NH-C(O)-NH-cyclohexyl-O-phenyl-C(O)NHMe | 0.5 | 340 ± 40 | >10000 |
| 2228 | F$_3$CO-phenyl-NH-C(O)-NH-cyclohexyl-O-phenyl-C(O)NHMe | 0.5 | >10000 | ND |
| 2253 | Cl,CF$_3$-phenyl-NH-C(O)-NH-cyclohexyl-O-phenyl-C(O)NHMe | 0.5 | ND | ND |

TABLE 1-continued

Inhibitory activities against human sEH and Raf kinases[a]

| Compound | Structure | Human sEH (nM) | Raf-1 (nM) | b-Raf (V600E) (nM) |
|---|---|---|---|---|
| 2278 (t-CUPM) | 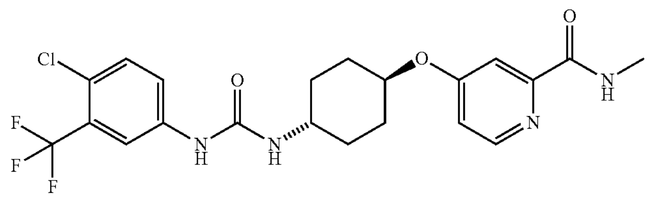 | 0.5 | 75 ± 10 | 570 ± 30 |
| 2280 | 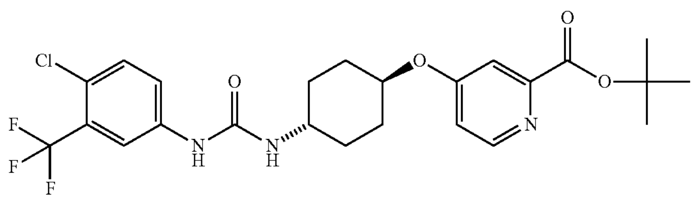 | 0.9 | 550 ± 50 | >10000 |
| 2287 | 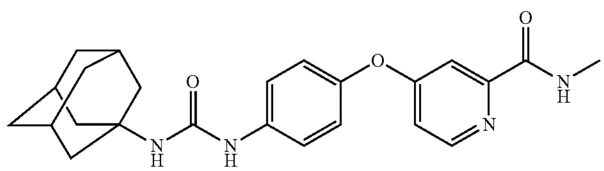 [SMILES: CNC(=O)c1cc(Oc2ccc(NC(=O)NC34CC5CC(CC(C5)C3)C4)cc2)ccn1] | 0.5 | >10000 | >10000 |
| 2288 | 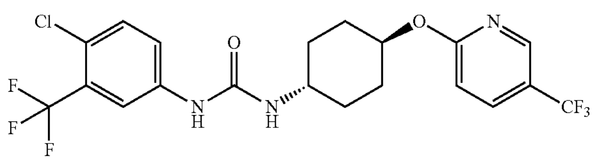 [SMILES: O=C(Nc1ccc(Cl)c(C(F)(F)F)c1)N[C@H]1CC[C@H](Oc2ccc(C(F)(F)F)cn2)CC1] | 9 | >10000 | >10000 |
| 2315 | 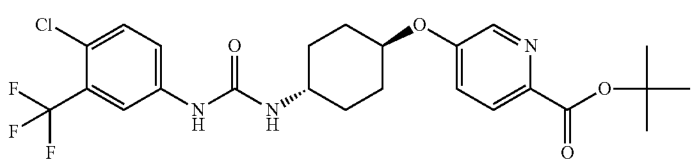 [SMILES: CC(C)(C)OC(=O)c1ccc(O[C@H]2CC[C@H](NC(=O)Nc3ccc(Cl)c(C(F)(F)F)c3)CC2)cn1] | 0.5 | >10000 | ND |
| 2316 | 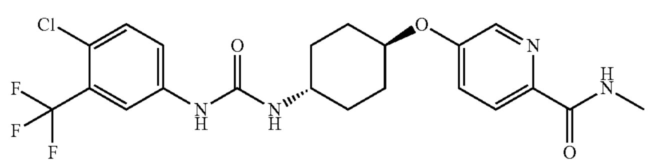 [SMILES: CNC(=O)c1ccc(O[C@H]2CC[C@H](NC(=O)Nc3ccc(Cl)c(C(F)(F)F)c3)CC2)cn1] | 0.5 | 175 ± 20 | 1,500 ± 150 |
| 2318 | 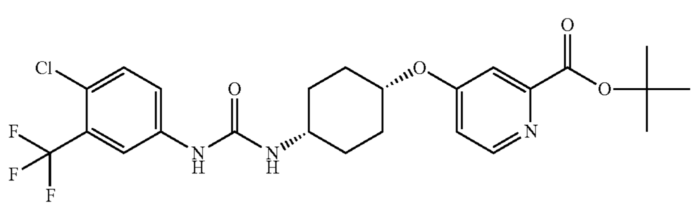 [SMILES: CC(C)(C)OC(=O)c1cc(O[C@H]2CC[C@@H](NC(=O)Nc3ccc(Cl)c(C(F)(F)F)c3)CC2)ccn1] | 0.5 | 54%* | 51%* |
| 2319 (c-CUPM) | 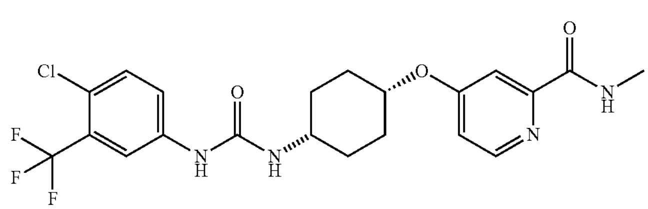 | 0.5 | 1500 ± 250 | 330 ± 100 |

TABLE 1-continued

Inhibitory activities against human sEH and Raf kinases[a]

| Compound | Structure | Human sEH (nM) | Raf-1 (nM) | b-Raf (V600E) (nM) |
|---|---|---|---|---|
| 2372 | 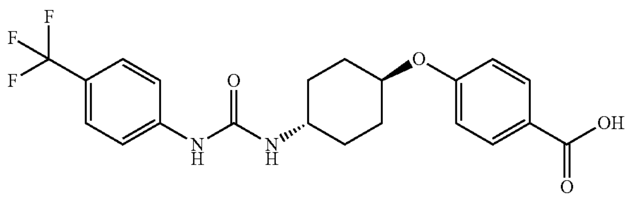 [SMILES: O=C(Nc1ccc(C(F)(F)F)cc1)N[C@H]1CC[C@H](Oc2ccc(C(=O)O)cc2)CC1] | 0.9 | >10000 | ND |
| 2574 | 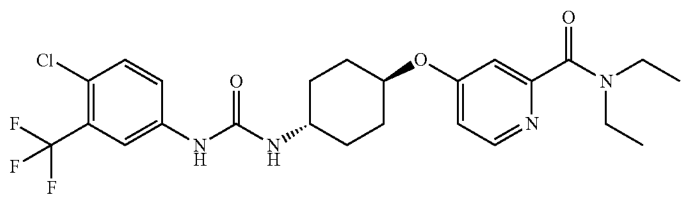 [SMILES: CCN(CC)C(=O)c1cc(O[C@H]2CC[C@H](NC(=O)Nc3ccc(Cl)c(C(F)(F)F)c3)CC2)ccn1] | 0.5 | >10000 | ND |
| 2575 | 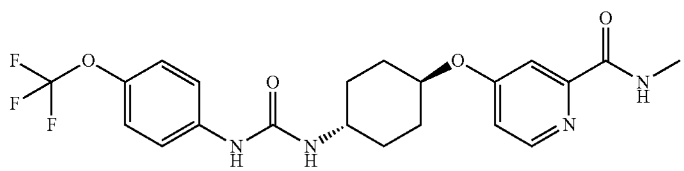 [SMILES: CNC(=O)c1cc(O[C@H]2CC[C@H](NC(=O)Nc3ccc(OC(F)(F)F)cc3)CC2)ccn1] | 0.5 | >10000 | ND |
| 2576 | 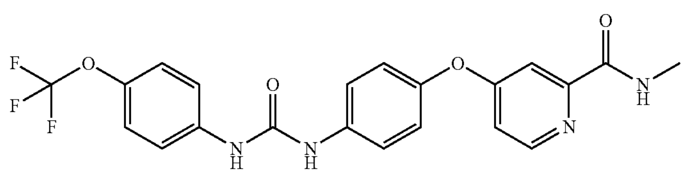 [SMILES: CNC(=O)c1cc(Oc2ccc(NC(=O)Nc3ccc(OC(F)(F)F)cc3)cc2)ccn1] | 0.5 | 30 | ND |
| 2577 | 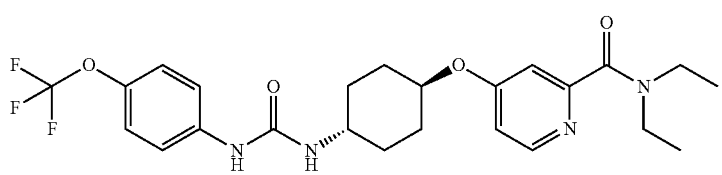 [SMILES: CCN(CC)C(=O)c1cc(O[C@H]2CC[C@H](NC(=O)Nc3ccc(OC(F)(F)F)cc3)CC2)ccn1] | 0.5 | ND | ND |
| 2578 | 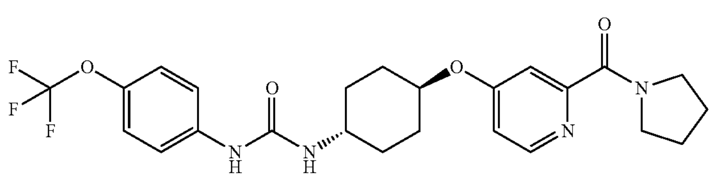 [SMILES: O=C(Nc1ccc(OC(F)(F)F)cc1)N[C@H]1CC[C@H](Oc2ccnc(C(=O)N3CCCC3)c2)CC1] | 0.5 | ND | ND |
| 2579 | 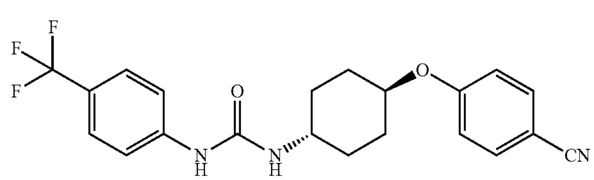 [SMILES: N#Cc1ccc(O[C@H]2CC[C@H](NC(=O)Nc3ccc(C(F)(F)F)cc3)CC2)cc1] | 0.5 | ND | ND |
| 2580 | 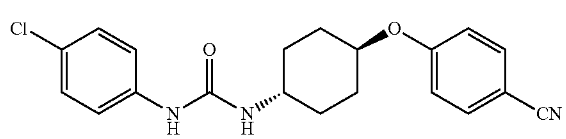 [SMILES: N#Cc1ccc(O[C@H]2CC[C@H](NC(=O)Nc3ccc(Cl)cc3)CC2)cc1] | 0.5 | ND | ND |

TABLE 1-continued

Inhibitory activities against human sEH and Raf kinases[a]

| Compound | Structure | Human sEH (nM) | Raf-1 (nM) | b-Raf (V600E) (nM) |
|---|---|---|---|---|
| 2581 | 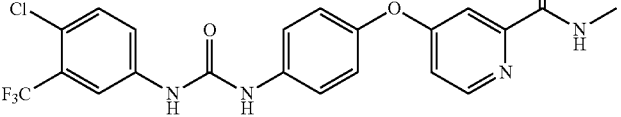 | 0.5 | ND | ND |

ND: not determined,
[*]% inhibition at 10 μM concentration

Example 25

In Vitro Cell-Based Proliferation Assays

Cell-based assays were performed using the described cell lines, grown in the appropriate Growth Mediums containing 10% fetal bovine serum and 1% penicillin-streptomycin. Cancer cells were plated at 15,000 cells/well in 96-well plates and allowed to attach overnight. Inhibitors were dissolved in DMSO and then diluted to concentrations ranging from 0.1-25 μM with a final DMSO concentration of 0.1%. Cell viability was determined after 72 hours incubation periods. To determine anti-proliferative effects of inhibitors, cellular proliferation was determined using the colorimetric MTT cell viability assay kit, as described by the manufacture (ATCC). Effective doses at 50% cell proliferation inhibition ($ED_{50}$) were determine by plotting the percent difference in absorbance for each concentration of inhibitor with respect to the vehicle control (DMSO only).

TABLE 2

Effective Concentrations ($EC_{50}$) Values on Cell Viability,

| | | $EC_{50}$ (μM) | | | | | |
|---|---|---|---|---|---|---|---|
| | | Liver | | Kidney | Prostate | Breast | |
| Compound | Structure | HepG2 | Huh-7 | ACHN | PC-3 | T47D | SKBR3 |
| Sorafenib | 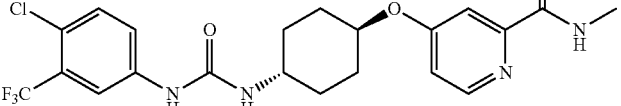 | 4.5 | 4.2 | 4.0 | 5.5 | 3.0 | 6.5 |
| 2278 (t-CUPM) |  | 7.0 | 8.0 | 7.5 | 7.0 | 5.0 | 8.0 |
| 2319 (c-CUPM) | 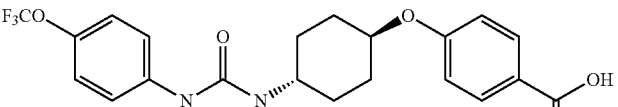 | 7.5 | 8.5 | ND | ND | ND | 8.0 |
| 1728 |  | 15 | 20 | 15 | ND | ND | ND |

TABLE 2-continued

Effective Concentrations (EC₅₀) Values on Cell Viability.

| | | EC$_{50}$ (μM) | | | | | |
|---|---|---|---|---|---|---|---|
| | | Liver | | Kidney | Prostate | Breast | |
| Compound | Structure | HepG2 | Huh-7 | ACHN | PC-3 | T47D | SKBR3 |
| 2227 | F$_3$CO-phenyl-NH-C(O)-NH-cyclohexyl-O-phenyl-C(O)NHMe | 7.0 | 5.5 | 6.5 | 10 | >25 | >25 |
| 1471 | adamantyl-NH-C(O)-NH-cyclohexyl-O-phenyl-C(O)OH | >25 | >25 | >25 | ND | ND | ND |
| 2225 | adamantyl-NH-C(O)-NH-cyclohexyl-O-phenyl-C(O)NHMe | 6.0 | 7.0 | 4.5 | 2.0 | 4.5 | 7.5 |

Figure 4:
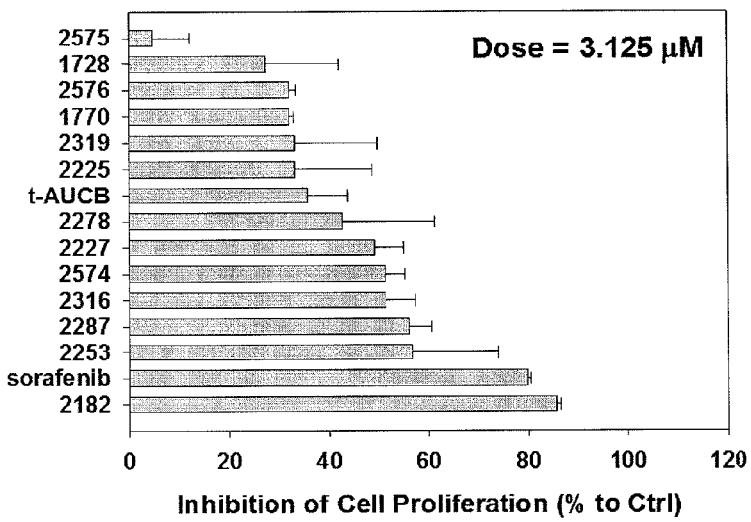
FIG. 4 shows dose dependence of a sEH inhibitor (t-TUCB), a MAPK inhibitor (sunitinib) and a combination inhibitor (2278) on Hep G2 cell viability. The sEH inhibitor t-TUCB has a limited effect on the cancer cells. However, when administered in combination with to sunitinib, a MAPK inhibitor, it potentiates this latter compound's ability to kill cancer cells. Compound 2278, which inhibits both sEH and MAPK (see Table 1) is more efficient than sunitinib in combination or not, with t-TUCB, in killing the cancer cells.

The effective concentrations on cell viability were determined using the MTT cell viability assay kit.
ND = Not determined.
HepG2 and Huh-7 are hepatoma cell lines;
ACHN is a renal cell carcinoma cell line;
PC-3 is a prostate cancer cell line;
T47D and SKBR3 are breast cancer cell lines Cell-based assay were also performed using HUVEC. Human umbilical vein endothelial cells (HUVEC, Clonetics®) were purchased from Lonza (Walkersville, Md.) and cultured in EGM-2 medium with supplements according to the manufacturer's instructions. All experiments with HUVEC were conducted with cells from passage 2 to 4. HUVEC cells were plated into 96-well plates at 1.0-1.5×10³ cells per well in 100 μL complete medium. After 24 h, the medium was replaced with fresh medium containing test compounds or DMSO vehicle. After another 2 day of incubation, cell viability was assessed by MTT (Sigma-Aldrich) assay. See FIG. 4.

Example 26

Cell Based Proliferation Assays Performed by National Cancer Institute

The human tumor cell lines of the cancer screening panel are grown in RPMI 1640 medium containing 5% fetal bovine serum and 2 mM L-glutamine. For a typical screening experiment, cells are inoculated into 96 well microtiter plates in 100 μL at plating densities ranging from 5,000 to 40,000 cells/well depending on the doubling time of individual cell lines. After cell inoculation, the microtiter plates are incubated at 37° C., 5% CO2, 95% air and 100% relative humidity for 24 h prior to addition of experimental drugs. After 24 h, two plates of each cell line are fixed in situ with TCA, to represent a measurement of the cell population for each cell line at the time of drug addition (Tz).

Experimental drugs are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 μg/ml gentamicin. Additional four, 10-fold or ½ log serial dilutions are made to provide a total of five drug concentrations plus control. Aliquots of 100 μl of these different drug dilutions are added to the appropriate microtiter wells already containing 100 μl of medium, resulting in the required final drug concentrations. Following drug addition, the plates are incubated for an additional 48 h at 37° C., 5% CO2, 95% air, and 100% relative humidity.

For adherent cells, the assay is terminated by the addition of cold TCA. Cells are fixed in situ by the gentle addition of 50 μl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 μl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm.

For suspension cells, the methodology is the same except that the assay is terminated by fixing settled cells at the bottom of the wells by gently adding 50 μl of 80% TCA (final concentration, 16% TCA).

Using the seven absorbance measurements [time zero, (Tz), control growth, (C), and test growth in the presence of drug at the five concentration levels (Ti)], the percentage growth is calculated at each of the drug concentrations levels. Percentage growth inhibition is calculated as:

[(Ti−Tz)/(C−Tz)]×100 for concentrations for which Ti>/=Tz

[(Ti−Tz)/Tz]×100 for concentrations for which Ti<Tz.

Three dose response parameters are calculated for each experimental agent. Growth inhibition of 50% (GI50) is calculated from [(Ti−Tz)/(C−Tz)]×100=50, which is the drug concentration resulting in a 50% reduction in the net protein increase (as measured by SRB staining) in control cells during the drug incubation. The drug concentration resulting in total growth inhibition (TGI) is calculated from Ti=Tz. The LC50 (concentration of drug resulting in a 50% reduction in the measured protein at the end of the drug treatment as compared to that at the beginning) indicating a net loss of cells following treatment is calculated from [(Ti−Tz)/Tz]×100=−50. Values are calculated for each of these three parameters if the level of activity is reached; however, if the effect is not reached or is exceeded, the value for that parameter is expressed as greater or less than the maximum or minimum concentration tested. See http://dtp.nci.nih.gov/branches/btb/ivclsp.html.

Example 27

Pharmacokinetic (PK) Profiles of 2278 (t-CUPM) and Sorafenib in a Murine Model

Figure 5:
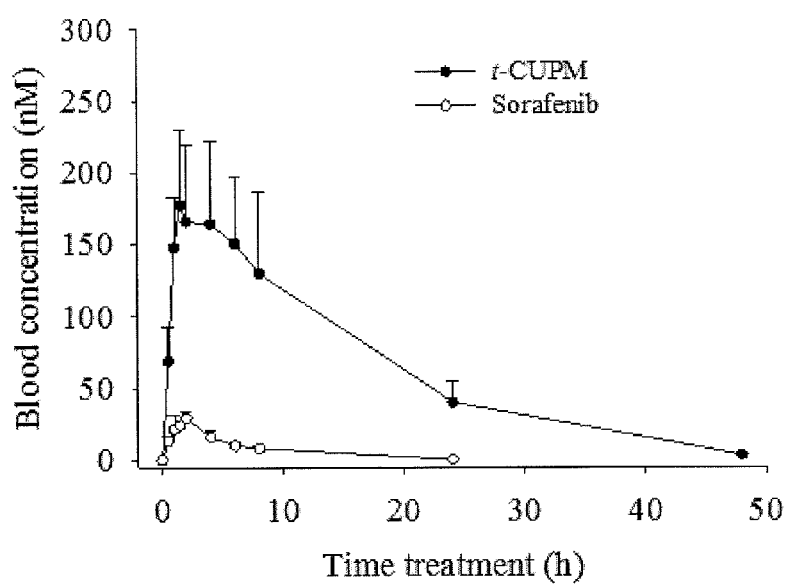
FIG. 5 shows blood concentration-time courses of t-CUPM and sorafenib after cassette oral administration to mice at the dose of 1 mg/kg. Each point represents the mean±s.d. of three mice.
Figure 6:
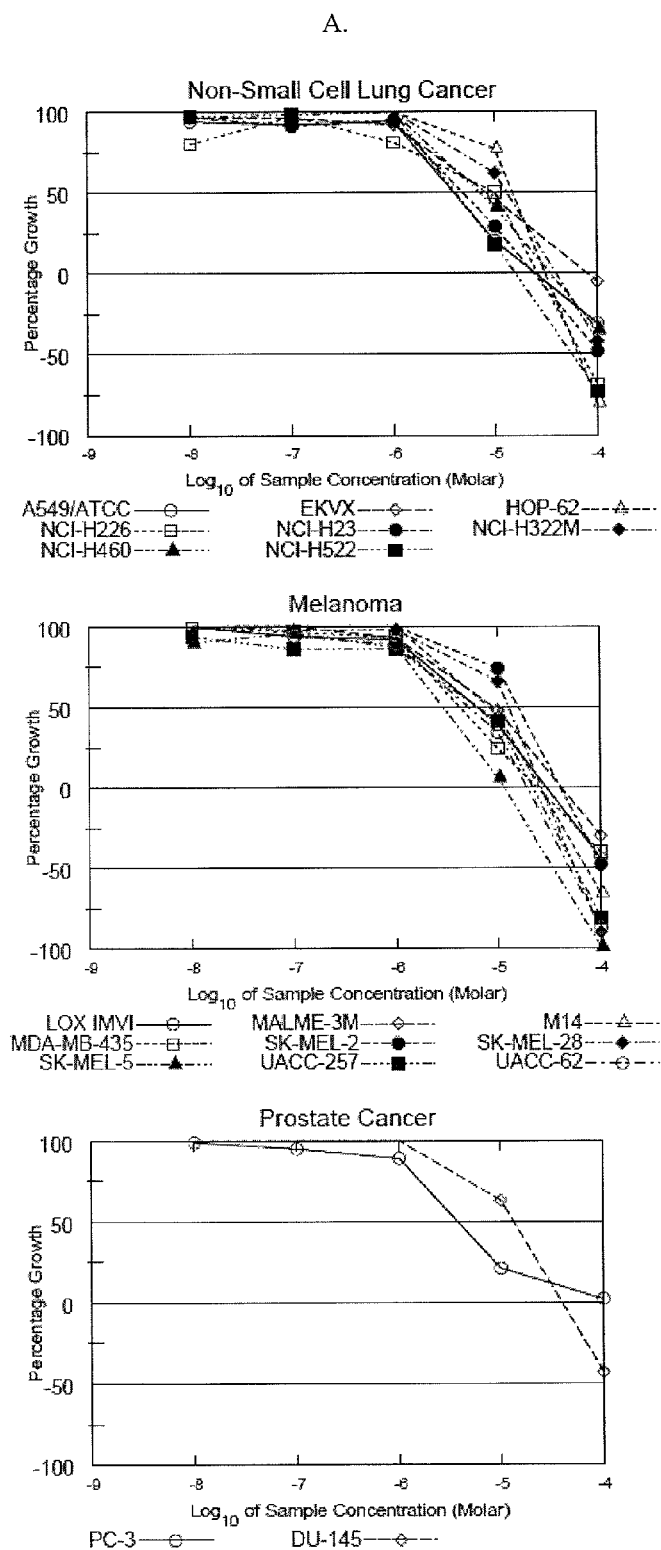
FIGS. 6a-c show the dose response effects of compound 2278 (t-CUPM) on various cancer cell lines. The dose-response curves were created by plotting the percentage growth (PG) values against the $\log_{10}$ of the corresponding concentration for every cell line. The cell line curves are grouped by subpanel. Horizontal lines are provided at the PG values of +50.0 and −50. The concentrations corresponding to points where the curves cross these lines are the GI50, TGI, and $LC_{50}$, respectively.
Figure 6:
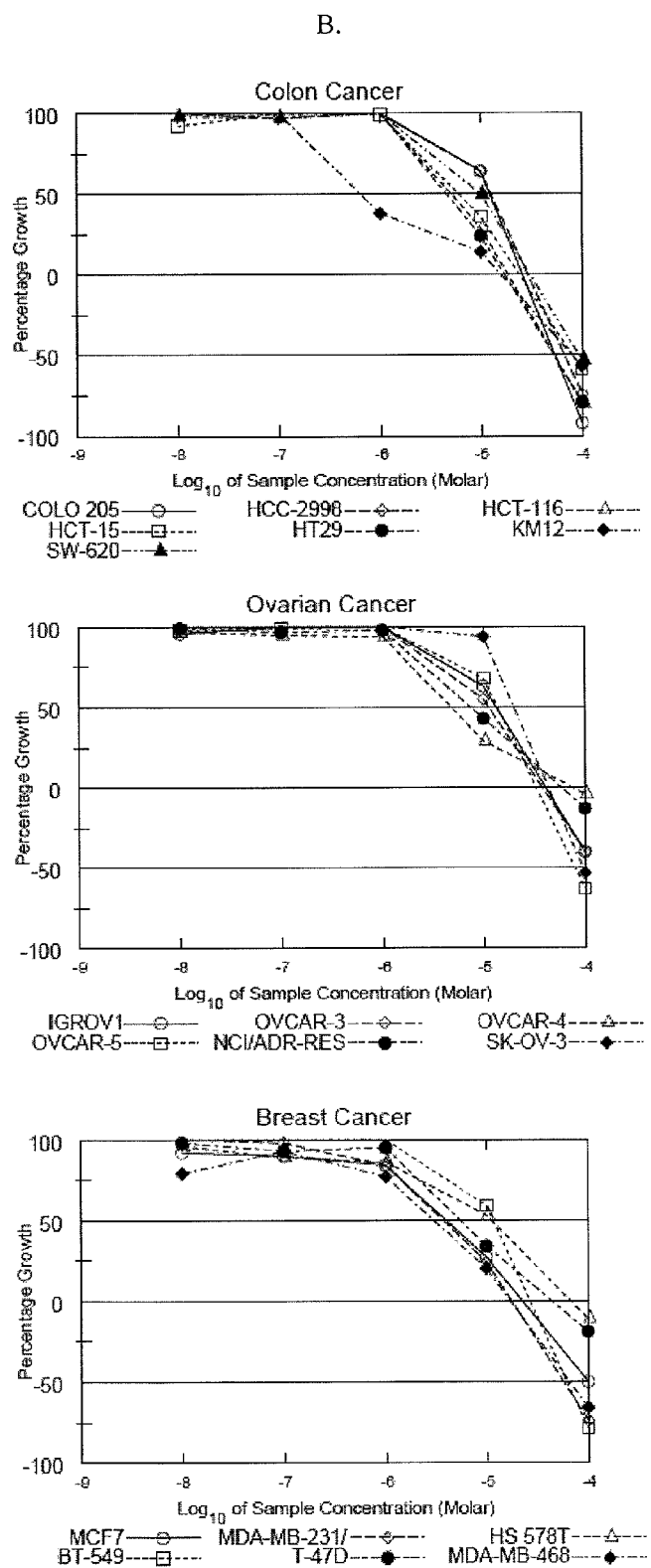
Figure 6:
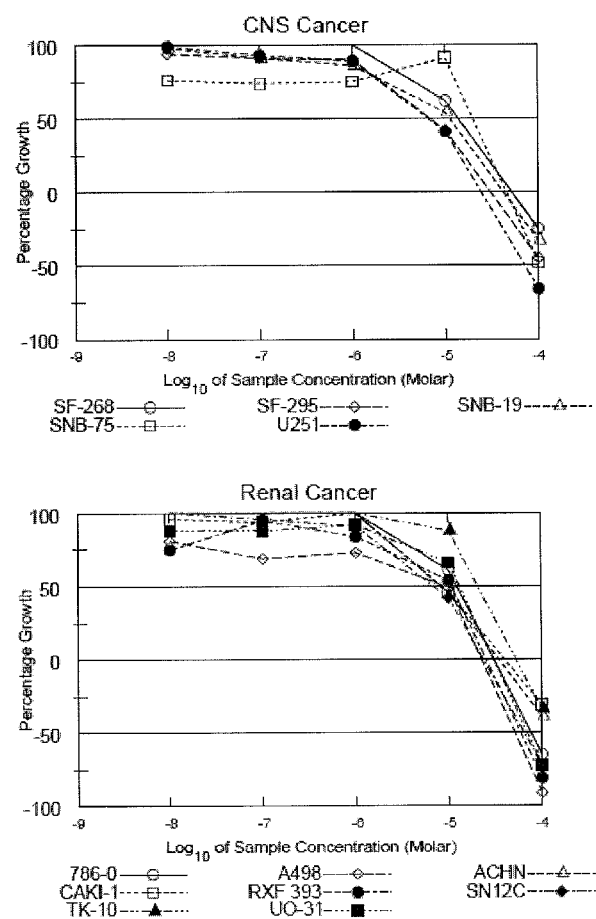
Figure 7:
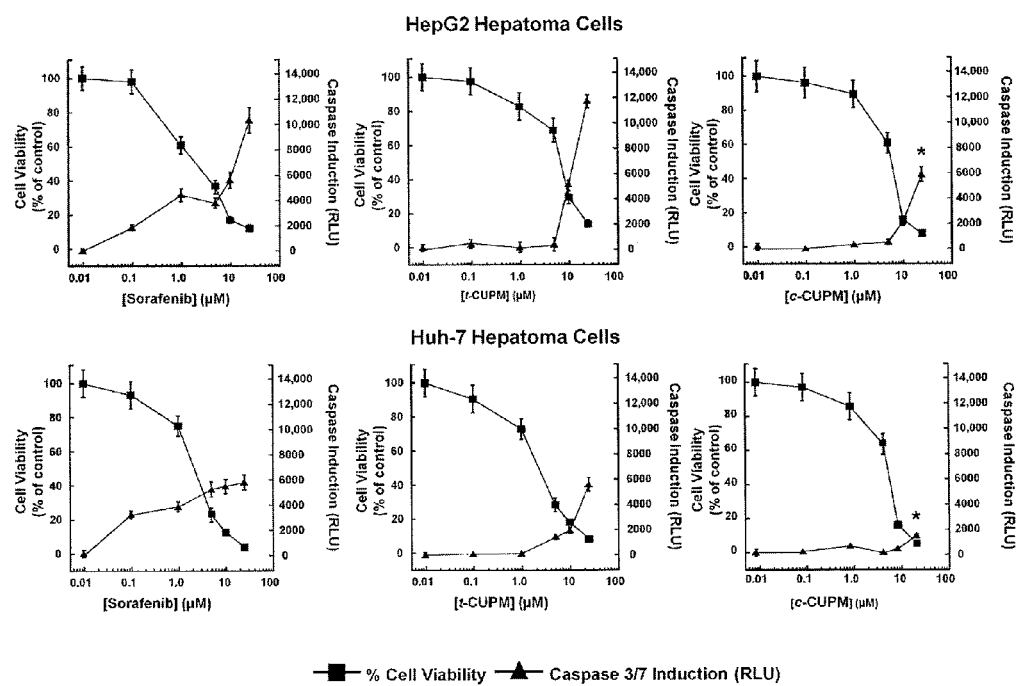
FIG. 7 shows the dose response effects of sorafenib and analogues on HepG2 (top panel) and Huh-7 (bottom panel) cell viability and caspase 3/7 induction. Data for cell viability (MTT assay) and caspase 3/7 induction (luminescence) were determined after a 72 hour incubation period for each compound. *P value <0.05 for c-CUPM caspase induction as compared to sorafenib and t-CUPM. Sorafenib analogues display similar effects to sorafenib and hepatoma cell viability.
Figure 8:
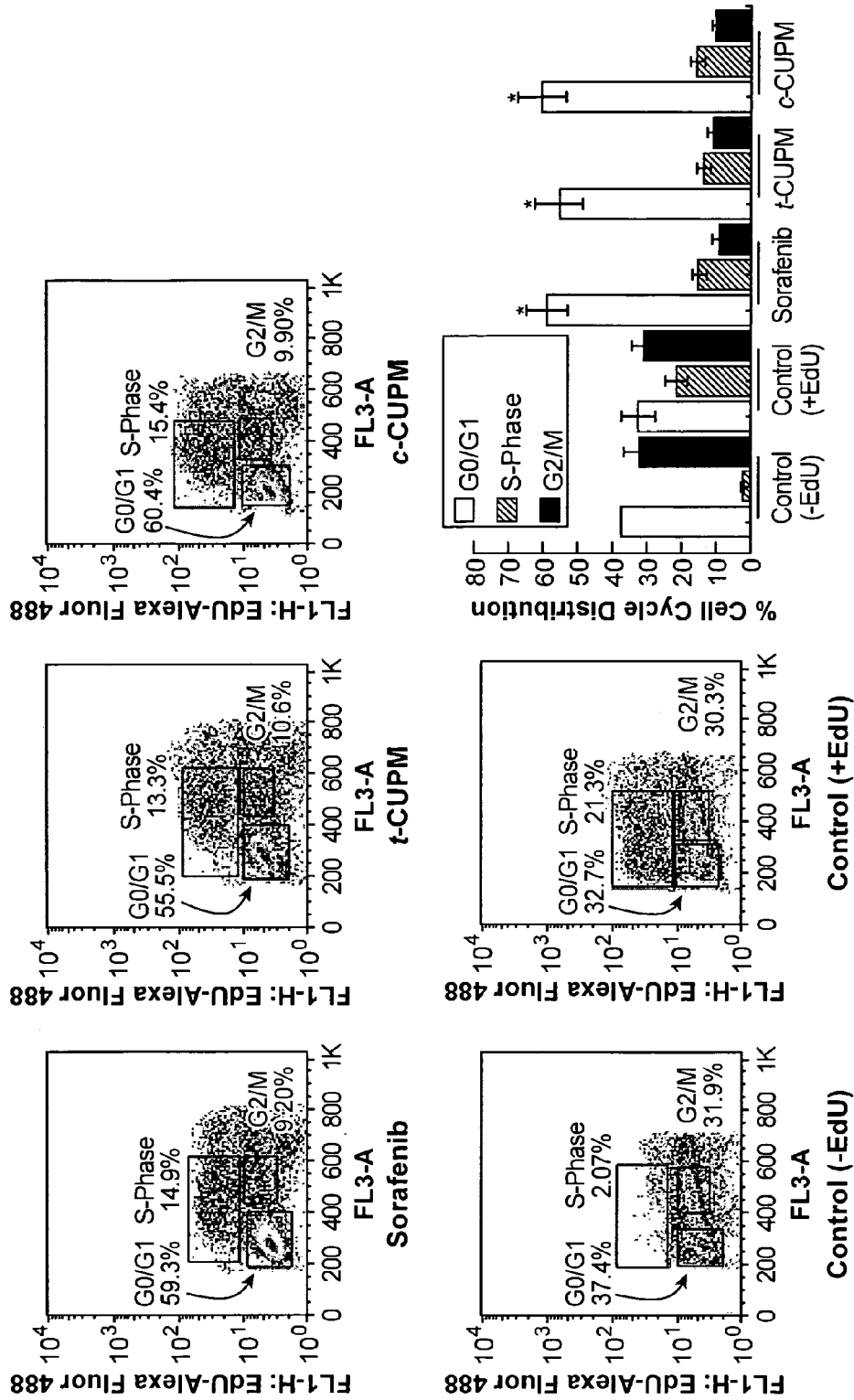
FIG. 8 shows the effects of sorafenib analogues on hepatoma cell cycle distribution. HepG2 cells were exposed at concentrations of 30 μM for 24 hours and fluorescence detection of incorporated EdU and 7AAD was analyzed by flow cytometry. Example histograms presented (n=3). *P value <0.05 as compared to DMSO control (+EdU). Sorafenib analogues are as effective as sorafenib in inhibiting cell cycle progression.
Figure 9:
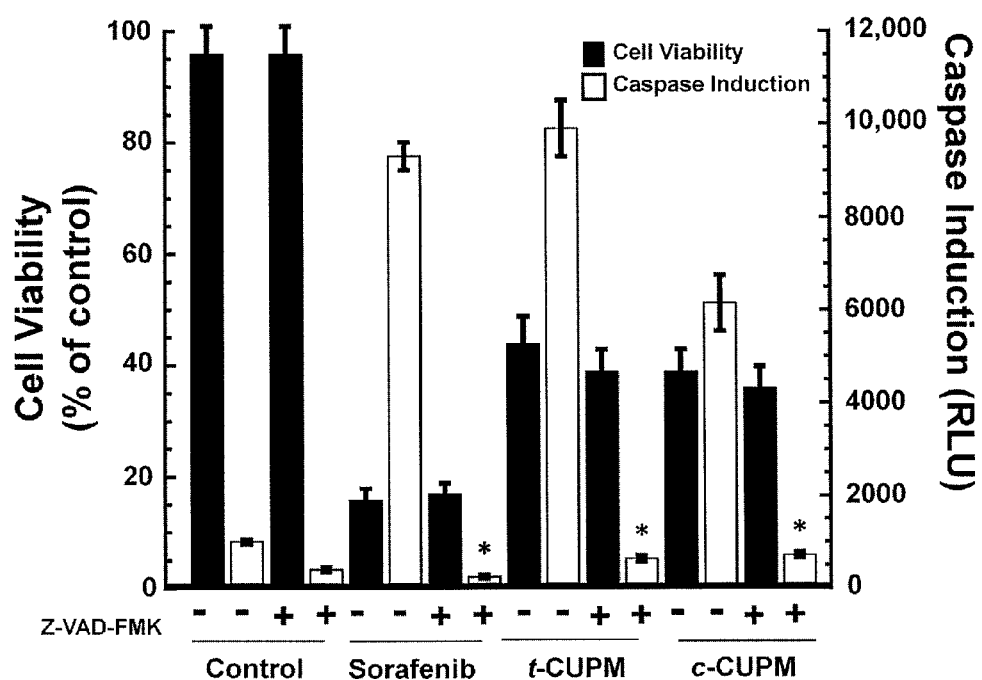
FIG. 9 shows cell viability responses of sorafenib analogues. The HepG2 cells were pre-incubated for 60 minutes with the pan-caspase inhibitor, Z-VAD-FMK (20 μM), prior to 24 hour incubation with 30 μM of test compound. No significant difference in cell viability was observed with the addition of Z-VAD-FMK for all compounds. *P value <0.05 as compared no Z-VAD-FMK addition. These data demonstrate a caspase-independent mechanism of cell death by sorafenib and the analogues.
Figure 10:
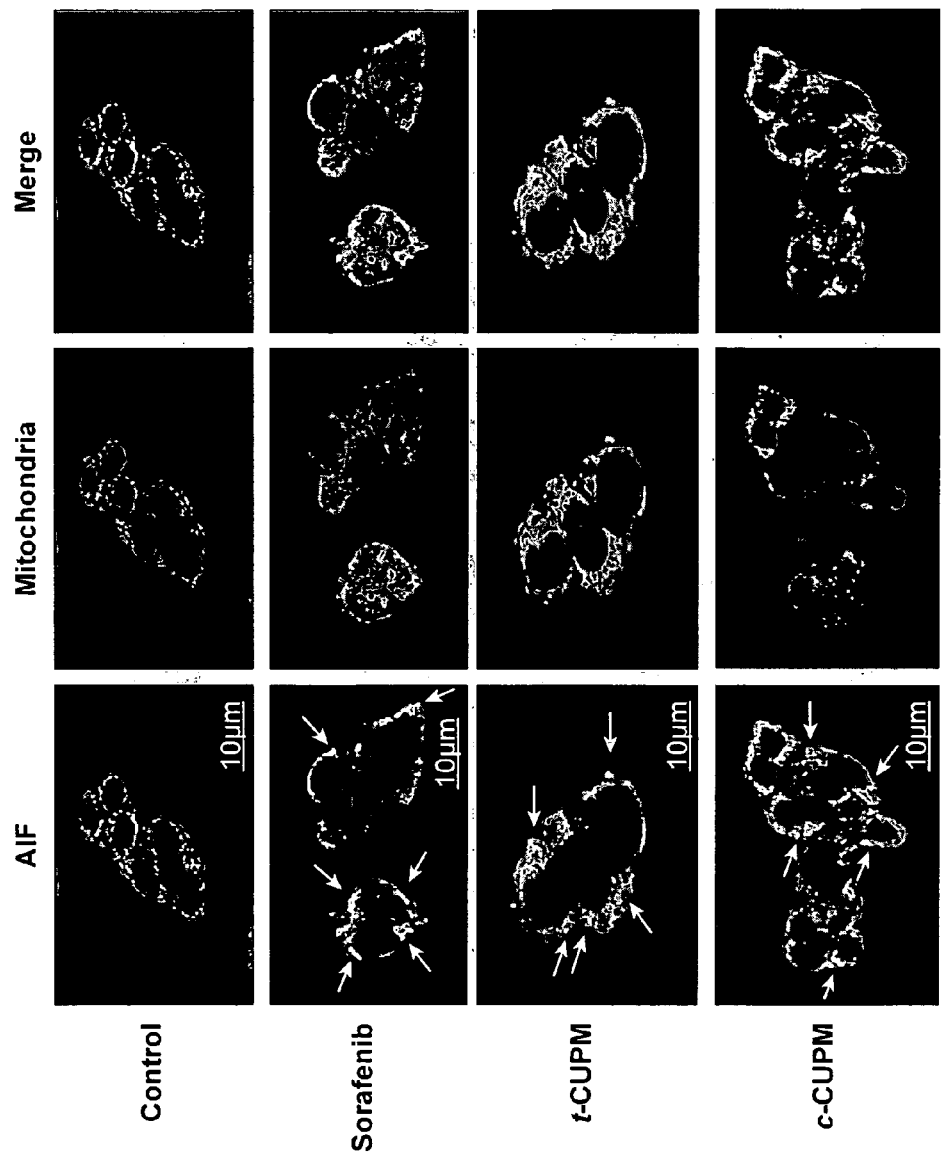
FIG. 10 shows the effects of sorafenib and analogues on mitochondrial depolarization and AIF nuclear translocation. HepG2 cells were incubated at 30 μM of each compound for 6 hours, followed by medium replacement containing 100 nM MitoTracker® Red CMXRos for 15 minutes. Cells were fixed, and then incubated with AIF primary antibody then stained using Alexa Fluor® 488 conjugated secondary antibody. Nuclei were stained using mounting media with DAPI.

The blood levels of t-CUPM and sorafenib following cassette oral administration to mice were determined and are illustrated in FIG. 5. Oral dosing of t-CUPM resulted in the higher blood levels than that of sorafenib throughout the complete time course (48 h). The major PK parameters based on a non-compartmental analysis are summarized in Table 3. Oral administration of t-CUPM resulted in significantly higher $C_{max}$ and $AUC_t$ than but similar $T_{max}$ and $t_{1/2}$ to that of sorafenib, which indicates that t-AUPM may be more potent in vivo than sorafenib.

TABLE 3

Pharmacokinetic parameters of t-CUPM and sorafenib after cassette oral dosing with a non-compartmental analysis

| Inhibitors | $R^2$ | $C_{max}$ (nM) | $T_{max}$ (h) | $t_{1/2}$ | $AUC_t$ (nM*h) |
|---|---|---|---|---|---|
| t-CUPM | 0.97 ± 0.04 | 190 ± 50 | 1.7 ± 0.8 | 2.2 ± 1.6 | 3000 ± 550 |
| sorafenib | 0.98 ± 0.01 | 30 ± 5 | 2 ± 0 | 1.5 ± 0.5 | 200 ± 12 |

$R^2$ is the square of the correlation coefficient between predict and observed value; $T_{max}$, the time of maximum concentration; $C_{max}$, the maximum blood concentration; $t_{1/2}$, half-life; $AUC_t$, area under the concentration-time curve to terminal time.

Example 28

Pharmacokinetic (PK) Study of 1-CUPM and Sorafenib in a Murine Model

Male Swiss Webster mice (10-week old, 30-35 g) were used for PK studies. Equal amount of sorafenib and t-CUPM was dissolved in oleic acid-rich triglyceride containing 10% PEG400 (v/v) to give a clear solution for cassette oral administration at a dose of 1 mg/kg (N=3). Blood (10 μL) was collected from the tail vein using a pipette tip rinsed with 7.5% EDTA(K3) at 0, 0.5, 1, 1.5, 2, 4, 6, 8, 24 h after administration of the inhibitors. Each blood sample was immediately transferred to a tube containing 50 μL of water containing 0.1% EDTA. After being mixed strongly on a Vortex for 1 min, all samples were stored at −80° C. until analysis.

The extraction of sEHIs from blood was performed by a slight modification of a previous method [26]. Specifically, ethyl acetate (200 μL) was added after the addition of internal solution I [10 μL, 500 nmol of 1-(4-chloro-3-trifluoromethanylphenyl-3-(1-cyclopropanecarboxylpiperidin-4-yl)urea in 1 L methanol] to each thawed blood sample instead of prior to the addition of internal solution I.

The blood concentrations of compounds were determined using a HPLC-MS/MS method which was validated to assure acceptable accuracy and precision (accuracy more than 95% with RSD less than 10%). Specifically, chromatographic separation was performed on an Agilent 1200 SL liquid chromatography instrument (Agilent, Corporation, Palo Alto, Calif.) equipped with a 100×4.6 mm LURA C18 3 μm column (Phenomenex. Torrance, Calif.) held at 50° C. The mobile phase consisted of water/acetic acid (999/1 v/v, solvent A) and acetonitrile/acetic acid (999/1 v/v; solvent B) employing gradient elution at a flow rate of 0.4 ml/min. The gradient programme was as follows: initial 0-3 min, 60% of solvent B; 3-10 min, linear change from 60% of solvent B to 98% of solvent B; 10-13 min, 98% of solvent B, 13-15 min, linear change from 98% of solvent B to 60% of solvent B. The injection volume was 10 μL and the samples were kept at 4° C. in the auto sampler. Analytes were detected by negative mode electrospray ionizations tandem quadrupole trap mass spectrometry in multiple reaction-monitoring mode (MRM) on a Trap 4000 Mass Spectrometer (ABI, Milford, Mass.). The parameters of MS condition were the same as presented previously [24]. The precursor and dominant product ions used to set up the transition monitored in the MRM mode were 463.1 and 194 for sorafenib, and 469.1 and 194 for t-CUPM, respectively.

Example 29

Recombinant Kinase Activity Assay

Inhibitor Concentration at 50% enzyme inhibition ($IC_{50}$) values were calculated by quantifying the end-point ADP production from each kinase reaction using the ADP-Glo™ Kinase Assay (Promega, Madison, Wis.) as described by the manufacturer. Reactions were performed in Tris buffer (50 mM pH 7.5, RT) containing 20 mM $MgCl_2$ and 0.1% Bovine Serum Albumin. Each assay was performed in 60 μL of the solution in 10×75 mm borosilicate glass test tubes and allowed to continuously shake during the duration of the assay. The total ADP generated was quantified by transferring 25 μL (2×) of each assay to a 96-well luminescence assay plate, followed by the addition of 25 μL of ADP-Glo™ Reagent (45 min incubation) to remove any remaining ATP. For luminescence readings, 50 μL of Kinase Detection Reagent™ (45 min incubation) was added to convert the ADP generated from the kinase reaction to ATP, and luminescent intensity was measured using a luciferase/luciferin reaction, as indicated by the manufacturer. Full length recombinant CRAF kinase and its respective substrate, recombinant MEK1, were purchased from US Biological (Swampscott, Mass.). All assays were performed at 10 nM CRAF, 1 μM MEK1, 10 μM ATP, at 22° C. for 2 hours. Initial time-based measurements were performed to ensure a linear turnover throughout the duration of the assay (data not shown). Inhibitors were dissolved in DMSO and diluted to appropriate initial concentrations so that the addition of 1 μL yielded the desired final concentration. IC$_{50}$ values were obtained by determining the change in the ADP production (luminescent signal) at various inhibitor concentrations as compared to the control assay. Individual data sets were performed in duplicate and each IC$_{50}$ was determined by the mean and standard deviation of three separate experiments. The data were fit to a saturation curve using KaleidaGraph graphing program (Synergy Software) to determine the concentration for the inhibition at 50% activity (IC$_{50}$).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of Formula I:

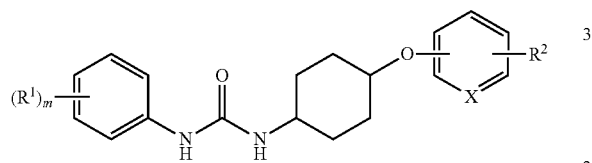

(I)

wherein
- R$^1$ is selected from the group consisting of halogen, C$_{1-6}$ haloalkyl and C$_{1-6}$ haloalkoxy;
- R$^2$ is selected from the group consisting of —CN, C$_{1-6}$ haloalkyl, C$_{1-6}$ haloalkoxy, —C(O)OR$^{2a}$ and —C(O)NR$^{2a}$R$^{2b}$;
- R$^{2a}$ and R$^{2b}$ are each independently selected from the group consisting of H, C$_{1-6}$ alkyl and C$_{3-8}$ cycloalkyl, or are taken together to form a 5- or 6-membered heterocycloalkyl ring;
- X is —N—;
- subscript m is an integer from 1 to 3;

and salts and isomers thereof.

2. The compound of claim 1, wherein
- R$^1$ is selected from the group consisting of halogen, C$_{1-6}$ haloalkyl and C$_{1-6}$ haloalkoxy;
- R$^2$ is selected from the group consisting of C$_{1-6}$ haloalkyl, C$_{1-6}$ haloalkoxy, —C(O)OR$^{2a}$ and —C(O)NR$^{2a}$R$^{2b}$;
- R$^{2a}$ and R$^{2b}$ are each independently selected from the group consisting of H, C$_{1-6}$ alkyl and C$_{3-8}$ cycloalkyl;
- X is —N—;
- subscript m is an integer from 1 to 3;

and salts and isomers thereof.

3. The compound of claim 1, wherein R$^2$ is selected from the group consisting of —C(O)OR$^{2a}$ and —C(O)NR$^{2a}$R$^{2b}$.

4. The compound of claim 1, having the formula:

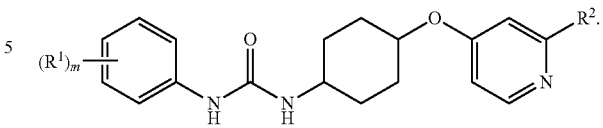

5. The compound of claim 1, having the formula:

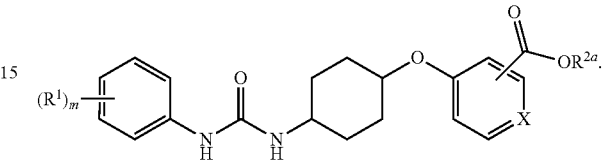

6. The compound of claim 1, having the formula:

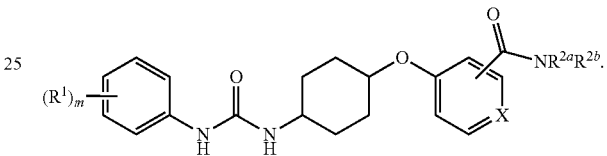

7. The compound of claim 1, having the formula:

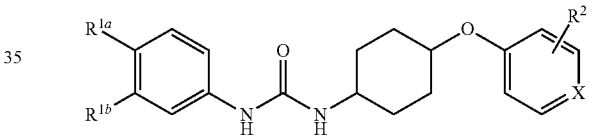

wherein R$^{1a}$ and R$^{1b}$ are each independently selected from the group consisting of halogen and C$_{1-6}$ haloalkyl.

8. The compound of claim 1, having the formula:

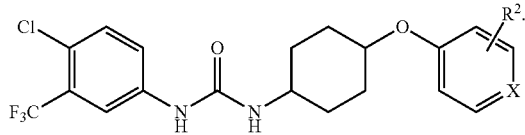

9. The compound of claim 1, selected from the group consisting of:

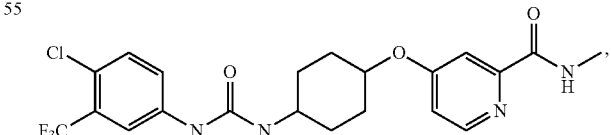

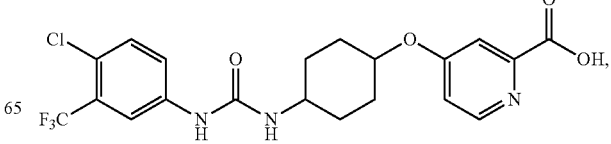

-continued

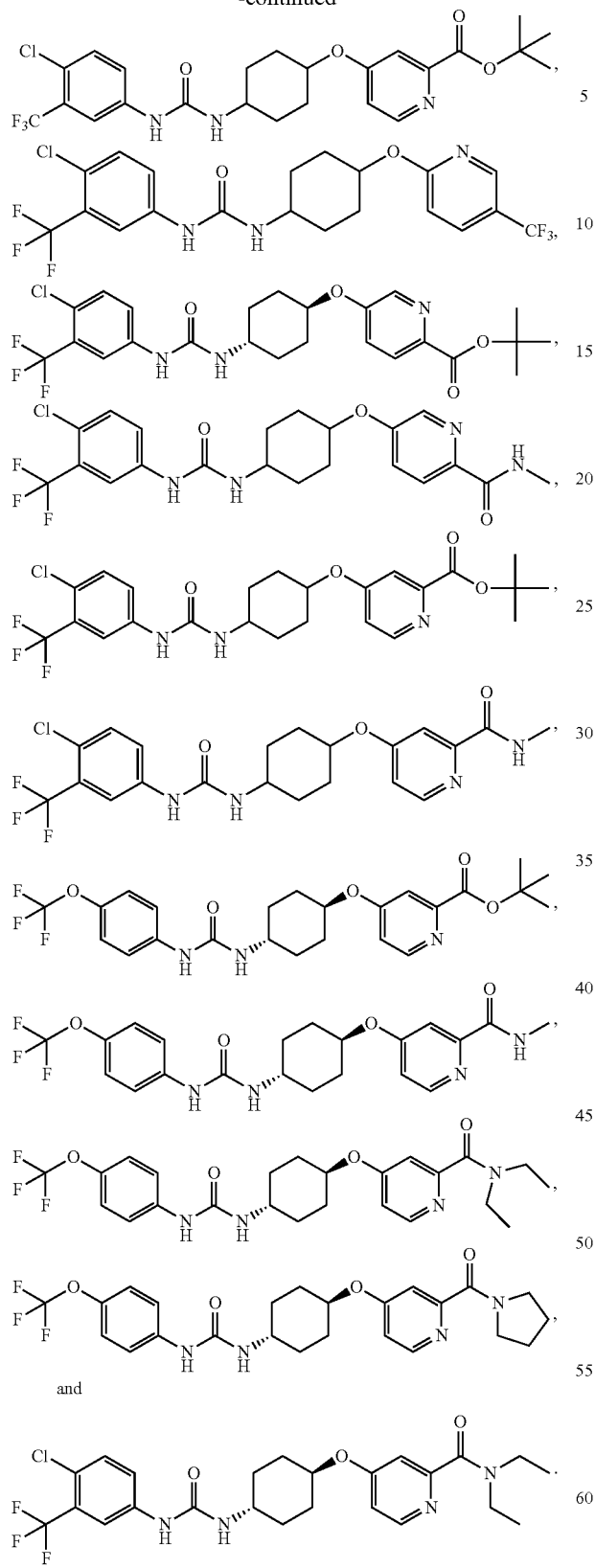

and

10. A pharmaceutical composition comprising a compound of claim 1 and a pharmaceutically acceptable excipient.

11. The compound of claim 1, having the formula:

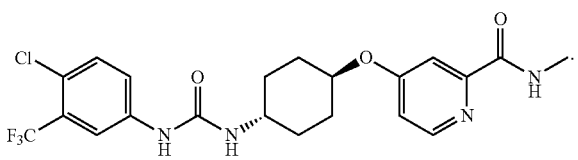 [SMILES: CNC(=O)c1cc(O[C@H]2CC[C@H](NC(=O)Nc3ccc(Cl)c(C(F)(F)F)c3)CC2)ccn1]

12. A compound of Formula I:

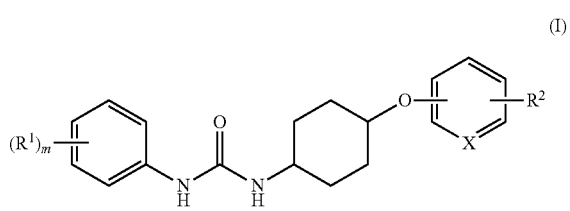

(I)

wherein
R$^1$ is selected from the group consisting of halogen, C$_{1-6}$ haloalkyl and C$_{1-6}$ haloalkoxy;
R$^2$ is —C(O)NR$^{2a}$R$^{2b}$;
R$^{2a}$ and R$^{2b}$ are each independently selected from the group consisting of H, C$_{1-6}$ alkyl and C$_{3-8}$ cycloalkyl, or are taken together to form a 5- or 6-membered heterocycloalkyl ring;
X is selected from the group consisting of —CH— and —N—;
subscript m is an integer from 1 to 3;
and salts and isomers thereof.

13. The compound of claim 12, having the formula:

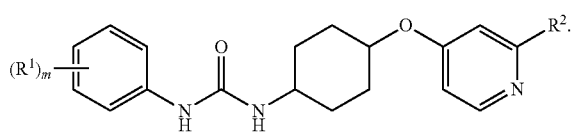

14. The compound of claim 12, having the formula:

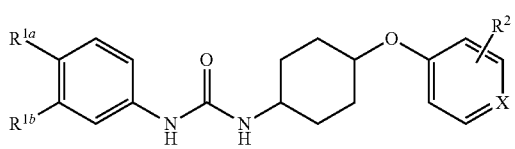

wherein R$^{1a}$ and R$^{1b}$ are each independently selected from the group consisting of halogen and C$_{1-6}$haloalkyl.

15. The compound of claim 12, having the formula:

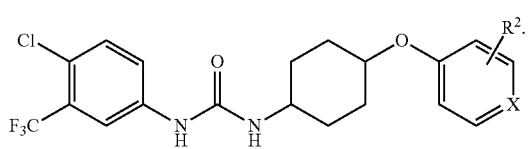

16. The compound of claim 12, selected from the group consisting of:

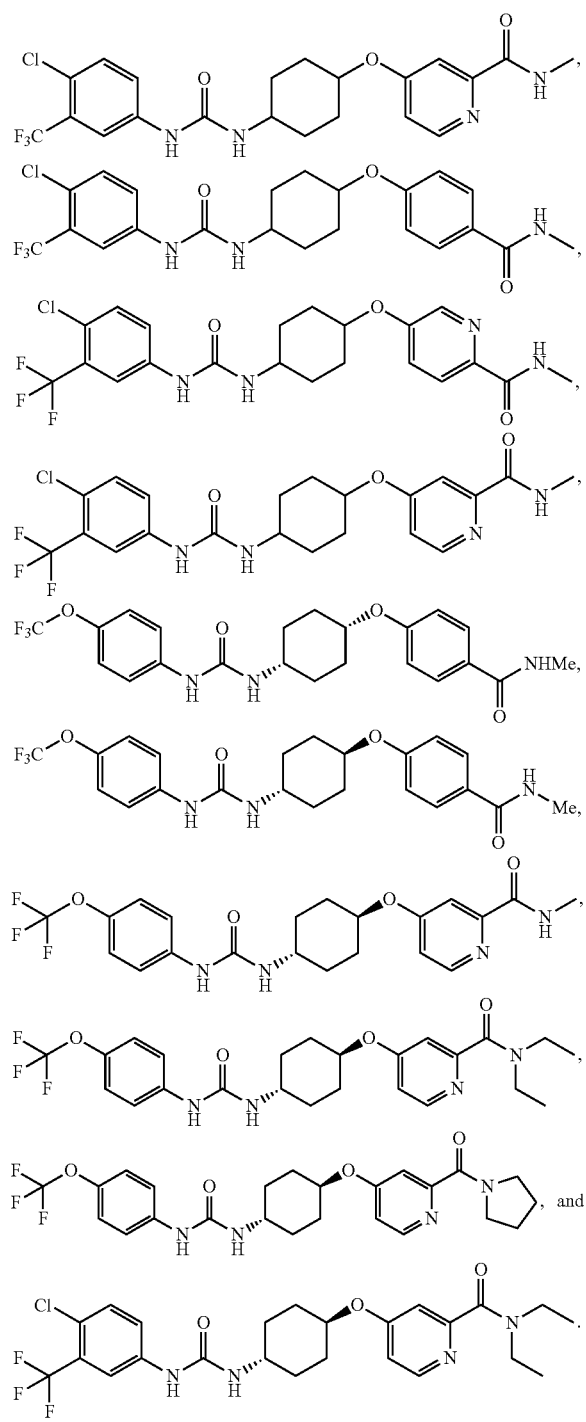

17. The compound of claim 12, having the formula:

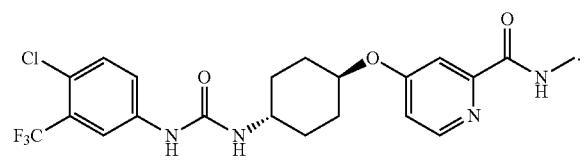 [SMILES: CNC(=O)c1cc(O[C@H]2CC[C@H](NC(=O)Nc3ccc(Cl)c(C(F)(F)F)c3)CC2)ccn1]

18. A pharmaceutical composition comprising a compound of claim 12 and a pharmaceutically acceptable excipient.

19. A compound having the formula:

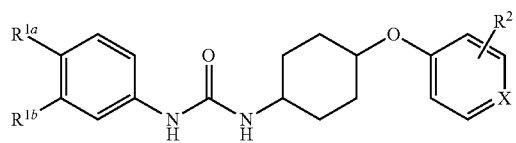

wherein

- $R^{1a}$ and $R^{1b}$ are each independently selected from the group consisting of halogen and $C_{1-6}$ haloalkyl;
- $R^2$ is selected from the group consisting of —CN, $C_{1-6}$ haloalkyl, $C_{1-6}$ haloalkoxy, —C(O)OR$^{2a}$ and —C(O)NR$^{2a}$R$^{2b}$;
- $R^{2a}$ and $R^{2b}$ are each independently selected from the group consisting of H, $C_{1-6}$ alkyl and $C_{3-8}$ cycloalkyl, or are taken together to form a 5- or 6-membered heterocycloalkyl ring;
- X is selected from the group consisting of —CH— and —N—;

and salts and isomers thereof.

20. The compound of claim 19, wherein $R^2$ is selected from the group consisting of —C(O)OR$^{2a}$ and —C(O)NR$^{2a}$R$^{2b}$.

21. The compound of claim 19, having the formula:

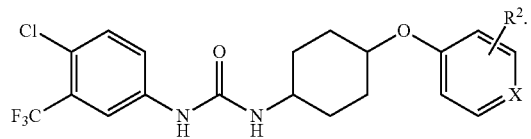

22. The compound of claim 19, selected from the group consisting of:

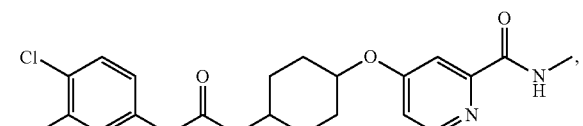

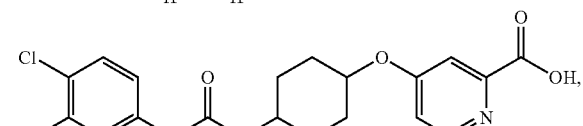

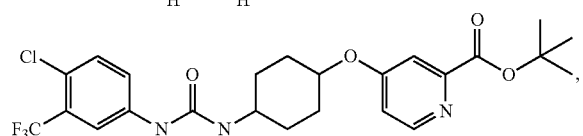

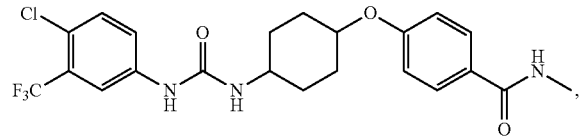

-continued
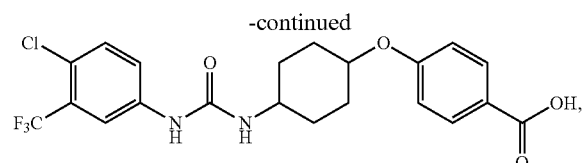
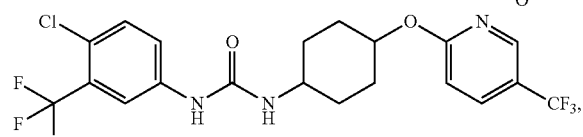
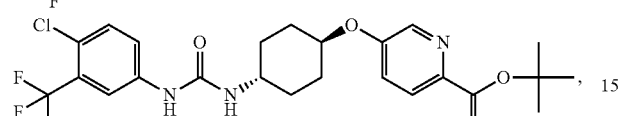
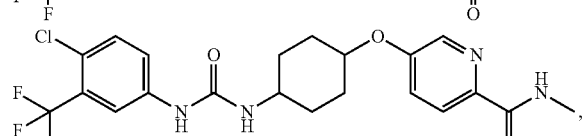
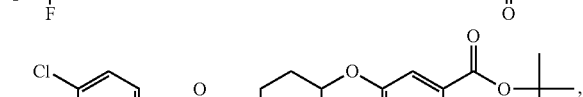
-continued
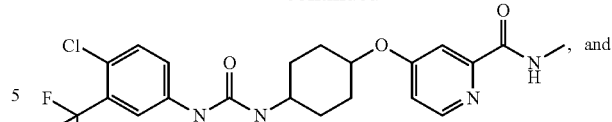
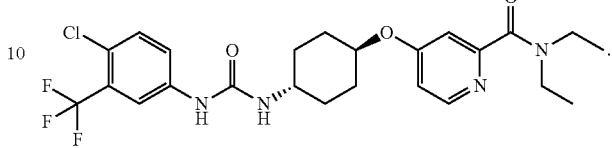
23. The compound of claim 19, having the formula:
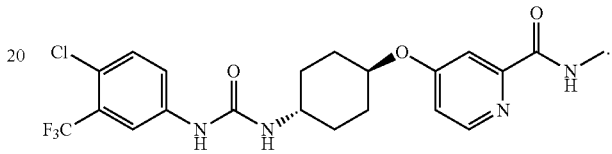
24. A pharmaceutical composition comprising a compound of claim 19 and a pharmaceutically acceptable excipient.
* * * * *